(12) United States Patent
Zoghbi et al.

(10) Patent No.: US 7,442,688 B2
(45) Date of Patent: Oct. 28, 2008

(54) COMPOSITION AND METHODS FOR THE THERAPEUTIC USE OF AN ATONAL-ASSOCIATED SEQUENCE FOR DEAFNESS, OSTEOARTHRITIS AND ABNORMAL CELL PROLIFERATION

(75) Inventors: Huda Y. Zoghbi, Houston, TX (US); Hugo Bellen, Houston, TX (US); Nessan Bermingham, Houston, TX (US); Bassem Hassan, Houston, TX (US); Nissim Ben-arie, Jerusalem (IL)

(73) Assignee: Baylor College of Medicine, Houston, TX (US)

( * ) Notice: Subject to any disclaimer, the term of this patent is extended or adjusted under 35 U.S.C. 154(b) by 423 days.

(21) Appl. No.: 10/860,373

(22) Filed: Jun. 3, 2004

(65) Prior Publication Data

US 2004/0231009 A1 Nov. 18, 2004

Related U.S. Application Data

(62) Division of application No. 09/585,645, filed on Jun. 1, 2000, now Pat. No. 6,838,444.

(60) Provisional application No. 60/176,993, filed on Jan. 19, 2000, provisional application No. 60/137,060, filed on Jun. 1, 1999.

(51) Int. Cl.
*A61K 31/70* (2006.01)
*C07H 21/02* (2006.01)
*C12N 15/00* (2006.01)

(52) U.S. Cl. .................. 514/44; 536/23.1; 435/320.1

(58) Field of Classification Search .................. None
See application file for complete search history.

(56) References Cited

U.S. PATENT DOCUMENTS

| | | | |
|---|---|---|---|
| 5,770,580 | A | 6/1998 | Ledley et al. |
| 5,792,751 | A | 8/1998 | Ledley et al. |
| 5,837,681 | A | 11/1998 | Magal |
| 5,929,041 | A | 7/1999 | Magal |

FOREIGN PATENT DOCUMENTS

| | | | |
|---|---|---|---|
| EP | 0613945 | A1 | 9/1994 |
| WO | WO 95/19182 | A1 | 7/1995 |
| WO | WO 97/17983 | A1 | 5/1997 |
| WO | WO 98/00014 | A1 | 1/1998 |
| WO | WO 98/13048 | A1 | 4/1998 |
| WO | WO 98/19700 | | 5/1998 |
| WO | WO 98/19700 | A1 | 5/1998 |
| WO | WO 99/06034 | A1 | 2/1999 |
| WO | WO 99/06064 | A1 | 2/1999 |
| WO | WO 99/42088 | A1 | 8/1999 |
| WO | WO 00/23084 | A1 | 4/2000 |
| WO | WO 00/27426 | | 5/2000 |

OTHER PUBLICATIONS

Schwarze SR et al., In vivo *protein transduction: delivery of a biologically active protein into the mouse*, Science, Sep. 3, 1999, pp. 1569-1573, vol. 285, see entire document.
Verma IM et al., *Gene therapy-promises, problems & prospects*, Nature, Sep. 18, 1997, pp. 239-242, pp. 239-242, vol. 389, see entire document.
Ledley FD, *Pharmaceutical approach to somatic gene therapy*, Pharmaceutical Research, Nov. 1996, pp. 1595-1614, vol. 13, No. 11, see entire document.
Chen, P., Johnson, J.E. et al., The role of Math 1 in inner ear development: Uncoupling the establishment of the sensory primordium from hair cell fate determination, Development, 2002, pp. 2495-2505, vol. 129.
Kanzaki, S., Kawamoto, K. et al., From Gene Identification to Gene Therapy, Audiol. Neurootol., 2002, pp. 161-164, vol. 7.
Kawamoto K., Oh, S.-H., et al., The Functional and Structural Outcome of Inner Ear Gene Transfer via the Vestibular and Cochlear Fluids in Mice, Molecular Therapy, Dec. 2001, vol. 4(6).
Zheng, J.L. and Gao, W.-Q., Overexpression of Math1 induces robust production of extra hair cells in postnatal rat inner ears, Nature Neuroscience, Jun. 2000, pp. 580-586, vol. 3(6).
Thibodeau, G.A., et al., *Sense of Hearing and Balance: The Ear*, Unit 3, Communication, Control & Integration, Anatomy & Physiology, 4th Ed., 1999, pp. 454-455, Mosby Inc., St. Louis, MO, USA.
Kawamoto, K., et al., *Math1 Gene Transfer Generated New Cochlear Hair Cells . . .* , The Journal of Neuroscience, Jun. 1, 2003, pp. 4395-4400, 23(11), Society for Neuroscience.
Shou, J., et al., *Robust generation of new hair cells in the mature mammalian inner ear . . .* , Molecular & Cellular Neuroscience, 2003, pp. 169-179, vol. 23, Elsevier Science (USA).
Dooling, R.J., et al., *Recovery of hearing and vocal behavior after hair-cell regeneration*, Proc. Natl. Acad. Sci. USA, Psychology, Dec. 1997, pp. 14206-14210, vol. 94, The National Academy of Sciences.
Carey, J.P., et al., *Hair cell regeneration & recovery of the vestibuloocular reflex . . .* , Journal of Neurophysiology, Nov. 1996, pp. 3301-3312+ cover, vol. 76, No. 5, The American Physiological Society.
Schwab, Markus, H., et al.; Neuronal Basic Helix-Loop-Helix Proteins (NEX, neuroD, NDRF): Spatiotemporal Expression and Targeted Disruption of the NEX Gene in Transgenic Mice, The Journal of Neuroscience (Feb. 15, 1998), OE(4), pp. 1408-1418.

(Continued)

Primary Examiner—Celine X Qian
(74) Attorney, Agent, or Firm—Fulbright & Jaworski LLP

(57) ABSTRACT

Compositions and methods are disclosed for the therapeutic use of an atonal-associated nucleic acid or amino acid sequence. Also, an animal heterozygous for an atonal-associated gene inactivation is also disclosed having at least one atonal-associated nucleic acid sequence replaced by insertion of a heterologous nucleic acid sequence used to detect expression driven by an atonal-associated promoter sequence, wherein the inactivation of the atonal-associated nucleic acid sequence prevents expression of the atonal-associated gene.

8 Claims, 14 Drawing Sheets

OTHER PUBLICATIONS

Brown, Nadean, L., et al.; Math5 encodes a murine basic helix-loop-helix transcription factor expressed during early stages of retinal neurogensis, Development, (Nov. 9, 1998) vol. 125, pp. 4821-4833.

Ho, Alan, et al.; Synthetic Protein Transduction Domains: Enhanced Transduction Potential in Vitro and in Vivo; Cancer Research, vol. 61, pp. 474-477, Jan. 15, 2001.

Jero, Jussi, et al.; A surgical approach appropriate for targeted cochlear gene therapy in the mouse; Hearing Research, vol. 151, pp. 106-114, 2001.

Jero, Jussi, et al.; Cochlear Gene Delivery through an Intact Round Window membrane in Mouse; Human Gene Therapy; vol. 12, pp. 539-548, Mar. 20, 2001.

Lalwani, Anil K., et al.; Expression of Adeno-Associated Virus Integrated Transgene Within the Mammalian Vestibular Organs; Am J Otol 19:390-395, 1998.

Staecker, Hinrich, et al.; Brain-derived neurotropic factor gene therapy prevents spiral ganglion degeneration after hair cell loss; Otolaryngol Head Neck Surg 1998; 119:7-13.

Sherman, Michael P., et al.; HIV-1 Vpr Displays Natural Protein-Transducing Properties: Implications for Viral Pathogenesis; Virology 302, 95-105 (2002).

Ford, K.G., et al.; Protein transduction: an alternative to genetic intervention? Gene Therapy (2001) 8, 1-4.

Morris, May C., et al.; A peptide carrier for the delivery of biologically active proteins into mammalian cells; Nature Biotechnology, vol. 19, pp. 1173-1176, Dec. 2001.

Stöver, Timo, et al.; Cochlear gene transfer: round window versus cochleostomy inoculation; Hearing Research 136 (1999) 124-130.

Zheng JL et al., *Overexpression of Math1 induces robust productio of extra hair cells in postnatal rat inner ears*; Nature Neuroscience, Jun. 2000, pp. 580-586, vol. 3, No. 6, Nature America Inc.

Eberl DF, *Feeling the vibes: chorodotonal mechanisms in insect hearing*, Current Opinion in Neurobiology, 1999, 9 pp.:in press.

Akazawa C et al., *A mammalian helix-loop-helix factor structurally related to the product drosophila proneural gene atonal is a positive transcriptional regulator expressed in the developing nervous system*, The Journal of Biological Chemistry; Apr. 14, 1995, pp. 8730-8738, vol. 270, No. 15, The American Society of Biochemistry & Molecular Biology, Inc.

Sun Y et al., *Transcriptional regulation of atonal during development of the drosphila peripheral nervous system*, Development 125, 1998, pp. 3731-3740, The Company of Biologists Limited, Great Britain.

Jarman AP et al., *Atonal is a proneural gene that directs chordotonal organ formation in the drosophila nervous system*, Cell, Jul. 2, 1993, pp. 1307-1321, vol. 73, Cell Press.

Hassan BA et al., *Doing the math: is the mouse a good model for fly development*? Genes & Development, 2000, pp. 1852-1865, vol. 14, Cold Spring Harbor Laboratory Press.

Hassan BA et al., *Atonal regulates neurite arborization but does not act as a proneural gene in the drosophila brain*, Neuron, Mar. 2000, pp. 549-561, vol. 25, Cell Press.

Ben-Arie N et al., *Math1 is essential for genesis of cerebellar granule neurons*, Nature, Nov. 13, 1997, pp. 169-172, vol. 390.

Bermingham NA et al., *Math1: an essential gene for the generation of inner ear hair cells*, Science, Jun. 11, 1999, pp. 1837-1841, vol. 284, American Assoc. for the Advancement of Science.

Ben-Arie N et al., *Functional conservation of atonal and Math1 in the CNS & PNS*, Development, 2000, pp. 1039-1048, vol. 127, The Company of Biologists Limited, Great Britain.

Ben-Arie N et al., *Evolutionary conservation of sequence & expression of the bHLH protein Atonal suggests a conserved role in neurogenesis*, Human Molecular Genetics, 1996, pp. 1207-1216, vol. 5, Oxford Univ. Press.

Jarman AP et al., *Atonal is the proneural gene for Drosophila photoreceptors*, Nature, Jun. 2, 1994, pp. 398-400, vol. 369.

Kim P et al., *XATH-1, a verterbrate homolog of Drosophila atonal, induces neuronal differentiation within ectodermal progenitors*, Developmental Biology, Article D8978572, 1997, pp. 1-12, vol. 187, Academic Press.

Ben-Arie N et al., *Abnormal cerebellar development in mice lacking the murine homolog of the Drosophila proneural gene atonal*, American J. Human Genetics, 1996, vol. 59, No. 4, Suppl. p. A46, Abstract #232, see abstract.

Sabate O et al., *Adenovirus for Neurodegenerative diseases:* in vivo *strategies* & ex vivo *gene therapy using human neural progenitors*, Clinical Neuroscience, 1996, pp. 317-321, vol. 3, especially p. 317, rt. col., and p. 318, left col.

Williams DP et al., *Structure/Function analysis of Interleukin-2-toxin (DAB486-IL-2), fragment B sequences required for the delivery of fragment A to the cytosol of target cells*, J. Biol. Chem., Jul. 15, 1990, pp. 11885-11887, vol. 265, No. 20.

Chien C-T et al., *Neuronal type information encoded in the basic-helix-loop-helix domain of proneural genes*, Proc. Natl. Acad. Sci. USA, Nov. 1996, pp. 13239-13244, vol. 93, especially pp. 13239-13240.

Kawamoto, K., "Math1 Gene Transfer Generates New Cochlear Hair Cells in Mature Guinea Pigs In Vivo", The Jol. of Neuroscience, (Jun. 1, 2003) 23(11): pp. 4395-4400.

Thibodeau, G.A., et al., "Sense of Hearing and Balance: The Ear, Unit 3, Communication, Control & Integration, Anatomy & Physiology," 4 th Ed., 1999, pp. 454-455, Mosby Inc., St. Louis, MO. USA.

Dooling, R. J., "Recovery of Hearing and Vocal Behavior after Hair-Cell Regeneration," Proc. Natl. Acad. Sci. USA, (Dec. 1997), vol. 94, pp. 14206-14210.

Kanzaki, Sho., "From Gene Identification to Gene Therapy", Audio. Neuro Otology (2002), vol. 7, pp. 161-164.

Kawamoto, K., "The Functional and Structural Outcome of Inner Ear Gene Transfer via the Vestibular and Cochlear Fluids in Mice," Molecular Therapy, (Dec. 2001), vol. 4, No. 6, pp. 575-585.

Jero, J., et al., "A surgical approach appropriate for targeted cochlear gene therapy in the mouse," Hearing Research (2001), pp. 106-114.

Stover, T., et al., "Cochlear gene transfer: round window versus cochleostomy inoculation," Hearing Research (1999), pp. 124-130.

Staecker, H., et al., "Brain-derived neurotrophic factor gene therapy prevents spiral ganglion degeneration after hair cell loss", Otolaryngology, Head and Neck Surgery (Jul. 1998) vol. 119, No. 1, pp. 7-13.

Lalwani, A. K., et al., "Expression of Adeno-Associated Virus Integrated Transgene Within the Mammalian Vestibular Organs," The American Journal of Otology, (1998) vol. 19, pp. 390-395.

Jero, J., et al., "Cochlear Gene Delivery through an Intact Round Window Membrane in Mosue," Human Gene Therapy (Mar. 20, 2001) vol. 12, pp. 539-548.

Shou, J., et al., "Robust generation of new hair cells in the mature mammalian inner ear by adenoviral expression of *Hath 1*", Molecular & Cellular Neuroscience, (2003) vol. 23, pp. 169-179.

Zheng, Lisa J., et al., "Overexpression of *Math1* induces robust production of extra hair cells in postnatal rat inners ears", Nature Neuroscience (2000), vol. 3, No. 6, pp. 580-586.

Carey, John P., et al., "Hair Cell Regeneration and Recovery of the Vestibuloocular Reflex in the Avian Vestibular System," Journal of Neurophysiology (Nov. 1996), vol. 76, No. 5, pp. 3301-3305.

Staecker, Hinrich, et al., "Vestibular Hair Cell Regeneration and Restoration of Balance Function Induced by *Math 1* Gene Transfer," Otology & Neurotology (2007) vol. 28, pp. 223-231.

COMPOSITION AND METHODS FOR THE THERAPEUTIC USE OF AN ATONAL-ASSOCIATED SEQUENCE FOR DEAFNESS, OSTEOARTHRITIS AND ABNORMAL CELL PROLIFERATION

This application is a divisional application of U.S. application Ser. No. 09/585,645, filed Jun. 1, 2000 now U.S. Pat. No. 6,838,444, which claims priority to a provisional application Ser. No. 60/137,060 filed Jun. 1, 1999 and to a second provisional application Ser. No. 60/176,993 filed Jan. 19, 2000, which are all incorporated by reference herein in their entirety.

The work herein was supported by grants from the United States, Government. The United States Government may have certain rights in the invention.

FIELD OF THE INVENTION

The present invention relates in general to the field of genetic diagnosis and therapy and, more particularly, to the characterization and use of an atonal-associated nucleic acid or amino acid sequence, or any of its homologs or orthologs, as a therapeutic agent for the treatment of deafness, partial hearing loss, vestibular defects due to damage or loss inner ear hair cells, osteoarthritis, and abnormal cell proliferation.

BACKGROUND OF THE INVENTION

An intricate pattern of interactions within and between cells directs the sequential development of neurons from dividing neuroepithelial progenitor cells. Multiple extracellular and intracellular signals moderate this process. Among the key intracellular signals are transcription factors, which induce the expression of a cascade of genes. One subclass of transcription factors, belonging to the basic helix-loop-helix (bHLH) family of proteins, is expressed early on when the decision to proliferate or differentiate is made. This function is a particularly crucial one as mutations in these genes early in development can wipe out entire neural structures.

In *Drosophila*, the gene atonal (ato), which is homologous to Math1, Math2, Hath1 and Hath2, encodes a bHLH protein essential for the development of chordotonal organs (sensory organs found in the body wall, joints and antenna that function in proprioception, balance and audition) (Eberl, 1999; McIver, 1985; van Staaden and Römer, 1998). CHOs populate the peripheral nervous system (PNS) in the body wall and joints (thorax, abdomen, sternum, wings, legs) and antennae (Moulins, 1976), providing the fly with sensory information much as touch and mechanoreceptors do in vertebrates (McIver, 1985; Moulins, 1976). Boyan (Boyan, 1993) proposed that, in the course of evolution, different CHOs became specialized for hearing in different insects. This hypothesis was recently confirmed by van Staaden and Römer (1998). In *Drosophila*, CHOs in the Johnston organ, located in the second antennal segment, function in near field hearing (Dreller and Kirschner, 1993; Eberl, 1999) and negative geotaxis.

During development ato is expressed in a cluster of progenitor cells from which the CHO founder cells are selected (Jarman et al., 1993). It likely functions by regulating the expression of genes necessary for the specification and development of the CHO lineage; as it encodes a basic helix-loop-helix protein (bHLH) that dimerizes with the Daughterless protein and binds to E-box sequences, thereby activating genes (Jarman et al., 1993). CHO specificity is encoded by the ato basic domain, which is required for DNA binding in bHLH proteins (Chien et al., 1996; Davis et al., 1990; Jarman and Ahmed, 1998; Vaessin et al., 1990) ato is both necessary and sufficient for the generation of CHOs in the fly: loss of ato function leads to the loss of CHOs, while ectopic ato expression causes ectopic CHO formation (Jarman et al., 1993). Adult flies that lack atonal function are uncoordinated, do not fly, and are deficient in hearing. Overexpression of the fly atonal gene can generate new chordotonal neurons, indicating that atonal is both essential and sufficient for the development of this neuronal population.

In vertebrates, during myogenesis and neurogenesis, cell fate specification requires basis helix-loop-helix (bHLH) transcription factors. Math1 (for mouse atonal homolog-1) is such a factor, and is expressed in the hindbrain, dorsal spinal cord, external germinal layer of the cerebellum, gut, joints, ear and Merkel cells of the skin (which function as mechanoreceptors) (Akazawa et al., 1995; Ben-Arie et al., 1996; Ben-Arie et al., 1997). Mice heterozygous for a targeted deletion of Math1 (Math1$^{+/-}$) are viable and appear normal, but Math1 null mice (Math$^{-/-}$) die shortly after birth and lack cerebellar granule neurons.

Math1 is one of ato's closest known homologs, with 82% amino acid similarity in the bHLH domain and 100% conservation of the basic domain that determines target recognition specificity (Ben-Arie et al., 1996; Chien et al., 1996). Math1 is transiently expressed in the CNS starting at embryonic day 9 (E9) in the dorsal portion of the neural tube. Math1 is also expressed in the rhombic lip of the fourth ventricle of the brain, Where cerebellar granule cell precursors are born at E13-15 (Alder et al., 1996). Upon proliferation and differentiation, these progenitor cells migrate to form the external granule layer (EGL) of the cerebellar primordia (Hatten and Heintz, 1995). Proliferating EGL cells continue to express Math1 during the first three postnatal weeks, until shortly before they migrate to their final adult destination to generate the internal granule layer (IGL) of the cerebellum (Akazawa et al., 1995; Ben-Arie et al., 1996). Another group of cells, a small population of neuronal precursors in the dorsal spinal cord, expresses Math1 during E10-E14 (Akazawa et al., 1995; Ben-Arie et al., 1996). These precursor cells also express the LIM homeodomain proteins (LH2A and LH2B), markers of the D1 class of commissural interneurons (Lee et al., 1998). Helms and Johnson (1998) reported that lacZ expression under the control of Math1 regulatory elements reproduced Math1 expression patterns in the developing cerebellum and spinal cord, and demonstrated that Math1 is expressed in precursors that give rise to a subpopulation of dorsal commissural interneurons.

To determine the in vivo function of Math1, the inventors generated mice (Math1$^{-/-}$) lacking the MATH1 protein. This null mutation causes major cerebellar abnormalities: lack of granule cell proliferation and migration from the rhombic lip at E14.5, and absence of the entire EGL at birth (Ben-Arie et al., 1997). It is not clear whether the agenesis of cerebellar granule neurons is due to failure of progenitor specification or the cells' inability to proliferate and/or differentiate. Neonates cannot breathe and die shortly after birth, but there are no gross defects in any cranial nerves or brain stem nuclei that could explain respiratory failure.

The fact that Math1 is expressed in the inner ear suggests that Math1 expression is necessary for the development of auditory or balance organs. The inner ear initially forms as a thickening of the ectoderm, termed the otic placode, between rhombomeres 5 and 6 in the hindbrain. The otic placode gives rise to neurons of the VIII$^{th}$ cranial nerve and invaginates to become the otocyst, from which the inner ear will develop. The mature mammalian inner ear comprises one auditory organ, the cochlea, and five vestibular organs: the utricle, the saccule, and three semicircular canals. The sensory epithelia of these organs consist of mechanoreceptive hair cells, supporting cells and nerve endings. Hair cells serve as mechanoreceptors for transducing sound waves and head motion into auditory and positional information. Hair cells and supporting cells both arise from a common progenitor cell and proliferate and differentiate within the sensory epithelia, with peak mitoses between embryonic day 13 and 18 (E13-18) in mice. Although several genes have been implicated in the development of the inner ear, such as int2 (Mansour et al., 1993; pax2 (Torres et al., 1996; and Hmx3 (Wang et al., 1998). None have been shown to be required for the genesis of hair cell specifically.

Damage to hair cells is a common cause of deafness and vestibular dysfunction, which are themselves prevalent diseases. Over 28 million Americans have impaired hearing; vestibular disorders affect about one-quarter of the general population, and half of our elderly. The delicate hair cells are vulnerable to disease, aging, and environmental trauma (i.e., antibiotics, toxins, persistent loud noise). Once these cells are destroyed, they cannot regenerate in mammals. Therefore, a need exists to address the problems of patients with congenital, chronic or acquired degenerative hearing impairment and loss or balance problems, and to provide compositions, methods and reagents for use in treating hearing loss and vestibular function.

In support of the teaching of the present invention, others have demonstrated that Math1, upon overexpression, induces significant production of extra hair cells in postnatal rat inner ears (Zheng and Gao, 2000). Briefly, although fate determination is usually completed by birth for mammalian cochlear hair cells, overexpression of Math1 in postnatal rat cochlear explant cultures results in additional ear hair cells which derive from columnar epithelial cells located outside the sensory epithelium in the greater epithelial ridge. Furthermore, conversion of postnatal utricular supporting cells into hair cells is facilitated by Math1 expression. The ability of Math1 to permit production of hair cells in the ear is strong evidence in support of the claimed invention.

SUMMARY OF THE INVENTION

In one embodiment of the present invention there is an animal having a heterologous nucleic acid sequence replacing an allele of an atonal-associated nucleic acid sequence under conditions wherein said heterologous sequence inactivates said allele. In a preferred embodiment said heterologous sequence is expressed under control of an atonal-associated regulatory sequence. In a specific embodiment both atonal-associated alleles are replaced. In an additional specific embodiment both atonal-associated alleles are replaced with nonidentical heterologous nucleic acid sequences. In an additional embodiment said animal has a detectable condition wherein said condition is selected from the group consisting of loss of hair cells, cerebellar granule neuron deficiencies, hearing impairment, imbalance, joint disease, osteoarthritis, abnormal proliferation of neoplastic neuroectodermal cells and formation of medulloblastoma. In another embodiment of the present invention said heterologous nucleic acid sequence is a reporter sequence selected from the group consisting of β-galactosidase, green fluorescent protein (GFP), blue fluorescent protein (BFP), neomycin, kanamycin, luciferase, β-glucuronidase and chloramphenicol transferase (CAT). In another specific embodiment said reporter sequence regulatable or is expressed in brain tissue, neural tissue, skin tissue, non-ossified cartilage cells, joint chondrocytes, Merkel cells, inner ear sensory epithelia and brain stem nuclei. In additional specific embodiments said atonal-associated allele is replaced with an atonal-associated nucleic acid sequence under control of a regulatable promoter sequence or a tissue-specific promoter sequence wherein said tissue is selected from the group consisting of brain tissue, neural tissue, skin tissue, non-ossified cartilage cells, joint chondrocytes, Merkel cells, inner ear sensory epithelia and brain stem nuclei. In additional embodiments said animal is a mouse, *Drosophila*, zebrafish, frog, rat, hamster or guinea pig.

In another embodiment of the present invention is a method for screening for a compound in an animal, wherein said compound affects expression of an atonal-associated nucleic acid sequence comprising delivering said compound to said animal wherein said animal has at least one allele of an atonal-associated nucleic acid sequence inactivated by insertion of a heterologous nucleic acid sequence wherein said heterologous nucleic acid sequence is under control of an atonal-associated regulatory sequence, and monitoring for a change in said expression of said atonal-associated nucleic acid sequence. In specific embodiments said compound upregulates or downregulates said expression of an atonal-associated nucleic acid sequence. In additional embodiments said animal is a mouse or *Drosophila*. In a specific embodiment the heterologous nucleic acid sequence is a reporter sequence. In an additional specific embodiment the heterologous nucleic acid sequence is selected from the group consisting of β-galactosidase, green fluorescent protein (GFP), blue fluorescent protein (BFP), neomycin, kanamycin, luciferase, β-glucuronidase and chloramphenicol transferase (CAT).

Another embodiment of the present invention is a compound which affects expression of an atonal-associated nucleic acid sequence. In specific embodiments said compound upregulates or downregulates expression of an atonal-associated nucleic acid sequence. In a specific embodiment said compound affects a detectable condition in an animal wherein said condition is selected from the group consisting of loss of hair cells, cerebellar granule neuron deficiencies, hearing impairment, an imbalance disorder, joint disease, osteoarthritis, abnormal proliferation of neoplastic neuroectodermal cells and formation of medulloblastoma.

Another embodiment of the present invention is a method for screening for a compound in an animal, wherein said compound affects a detectable condition in said animal, comprising delivering said compound to said animal wherein at least one allele of an atonal-associated nucleic acid sequence in said animal is inactivated by insertion of a heterologous nucleic acid sequence, wherein said heterologous nucleic acid sequence is under the control of an atonal-associated regulatory sequence, and monitoring said animal for a change in the detectable condition. In a specific embodiment said detectable condition is selected from the group consisting of loss of hair cells, cerebellar granule neuron deficiencies, hearing impairment, an imbalance disorder, joint disease, osteoarthritis, abnormal proliferation of neoplastic neuroectodermal cells and formation of medulloblastoma. In another embodiment said delivery of said compound affects expression of said heterologous nucleic acid sequence. In specific embodiments said expression of said heterologous nucleic acid sequence is upregulated or downregulated. In additional specific embodiments said animal is a mouse, *Drosophila*, zebrafish, frog, rat, hamster or guinea pig.

Another embodiment of the present invention is a compound wherein said compound affects said detectable condition. In specific embodiments said compound affects expression of a heterologous nucleic acid sequence. In additional specific embodiments said compound upregulates or downregulates expression of a heterologous nucleic acid sequence.

In other embodiments of the present invention are methods of treating an animal, including a human, for cerebellar granule neuron deficiencies, for promoting mechanoreceptive cell growth, for generating hair cells, for treating hearing impairment or an imbalance disorder, for treating a joint disease, for treating for an abnormal proliferation of cells, and for treating for a disease that is a result of loss of functional atonal-associated nucleic acid or amino acid sequence. Said methods include administering a therapeutically effective amount of an atonal-associated nucleic acid or amino acid sequence. In specific embodiments said administration is by a vector selected from the group consisting of an adenoviral vector, a retroviral vector, an adeno-associated vector, a plasmid, or any other nucleic acid based vector, a liposome, a nucleic acid, a peptide, a lipid, a carbohydrate and a combination thereof of said vectors. In a specific embodiment said vector is a non-viral vector or a viral vector. In another specific embodiment said vector is a cell. In a preferred embodiment said vector is an adenovirus vector comprising a cytomegalovirus IE promoter sequence and a SV40 early polyadenylation signal sequence. In another specific embodiment said cell is a human cell. In an additional specific embodiment said joint disease is osteoarthritis. In a specific embodiment said atonal-associated nucleic acid or amino acid sequence is Hath1 or Math1. In another specific embodiment the cell contains an alteration in an atonal-associated nucleic acid or amino acid sequence. In an additional specific embodiment said amino acid sequence has at least about 80% identity to about 20 contiguous amino acid residues of SEQ ID NO:58. In an additional specific embodiment the nucleic acid sequence encodes a polypeptide which has at least about 80% identity to about 20 contiguous amino acid residues of SEQ ID NO:58.

In another embodiment of the present invention is a method for treating an animal for an abnormal proliferation of cells comprising altering atonal-associated nucleic acid or amino acid sequence levels in a cell. In a specific embodiment said alteration is reduction or said nucleic acid or amino acid sequence contains an alteration.

In another embodiment of the present invention is a composition comprising an atonal-associated amino acid sequence or nucleic acid sequence in combination with a delivery vehicle wherein said vehicle delivers a therapeutically effective amount of an atonal-associated nucleic acid sequence or amino acid sequence into a cell. In specific embodiments said vehicle is the receptor-binding domain of a bacterial toxin or any fusion molecule or is a protein transduction domain. In a specific embodiment said protein transduction domain is from the HIV TAT peptide. In a specific embodiment said atonal-associated amino acid sequence or nucleic acid sequence is Hath1 or Math1.

In another embodiment of the present invention there is a composition to treat an organism for loss of hair cells, wherein said organism comprises a defect in an atonal-associated nucleic acid sequence. In a specific embodiment the defect is a mutation or alteration of said atonal-associated nucleic acid sequence. In another specific embodiment the defect affects a regulatory sequence of said atonal-associated nucleic acid sequence. In an additional embodiment of the present invention there is a composition to treat an organism for loss of hair cells, wherein said organism comprises defect in a nucleic acid sequence which is associated with regulation of an atonal-associated nucleic acid sequence. In an additional embodiment of the present invention there is a composition to treat an organism for loss of hair cells, wherein said organism comprises a defect in an amino acid sequence which is associated with regulation of an atonal-associated nucleic acid sequence.

In another embodiment of the present invention there is a composition to treat an organism for a cerebellar neuron deficiency, wherein said organism comprises a defect in an atonal-associated nucleic acid sequence. In a specific embodiment the defect is a mutation or alteration of said atonal-associated nucleic acid sequence. In another specific embodiment the defect affects a regulatory sequence of said atonal-associated nucleic acid sequence. In an additional embodiment of the present invention there is a composition to treat an organism for a cerebellar neuron deficiency, wherein said organism comprises defect in a nucleic acid sequence which is associated with regulation of an atonal-associated nucleic acid sequence. In an additional embodiment of the present invention there is a composition to treat an organism for a cerebellar neuron deficiency, wherein said organism comprises a defect in an amino acid sequence which is associated with regulation of an atonal-associated nucleic acid sequence.

In another embodiment of the present invention there is a composition to treat an organism for hearing impairment, wherein said organism comprises a defect in an atonal-associated nucleic acid sequence. In a specific embodiment the defect is a mutation or alteration of said atonal-associated nucleic acid sequence. In another specific embodiment the defect affects a regulatory sequence of said atonal-associated nucleic acid sequence. In an additional embodiment of the present invention there is a composition to treat an organism for hearing impairment, wherein said organism comprises defect in a nucleic acid sequence which is associated with regulation of an atonal-associated nucleic acid sequence. In an additional embodiment of the present invention there is a composition to treat an organism for hearing impairment, wherein said organism comprises a defect in an amino acid sequence which is associated with regulation of an atonal-associated nucleic acid sequence.

In another embodiment of the present invention there is a composition to treat an organism for imbalance, wherein said organism comprises a defect in an atonal-associated nucleic acid sequence. In a specific embodiment the defect is a mutation or alteration of said atonal-associated nucleic acid sequence. In another specific embodiment the defect affects a regulatory sequence of said atonal-associated nucleic acid sequence. In an additional embodiment of the present invention there is a composition to treat an organism for imbalance, wherein said organism comprises defect in a nucleic acid sequence which is associated with regulation of an atonal-associated nucleic acid sequence. In an additional embodiment of the present invention there is a composition to treat an organism for imbalance, wherein said organism comprises a defect in an amino acid sequence which is associated with regulation of an atonal-associated nucleic acid sequence.

In another embodiment of the present invention there is a composition to treat an organism for osteoarthritis, wherein said organism comprises a defect in an atonal-associated nucleic acid sequence. In a specific embodiment the defect is a mutation or alteration of said atonal-associated nucleic acid sequence. In another specific embodiment the defect affects a regulatory sequence of said atonal-associated nucleic acid sequence. In an additional embodiment of the present invention there is a composition to treat an organism for osteoarthritis, wherein said organism comprises defect in a nucleic acid sequence which is associated with regulation of an atonal-associated nucleic acid sequence. In an additional embodiment of the present invention there is a composition to treat an organism for osteoarthritis, wherein said organism comprises a defect in an amino acid sequence which is associated with regulation of an atonal-associated nucleic acid sequence.

In another embodiment of the present invention there is a composition to treat an organism for a joint disease, wherein said organism comprises a defect in an atonal-associated nucleic acid sequence. In a specific embodiment the defect is a mutation or alteration of said atonal-associated nucleic acid sequence. In another specific embodiment the defect affects a regulatory sequence of said atonal-associated nucleic acid sequence. In an additional embodiment of the present invention there is a composition to treat an organism for a joint disease, wherein said organism comprises defect in a nucleic acid sequence which is associated with regulation of an atonal-associated nucleic acid sequence. In an additional embodiment of the present invention there is a composition to treat an organism for a joint disease, wherein said organism comprises a defect in an amino acid sequence which is associated with regulation of an atonal-associated nucleic acid sequence.

In another embodiment of the present invention there is a composition to treat an organism for abnormal proliferation of cells, wherein said organism comprises a defect in an atonal-associated nucleic acid sequence. In a specific embodiment the defect is a mutation or alteration of said atonal-associated nucleic acid sequence. In another specific embodiment the defect affects a regulatory sequence of said atonal-associated nucleic acid sequence. In an additional embodiment of the present invention there is a composition to treat an organism for abnormal proliferation of cells, wherein said organism comprises defect in a nucleic acid sequence which is associated with regulation of an atonal-associated nucleic acid sequence. In an additional embodiment of the present invention there is a composition to treat an organism for abnormal proliferation of cells, wherein said organism comprises a defect in an amino acid sequence which is associated with regulation of an atonal-associated nucleic acid sequence.

In another embodiment of the present invention there is a composition to treat an organism for cancer, wherein said organism comprises a defect in an atonal-associated nucleic acid sequence. In a specific embodiment the defect is a mutation or alteration of said atonal-associated nucleic acid sequence. In another specific embodiment the defect affects a regulatory sequence of said atonal-associated nucleic acid sequence. In an additional embodiment of the present invention there is a composition to treat an organism for cancer, wherein said organism comprises defect in a nucleic acid sequence which is associated with regulation of an atonal-associated nucleic acid sequence. In an additional embodiment of the present invention there is a composition to treat an organism for cancer, wherein said organism comprises a defect in an amino acid sequence which is associated with regulation of an atonal-associated nucleic acid sequence. In a specific embodiment said cancer is medulloblastoma.

Other and further objects, features and advantages would be apparent and eventually more readily understood by reading the following specification and by reference to the company drawing forming a part thereof, or any examples of the presently preferred embodiments of the invention are given for the purpose of the disclosure.

DESCRIPTION OF THE DRAWINGS

FIG. 1A shows the otic vesicle (OV) at E12.5 and FIG. 1B the inner ear at E14.5 of Math1$^{+/\beta-Gal}$ embryos. Sensory epithelia stained positively in the cochlea (C), saccule (S), utricle (U), and semicircular canal ampullae (SCA). A schematic diagram of the inner ear is depicted alongside the staining for reference, blue indicates location of the sensory epithelia. The original magnifications of the images taken under the microscope were ×100 For FIG. 1A and ×50 for FIG. 1B.

FIG. 4A shows that the hair cells (HC) and supporting cells (SC) are present in wild-type utricular macula. By contrast, only supporting cells are present in the null mouse (FIG. 4B). Hair cells have hair bundles (HB) and supporting cells have miicrovilli (MV). Hair cells are less electron-dense and have more apical nuclei than supporting cells, but only the latter have secretory granules (SG). Some immature hair cells (IM) are evident in the wild-type, but not in the null mouse. The scale bar in all the figures equals 10 μm.

FIG. 6A shows the staining pattern of a P14 mouse forelimb and demonstrates expression in all joints. FIG. 6B is a magnification (20×) of an elbow joint from the same mouse that demonstrates that Math1 is expressed exclusively in the non-ossified articular chondrocytes.

FIG. 7A, Top, has a map of the Math1 genomic locus. The coding region is shown as a black box. The sites of the probes used to detect the wild-type and mutant alleles are shown as black bars. The targeting vector is in the middle with the sites for homologous recombination indicated by larger Xs. In the targeted locus shown at the bottom, lacZ is translated under the control of Math1 regulatory elements. FIG. 7B demonstrates Southern blot analysis of embryonic stem cells using the 3' external probe. The upper band represents wt allele and the lower band the targeted mutant allele (mut) in targeted clones. FIG. 7C demonstrates Southern blot analysis of DNA from the progeny of heterozygous mice demonstrating the presence of the targeted allele and absence of the wild-type allele in Math1$^{b\text{-}gal/b\text{-}gal}$ mice. (asterisks). The abbreviations are as follows: (A) ApaI; (H) HindIII; (RI) EcoRI; (S) SalI; and (X) XbaI.

FIG. 8A shows Math1/lacZ expression in the dorsal neural tube at E9.5 and (FIG. 8B) E10.5. FIG. 8C indicates a section through the hind brain at E10.5 has Math1/lacZ expression in the dorsal portion (arrows). FIG. 8D demonstrates that in a spinal cord section from E12.5 embryo, dorsal cells migrate ventrally (arrows). FIG. 8E shows at E14.5 expression is observed in the EGL progenitors at the rhombic lip and in migrating cells that will populate the EGL. FIG. 8F demonstrates in Math1$^{b\text{-}gal/b\text{-}gal}$ mice, Math1/lacZ expression is limited to a few cells in the rhombic lip, which is significantly reduced in size. FIG. 8G shows that at P0 Math1/lacZ is expressed in the EGL. FIG. 8H demonstrates that the EGL is absent in the null mice. Original magnification for FIGS. 8C through 8H was 100×.

FIGS. 9F and 9G show haematoxylin and eosin staining of sagittal sections through the pons of a wild type and null mutant (FIGS. 9F and 9G, respectively), showing the loss of the ventral pontine nucleus in null mutants. The original magnifications were as follows: (A) 400× (B & C) 1000×, (D & E) 8×, inset in D & E 100×, (F & G) 10×.

FIG. 10D shows a horizontal section through a humero-radial joint at P10 that has expression in the articular chondrocytes (arrowhead) and resting chondrocytes (arrow). FIG. 10E shows high magnification of a section through a wrist joint indicating Math1/lacZ is expressed in articular chondrocytes. The original magnification is was follows: (C) 10×; (D) 20×; and (E) 40×.

FIG. 14A shows a dorsal view of the thorax of a wild-type fly. Note there are regular array of bristles or macrochaetae. FIG. 14B shows a similar view of a transgenic fly in which Math1 was overexpressed using the UAS/GAL4 system (Brand and Perrimon, 1993). This ectopic expression leads to numerous extra bristles that are external sensory organs (another type of mechano receptor), not CHOs. Ectopic CHOs were produced in many other regions. FIG. 14C shows a lateral view of two abdominal clusters containing 6 CHOs in addition to external sensory organs, revealed by a neuronal-specific antibody (Mab 22C10). The 5 lateral CHOs form a cluster, and the sixth is dorsal to the cluster. FIG. 14D shows a similar view of an ato mutant embryo showing lack of the CHOs. FIG. 14E demonstrates ubiquitous expression of Math1 induces new CHO neurons in ato mutant embryos in the proper location. FIG. 14F shows in situ hybridization of whole mount third instar brain using the ato cDNA as a probe. Note expression in the developing optic lobes ("horse shoe" expression patterns) and two punctate clusters of cells in the middle of the brain lobes (arrow heads). FIG. 14G shows Math1 expression in *Drosophila* induces CHO formation in normal and ectopic locations. The (+) indicates presence of CHOs and (−) indicates their absence. Number of (+) in the first column is used to quantify the relative increase in the number of CHOs observed when Math1 is expressed.

DETAILED DESCRIPTION OF THE INVENTION

Figure 1:
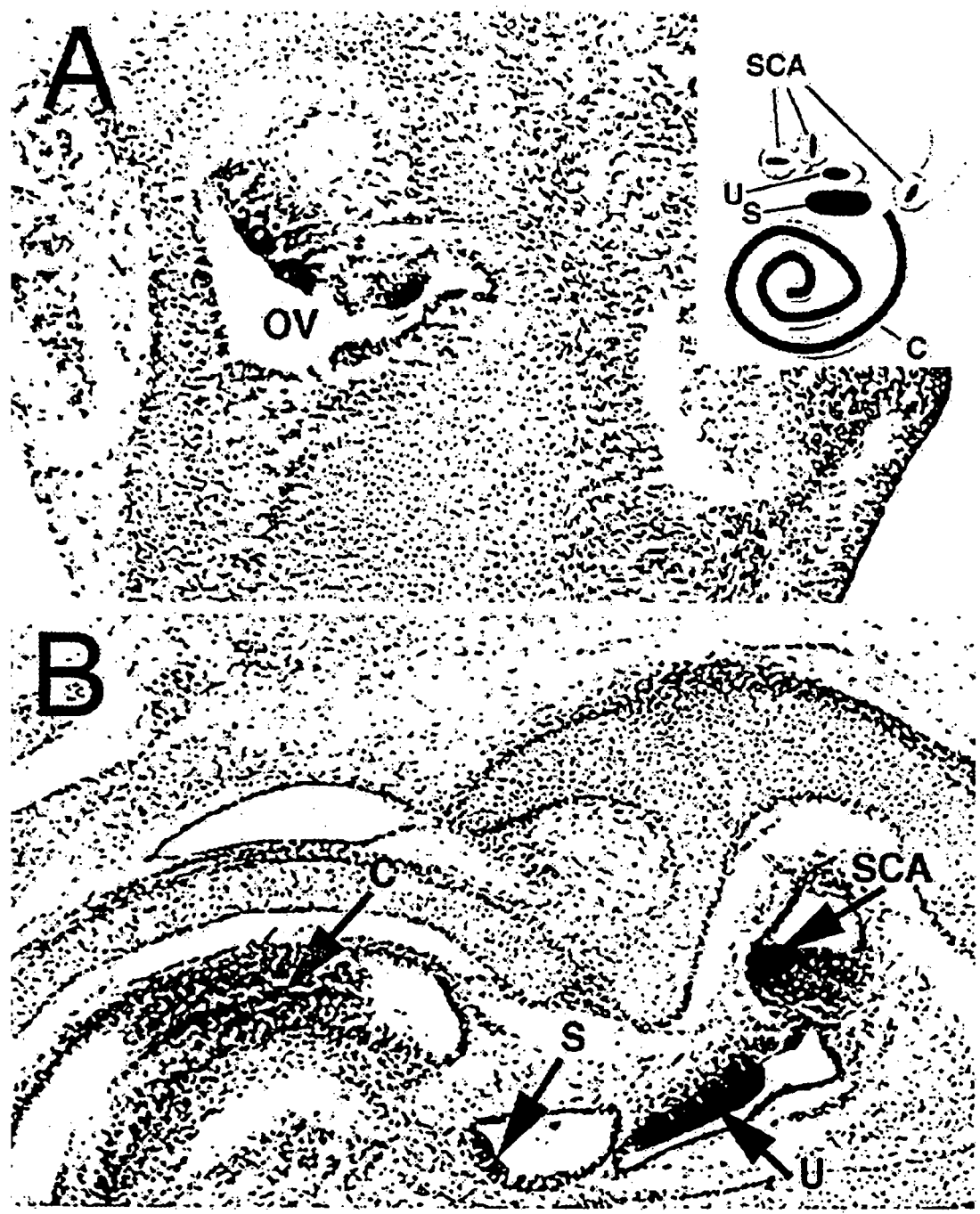
FIGS. 1A and 1B demonstrate that the inner ear β-Gal staining (blue) of Math1 heterozygous embryos as described hereinabove.

It is readily apparent to one skilled in the art that various embodiments and modifications can be made to the invention disclosed in this Application without departing from the scope and spirit of the invention.

The term "abnormal proliferation" as used herein is defined as any proliferation of any type of cell, wherein said cell is not under the constraints of normal cell cycle progression and wherein said proliferation can result in a tumor or any cancerous development.

The term "alteration" as used herein is defined as any type of change or modification to a nucleic acid or amino acid. Said change or modification includes any mutation, deletion, rearrangment, addition to a nucleic acid. This includes posttranscriptional processing such as addition of a 5' cap, intron processing and polyadenylation. Mutations can be nonsense, missense, frameshift, or could lead to a truncated amino acid or could alter the conformation of the amino acid. The alteration to a nucleic acid can be present in regulatory sequences or can affect trans-acting factors. Also, multiple alterations can be present. Said change or modification also includes any change to an amino acid including methylation, myristilation, acetylation, glycosylation, or a change to signals associated with processing of said amino acid including intracellular or intercellular localization signals and cleaving of extraneous amino acids. Said alteration can also affect degradation or folding of said protein.

The term "atonal-associated" as used herein is defined as any nucleic acid sequence or amino acid sequence which is the *Drosophila* atonal nucleic acid sequence or amino acid sequence, or is any sequence which is homologous to or has significant sequence similarity to said nucleic acid or amino acid sequence, respectively. The sequence can be present in any animal including mammals and insects. As used herein, significant sequence similarity means similarity is greater than 25% and can occur in any region of another sequence. Examples of atonal-associated include but are not limited to Math1 (mouse atonal homolog 1), Cath1 (chicken atonal homolog 1), Hath1 (human atonal homolog 1), and Xath1 (*Xenopus* atonal homolog 1). Furthermore, multiple homologous or similar sequences can exist in an animal.

The term "cerebellar granule neuron deficiencies" as used herein is defined as any deficiency associated with cerebellar granule neurons and can include loss of cerebellar granule neurons, cerebellar granule neuron precursor cells, lack of granule cell proliferation, lack of granule cell migration and lack of cerebellar external granule layer cells.

The term "defect" as used herein is defined as an alteration, mutation, flaw or loss of expression of an atonal-associated sequence. A skilled artisan is aware that loss of expression concerns expression levels of an atonal-associated sequence which are not significant or detectable by standard means in the art. A skilled artisan is also aware that loss, or absence, of expression levels in an adult organism, such as a human, occurs naturally and leads to impairment of hearing over time. Thus, "defect" as used herein includes the natural reduction or loss of expression of an atonal-associated sequence.

The term "delivering" as used herein is defined as bringing to a destination and includes administering, as for a therapeutic purpose.

The term "delivery vehicle" as used herein is defined as an entity which is associated with transfer of another entity. Said delivery vehicle is selected from the group consisting of an adenoviral vector, a retroviral vector, an adeno-associated vector, a plasmid, a liposome, a nucleic acid, a peptide, a lipid, a carbohydrate and a combination thereof.

The term "detectable condition" as used herein is defined as any state of health or status of an animal, organ or tissue characterized by specific developmental or pathological symptoms. Examples include but are not limited to loss of hair cells, cerebellar granule neuron deficiencies, hearing impairment, imbalance, joint disease, osteoarthritis, abnormal proliferation of neoplastic neuroectodermal cells and formation of medulloblastoma The term "heterologous" as used herein is defined as nucleic acid sequence which is of or relating to nucleic acid sequence not naturally occurring in a particular locus. In an alternative embodiment, the heterologous nucleic acid sequence naturally occurs in a particular locus, but contains a molecular alteration compared to the naturally occurring locus. For instance, a wild-type locus of an atonal-associated sequence can be used to replace a defective copy of the same sequence.

The term "imbalance disorder" as used herein is defined as a medical condition wherein an organism has impaired balance. In a specific embodiment the impairment is due to a defect of vestibular origin. In another specific embodiment the disorder is a vestibular disorder of balance perception including but not limited to Meniere disease, vertigo and layrinthitis.

The term "inactivated" as used herein is defined as a state in which expression of a nucleic acid sequence is reduced or completely eliminated. Said inactivation can occur by transfer or insertion of another nucleic acid sequence or by any means standard in the art to affect expression levels of a nucleic acid sequence.

The term "precursors" as used herein is defined as progenitor cells from which other cells derive their origin and/or properties.

The term "regulatable reporter sequence" as used herein is defined as any sequence which directs transcription of another sequence and which itself is under regulatory control by an extrinsic factor or state. Examples of extrinsic factors or states include but are not limited to exposure to chemicals, nucleic acids, proteins, peptides, lipids, carbohydrates, sugars, light, sound, hormones, touch, or tissue-specific milieu. Examples of regulatable reporter sequences include the GAL promoter sequence and the tetracycline promoter/transactivator sequence.

The term "regulatory sequence" as used herein is defined as any sequence which controls either directly or indirectly the transcription of another sequence. Said control can be either regarding the initiation or cessation of transcription or regarding quantity or tissue distribution of transcription.

The term "reporter sequence" as used herein is defined as any sequence which demonstrates expression by a regulatory sequence. Said reporter sequence can be used as a marker in the form of an RNA or in a protein. Examples of reporter sequences are b-galactosidase, green fluorescent protein (GFP), blue fluorescent protein (BFP), neomycin, kanamycin, luciferase, b-glucuronidase and chloramphenicol transferase (CAT). In a specific aspect of the present invention, the presence and quantity of the reporter sequence product, whether it be a nucleic acid or amino acid, reflects the level of transcription by the promoter sequence which regulates it.

The term "therapeutically effective" as used herein is defined as the amount of a compound required to improve some symptom associated with a disease. For example, in the treatment of hearing impairment, a compound which improves hearing to any degree or arrests any symptom of hearing impairment would be therapeutically effective. In the treatment of a joint disease, a compound which improves the health or movement of a joint to any degree or arrests any symptom of a joint disease would be therapeutically effective. In the treatment of abnormal proliferation of cells, a compound which reduces the proliferation would be therapeutically effective. In the treatment of cancer, a compound which reduces proliferation of the cells, reduces tumor size, reduces metastases, reduces proliferation of blood vessels to said cancer, facilitates an immune response against the cancer would be therapeutically effective, for example. A therapeutically effective amount of a compound is not required to cure a disease but will provide a treatment for a disease.

The term "vector" as used herein is defined as a biological vehicle for delivery of a specific entity. In a specific embodiment the entity is an atonal-associated nucleic acid.

In one aspect of the present invention there are methods and reagents which include utilization of an atonal-associated nucleic acid or amino acid sequence for the therapeutic use of detectible conditions such as loss of hair cells, cerebellar granule neuron deficiencies, hearing impairment, an imbalance disorder, joint disease, osteoarthritis, abnormal proliferation of neoplastic neuroectodermal cells and formation of medulloblastoma. Thus, any homolog or ortholog of atonal (from *Drosophila*) including but not limited to Cath1 (from chicken), Hath1 (from human), Math1 (from mice) or Xath1 (from *Xenopus*) can be used in the present invention. In a preferred embodiment these sequences are directed to treatment of an animal, specifically a human, for the detectable conditions stated above. It is within the scope of the invention to encompass any sequence which is homologous to or has significant sequence similarity to said nucleic acid or amino acid sequence, respectively. The sequence can be present in any animal including mammals and insects. As used herein, significant sequence similarity means similarity (identity of amino acid residues or nucleic acid bases) is greater than 25% and can occur in any region of the sequence. In another embodiment an atonal-associated sequence as used herein has greater than about 50% sequence similarity, greater than about 70% similarity, or greater than about 80% similarity.

It is within the scope of the present invention that an atonal-associated nucleic acid sequence or amino acid sequence is utilized wherein domains important for activity, such as the basic HLH region, are included in a molecule but further comprise alterations, mutations, deletions or substitutions in regions of the nucleic acid or amino acid sequence which are not part of a domain important for an activity and do not affect its function.

Examples of atonal-associated include but are not limited to Math1 (mouse atonal homolog 1), Cath1 (chicken atonal homolog 1), Hath1 (human atonal homolog 1), and Xath1 (*Xenopus* atonal homolog 1). Such examples are represented in SEQ ID NO:1 through SEQ ID NO:66, although others very likely exist in related organisms. A skilled artisan is cognizant of means to identify such sequences which have significant similarity, such as searching database collections of nucleic and amino acid sequence located on the World Wide Web.

The sequences provided herein and the corresponding GenBank Accession numbers are listed parenthetically as follows: SEQ ID NO:1 (NM_005172); SEQ ID NO:2 (NP_005163.1); SEQ ID NO:3 (AW413228); SEQ ID NO: 4 (NM_009719); SEQ ID NO:5 (NP_033849.1); SEQ ID NO:6 (NM_009718);.SEQ ID NO: 7 (NP_033848.1) SEQ ID NO:8 (NM_009717); SEQ ID NO: 9 (NP_033847.1); SEQ ID NO:10 (NM_007500); SEQ ID NO: 11(NP_031526.1); SEQ ID NO:12 (NM_007501); SEQ ID NO:13 (AW280518); SEQ ID NO:14(AW236965); SEQ ID NO:15 (AW163683); SEQ ID NO:16 (AF134869); SEQ ID NO: 17(AAD31451.1); SEQ ID NO:18 (AJ012660); SEQ ID NO:19 (CAA10106.1); SEQ ID NO:20 (AJ012659); SEQ ID NO:21 (CAA10105.1); SEQ ID NO:22 (AF071223); SEQ ID NO:23 (AAC68868.1); SEQ ID NO:24 (U76208); SEQ ID NO:25 (AAC53029.1); SEQ ID NO:26 (U76210); SEQ ID NO:27 (AAC53033.1); SEQ ID NO:28 (I76209); SEQ ID NO:29 (AAC53032.1); SEQ ID NO:30 (U76207); SEQ ID NO:31 (AAC53028.1); SEQ ID NO:32 (AF036257); SEQ ID NO:33 (AAC15969.1); SEQ ID NO:34 (AF034778); SEQ ID NO:35 (AJ001178); SEQ ID NO:36 (CAA04572.1); SEQ ID NO:37 (Y07621); SEQ ID NO:38 (CAA68900.1); SEQ ID NO:39 (AF024536); SEQ ID NO:40 (AAB82272.1); SEQ ID NO:41 (D85188); SEQ ID NO:42 (BAA12738.1); SEQ ID NO:43 (D44480); SEQ ID NO:44(BAA07923.1); SEQ ID NO:45 (D43694); SEQ ID NO:46 (BAA07791.1); SEQ ID NO:47 (D85845); SEQ ID NO:48 (BAA12880.1); SEQ ID NO:49 (U93171); SEQ ID NO:50 (AAB58669.1); SEQ ID NO:51 (U93170); SEQ ID NO:52 (AAB58668.1); SEQ ID NO:53 (U61152); SEQ ID NO:54 (AAB41307.1); SEQ ID NO:55 (U61151); SEQ ID NO:56 (AAB41306.1); SEQ ID NO:57 (U61148); SEQ ID NO:58 (AAB41305.1); SEQ ID NO:59 (U61149); SEQ ID NO:60 (AAB41304.1); SEQ ID NO:61 (U61150); SEQ ID NO:62 (AAB41303.1); SEQ ID NO:63 (L36646); and SEQ ID NO:64 (AAA21879.1).

In an aspect of the invention there is an animal having a heterologous nucleic acid sequence replacing an allele of an atonal-associated nucleic acid sequence under conditions wherein said heterologous sequence inactivates said allele. In an alternative embodiment a heterologous sequence is delivered to a cell for extrachromosomal propagation. In another alternative embodiment a heterologous sequence is integrated into the chromosome of a cell in a locus other than the locus of an atonal-associated nucleic acid sequence. In a preferred embodiment said heterologous sequence is expressed under control of an atonal-associated regulatory sequence. In a specific embodiment both atonal-associated alleles are replaced. In an additional specific embodiment both atonal-associated alleles are replaced with nonidentical heterologous nucleic acid sequences. Methods to generate transgenic animals are well known in the art, and a skilled artisan would refer to such references as *Transgenic Animals* by Grosveld and Kollias (eds.) or *Mouse Genetics and Transgenics: A Practical Approach* by Jackson et al. (eds.).

In an additional embodiment a transgenic animal of the present invention has a detectable condition wherein said condition is selected from the group consisting of loss of hair cells, cerebellar granule neuron deficiencies, hearing impairment, an imbalance disorder, joint disease, osteoarthritis and abnormal proliferation of cells. In another embodiment of the present invention a heterologous nucleic acid sequence is a reporter sequence selected from the group consisting of β-galactosidase, green fluorescent protein (GFP), blue fluorescent protein (BFP), neomycin, kanamycin, luciferase, β-glucuronidase and chloramphenicol transferase (CAT). In another specific embodiment, a reporter sequence is regulatable or is expressed in brain tissue, neural tissue, skin tissue, non-ossified cartilage cells, joint chondrocytes, Merkel cells, inner ear epithelial cells and brain stem nuclei. In additional specific embodiments said atonal-associated allele is replaced with an atonal-associated nucleic acid sequence under control of a regulatable promoter sequence or a tissue-specific promoter sequence wherein said tissue is selected from the group consisting of brain tissue, neural tissue, skin tissue, non-ossified cartilage cells, joint chondrocytes, Merkel cells, inner ear epithelial cells and brain stem nuclei. In additional embodiments a transgenic animal is a mouse, Drosophila, frog, zebrafish, rat, guinea pig, or hamster.

In another embodiment of the present invention is a method for screening for a compound in an animal, wherein said compound affects expression of an atonal-associated nucleic acid sequence comprising delivering said compound to said animal wherein said animal has at least one allele of an atonal-associated nucleic acid sequence inactivated by insertion of a heterologous nucleic acid sequence wherein said heterologous nucleic acid sequence is under control of an atonal-associated regulatory sequence, and monitoring for a change in said expression of said atonal-associated nucleic acid sequence. Examples of regulatory sequences can include promoter sequences, enhancers or silencers.

In specific embodiments there is a compound which upregulates or downregulates said expression of an atonal-associated nucleic acid sequence. The upregulation or downregulation can be by increasing the rate of transcription or decreasing the rate of mRNA decay.

Another embodiment of the present invention is a compound which affects expression of an atonal-associated nucleic acid sequence. In specific embodiments said compound upregulates or downregulates expression of an atonal-associated nucleic acid sequence. In a specific embodiment said compound affects a detectable condition in an animal wherein said condition is selected from the group consisting of loss of hair cells, cerebellar granule neuron deficiencies, hearing impairment, an imbalance disorder, joint disease, osteoarthritis, abnormal proliferation of cells and formation of cancer.

Another embodiment of the present invention is a method for screening for a compound in an animal, wherein the compound affects a detectable condition in the animal, comprising delivering the compound to the animal wherein at least one allele of an atonal-associated nucleic acid sequence in said animal is inactivated by insertion of a heterologous nucleic acid sequence, wherein said heterologous nucleic acid sequence is under the control of an atonal-associated regulatory sequence, and monitoring said animal for a change in the detectable condition. In a specific embodiment said detectable condition is selected from the group consisting of loss of hair cells, cerebellar granule neuron deficiencies, hearing impairment, an imbalance disorder, joint disease, osteoarthritis and abnormal proliferation of cells. In another embodiment said delivery of said compound affects expression of said heterologous nucleic acid sequence. In specific, embodiments said expression of said heterologous nucleic acid sequence is upregulated or downregulated. In additional specific embodiments the animal is a mouse, Drosophila, frog, zebrafish, rat, hamster and guinea pig.

Another embodiment of the present invention is a compound wherein said compound affects a detectable condition in a transgenic animal of the present invention. In specific embodiments said compound affects expression of a heterologous nucleic acid sequence. In additional specific embodiments said compound upregulates or downregulates expression of a heterologous nucleic acid sequence.

In other embodiments of the present invention are methods of treating an animal, including a human, for cerebellar granule neuron deficiencies, for promoting mechanoreceptive cell growth, for generating hair cells, for treating hearing impairment or an imbalance disorder, for treating a joint disease, for treating for an abnormal proliferation of cells, and for treating for a disease that is a result of loss of functional atonal-associated nucleic acid or amino acid sequence. Said methods include administering a therapeutically effective amount of an atonal-associated nucleic acid or amino acid sequence. In specific embodiments said administration is by a vector selected from the group consisting of a viral vector (including bacteriophage, animal and plant viruses), a plasmid, cosmid or any other nucleic acid based vector, a liposome, a nucleic acid, a peptide, a lipid, a carbohydrate and a combination thereof of said vectors. In a specific embodiment said viral vector is an adenovirus vector, a retrovirus vector, or an adeno-associated vector, including a lentivirus vector, Herpes virus vector, alpha virus vector, etc. Thus, a vector can be viral or non-viral. In another specific embodiment said vector is a cell. In a preferred embodiment said vector is an adenovirus vector comprising a cytomegalovirus IE promoter sequence and a SV40 early polyadenylation signal sequence. In another specific embodiment said cell is a human cell. In an additional specific embodiment said joint disease is osteoarthritis.

In an embodiment of the present invention there is provided a method for treating an organism for a disease that is a result of loss of functional atonal-associated nucleic acid or amino acid sequence. A skilled artisan is aware that this loss can be due to natural reduction or absence of significant (or to detectable levels) expression which occurs in an adult human.

In a specific embodiment, the present invention also provides a method of treating an animal in need of treatment for a deficiency in cerebellar granule neurons, a hearing impairment, an imbalance disorder, a joint disease, or in need of promoting mechanoreceptive cell growth, or a disease that is a result of loss of functional atonal-associated nucleic acid or amino acid sequences. This method comprises delivering a transcription factor having an amino acid with at least about 70% identity, preferably at least about 80% identity, and more preferably at least about 90% identity to the sequence AANARERRRMHGLNHAFDQLR (SEQ ID NO:70) to a cell in the animal. In some embodiments, the cell in the animal is located in the inner ear of the animal. Preferably, the transcription factor competes with atonal for binding to Daughterless protein (Jarman et al., 1993) or competes for binding with Math-1 to E47 protein (Akazawa et al., 1995).

In another embodiment of the present invention is a method for treating an animal for an abnormal proliferation of cells comprising altering atonal-associated nucleic acid or amino acid sequence levels in a cell. In a specific embodiment said alteration is reduction or said nucleic acid or amino acid sequence contains an alteration.

In a preferred embodiment of the present invention there are compositions to treat an organism for various medical conditions, discussed herein, comprising an atonal-associated nucleic acid sequence or amino acid sequence in combination with a delivery vehicle, wherein said organism comprises a defect in an atonal-associated nucleic acid sequence. A skilled artisan is aware that an adult organism, such as an adult human, naturally does not express atonal to significant or detectable levels, but instead expresses atonal in an embryonic stage of development (see the Examples). Thus, in a preferred embodiment, compositions to treat an organism as discussed herein, include compositions to treat organisms who do not contain a mutation in an atonal nucleic acid or amino acid sequence but who naturally have atonal no longer expressed to significant or detectable levels.

In another embodiment of the present invention is a composition comprising an atonal-associated amino acid sequence or nucleic acid sequence in combination with a delivery vehicle wherein said vehicle delivers a therapeutically effective amount of an atonal-associated nucleic acid sequence or amino acid sequence into a cell. In specific embodiments said vehicle is the receptor-binding domain of a bacterial toxin or any fusion molecule or is a protein transduction domain. In a specific embodiment said protein transduction domain is from the HIV TAT peptide.

In another embodiment of the present invention there is a composition to treat an organism for loss of hair cells, wherein said organism comprises a defect in an atonal-associated nucleic acid sequence. In a specific embodiment the defect is a mutation or alteration of said atonal-associated nucleic acid sequence. In another specific embodiment the defect affects a regulatory sequence of said atonal-associated nucleic acid sequence. In an additional embodiment of the present invention there is a composition to treat an organism for loss of hair cells, wherein said organism comprises defect in a nucleic acid sequence which is associated with regulation of an atonal-associated nucleic acid sequence. In an additional embodiment of the present invention there is a composition to treat an organism for loss of hair cells, wherein said organism comprises a defect in an amino acid sequence which is associated with regulation of an atonal-associated nucleic acid sequence.

In another embodiment of the present invention there is a composition to treat an organism for a cerebellar neuron deficiency, wherein said organism comprises a defect in an atonal-associated nucleic acid sequence. In a specific embodiment the defect is a mutation or alteration of said atonal-associated nucleic acid sequence. In another specific embodiment the defect affects a regulatory sequence of said atonal-associated nucleic acid sequence. In an additional embodiment of the present invention there is a composition to treat an organism for a cerebellar neuron deficiency, wherein said organism comprises defect in a nucleic acid sequence which is associated with regulation of an atonal-associated nucleic acid sequence. In an additional embodiment of the present invention there is a composition to treat an organism for a cerebellar neuron deficiency, wherein said organism comprises a defect in an amino acid sequence which is associated with regulation of an atonal-associated nucleic acid sequence.

In another embodiment of the present invention there is a composition to treat an organism for hearing impairment, wherein said organism comprises a defect in an atonal-associated nucleic acid sequence. In a specific embodiment the defect is a mutation or alteration of said atonal-associated nucleic acid sequence. In another specific embodiment the defect affects a regulatory sequence of said atonal-associated nucleic acid sequence. In an additional embodiment of the present invention there is a composition to treat an organism for hearing impairment, wherein said organism comprises defect in a nucleic acid sequence which is associated with regulation of an atonal-associated nucleic acid sequence. In an additional embodiment of the present invention there is a composition to treat an organism for hearing impairment, wherein said organism comprises a defect in an amino acid sequence which is associated with regulation of an atonal-associated nucleic acid sequence.

In another embodiment of the present invention there is a composition to treat an organism for an imbalance disorder, wherein said organism comprises a defect in an atonal-associated nucleic acid sequence. In a specific embodiment the defect is a mutation or alteration of said atonal-associated nucleic acid sequence. In another specific embodiment the defect affects a regulatory sequence of said atonal-associated nucleic acid sequence. In an additional embodiment of the present invention there is a composition to treat an organism for an imbalance disorder, wherein said organism comprises defect in a nucleic acid sequence which is associated with regulation of an atonal-associated nucleic acid sequence. In an additional embodiment of the present invention there is a composition to treat an organism for an imbalance disorder, wherein said organism comprises a defect in an amino acid sequence which is associated with regulation of an atonal-associated nucleic acid sequence.

In another embodiment of the present invention there is a composition to treat an organism for osteoarthritis, wherein said organism comprises a defect in an atonal-associated nucleic acid sequence. In a specific embodiment the defect is a mutation or alteration of said atonal-associated nucleic acid sequence. In another specific embodiment the defect affects a regulatory sequence of said atonal-associated nucleic acid sequence. In an additional embodiment of the present invention there is a composition to treat an organism for osteoarthritis, wherein said organism comprises defect in a nucleic acid sequence which is associated with regulation of an atonal-associated nucleic acid sequence. In an additional embodiment of the present invention there is a composition to treat an organism for osteoarthritis, wherein said organism comprises a defect in an amino acid sequence which is associated with regulation of an atonal-associated nucleic acid sequence.

In another embodiment of the present invention there is a composition to treat an organism for a joint disease, wherein said organism comprises a defect in an atonal-associated nucleic acid sequence. In a specific embodiment the defect is a mutation or alteration of said atonal-associated nucleic acid sequence. In another specific embodiment the defect affects a regulatory sequence of said atonal-associated nucleic acid sequence. In an additional embodiment of the present invention there is a composition to treat an organism for a joint disease, wherein said organism comprises defect in a nucleic acid sequence which is associated with regulation of an atonal-associated nucleic acid sequence. In an additional embodiment of the present invention there is a composition to treat an organism for a joint disease, wherein said organism comprises a defect in an amino acid sequence which is associated with regulation of an atonal-associated nucleic acid sequence.

In another embodiment of the present invention there is a composition to treat an organism for abnormal proliferation of cells, wherein said organism comprises a defect in an atonal-associated nucleic acid sequence. In a specific embodiment the defect is a mutation or alteration of said atonal-associated nucleic acid sequence. In another specific embodiment the defect affects a regulatory sequence of said atonal-associated nucleic acid sequence. In an additional embodiment of the present invention there is a composition to treat an organism for abnormal proliferation of cells, wherein said organism comprises defect in a nucleic acid sequence which is associated with regulation of an atonal-associated nucleic acid sequence. In an additional embodiment of the present invention there is a composition to treat an organism for abnormal proliferation of cells, wherein said organism comprises a defect in an amino acid sequence which is associated with regulation of an atonal-associated nucleic acid sequence.

In another embodiment of the present invention there is a composition to treat an organism for cancer, wherein said organism comprises a defect in an atonal-associated nucleic acid sequence. In a specific embodiment the defect is a mutation or alteration of said atonal-associated nucleic acid sequence. In another specific embodiment the defect affects a regulatory sequence of said atonal-associated nucleic acid sequence. In an additional embodiment of the present invention there is a composition to treat an organism for cancer, wherein said organism comprises defect in a nucleic acid sequence which is associated with regulation of an atonal-associated nucleic acid sequence. In an additional embodiment of the present invention there is a composition to treat an organism for cancer, wherein said organism comprises a defect in an amino acid sequence which is associated with regulation of an atonal-associated nucleic acid sequence. In a specific embodiment said cancer is medulloblastoma.

Nucleic Acid-based Expression Systems

1. Vectors

One of skill in the art would be well equipped to construct a vector through standard recombinant techniques, which are described in Sambrook et al., 1989 and Ausubel et al., 1994, both incorporated herein by reference.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control, sequences that govern transcription and translation, vectors and expression vectors can contain nucleic acid sequences that serve other functions as well and are described infra.

a. Promoters and Enhancers

A "promoter" is a control sequence that is a region of a nucleic acid sequence at which initiation and rate of transcription are controlled. It can contain genetic elements at which regulatory proteins and molecules can bind such as RNA polymerase and other transcription factors. A promoter may or may not be used in conjunction with an "enhancer," which refers to a cis-acting regulatory sequence involved in the transcriptional activation of a nucleic acid sequence.

Naturally, it will be important to employ a promoter and/or enhancer that effectively directs the expression of the DNA segment in the cell type, organelle, and organism chosen for expression. Those of skill in the art of molecular biology generally know the use of promoters, enhancers, and cell type combinations for protein expression, for example, see Sambrook et al. (1989), incorporated herein by reference. The promoters employed can be constitutive, tissue-specific, inducible, and/or useful under the appropriate conditions to direct high level expression of the introduced DNA segment, such as is advantageous in the large-scale production of recombinant proteins and/or peptides. The promoter can be heterologous or endogenous.

The identity of tissue-specific promoters or elements, as well as assays to characterize their activity, is well known to those of skill in the art. Examples of such regions include the human LIMK2 gene (Nomoto et al. 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki, et al., 1998), D1A dopamine receptor gene (Lee, et al., 1997), insulin-like growth factor II (Wu et al., 1997), human platelet endothelial cell adhesion molecule-1 (Almendro et al., 1996).

b. Initiation Signals and Internal Ribosome Binding Sites

A specific initiation signal also can be required for efficient translation of coding sequences. These signals include the ATG initiation codon or adjacent sequences. Exogenous translational control signals, including the ATG initiation codon, can need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression can be enhanced by the inclusion of appropriate transcription enhancer elements.

In certain embodiments of the invention, the use of internal ribosome entry sites (IRES) elements are used to create multigene, or polycistronic, messages. IRES elements can be linked to heterologous open reading frames. Multiple open reading frames can be transcribed together, each separated by an IRES, creating polycistronic, messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

c. Multiple Cloning Sites

Vectors can include a multiple cloning site (MCS), which is a nucleic acid region that contains multiple restriction enzyme sites, any of which can be used in conjunction with standard recombinant technology to digest the vector. (See Carbonelli et al., 1999, Levenson et al., 1998, and Cocea, 1997, incorporated herein by reference.)

d. Splicing Sites

Most transcribed eukaryotic RNA molecules will undergo RNA splicing to remove introns from the primary transcripts. Vectors containing genomic eukaryotic sequences can require donor and/or acceptor splicing sites to ensure proper processing of the transcript for protein expression. (See Chandler et al., 1997, herein incorporated by reference.)

e. Polyadenylation Signals

In expression, one will typically include a polyadenylation signal to effect proper polyadenylation of the transcript. Specific embodiments include the SV40 polyadenylation signal and/or the bovine growth hormone polyadenylation signal, convenient and/or known to function well in various target cells.

f. Origins of Replication

In order to propagate a vector in a host cell, it can contain one or more origins of replication sites (often termed "ori"), which is a specific nucleic acid sequence at which replication is initiated.

g. Selectable and Screenable Markers

In certain embodiments of the invention, the cells contain nucleic acid construct of the present invention, a cell can be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP or enhanced GFP, whose basis is colorimetric analysis, are also contemplated. Alternatively, screenable enzymes such as herpes simplex virus thymidine kinase (tk) or chloramphenicol acetyltransferase (CAT) can be utilized. One of skill in the art would also know how to employ immunologic markers, possibly in conjunction with FACS analysis. Further examples of selectable and screenable markers are well known to one of skill in the art.

2. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®. Other examples of expression systems are well known in the art.

Nucleic Acid Detection

In addition to their use in directing the expression of atonal-associated proteins, polypeptides and/or peptides, the nucleic acid sequences disclosed herein have a variety of other uses. For example, they have utility as probes or primers or in any of the methods for embodiments involving nucleic acid hybridization, amplification of nucleic acid sequences, detection of nucleic acids, and other assays. A skilled artisan is aware of the following patents regarding details of these methods: U.S. Pat. Nos. 5,840,873; 5,843,640; 5,843,650; 5,843,651; 5,843,663; 5,846,708; 5,846,709; 5,846,717; 5,846,726; 5,846,729; 5,846,783; 5,849,481; 5,849,483; 5,849,486; 5,849,487; 5,849,497; 5,849,546; 5,849,547; 5,851,770; 5,851,772; 5,853,990; 5,853,993; 5,853,992; 5,856,092; 5,858,652; 5,861,244; 5,863,732; 5,863,753; 5,866,331; 5,866,336; 5,866,337; 5,900,481; 5,905,024; 5,910,407; 5,912,124; 5,912,145; 5,912,148; 5,916,776; 5,916,779; 5,919,626; 5,919,630; 5,922,574; 5,925,511; 5,925,525; 5,928,862; 5,928,869; 5,928,870; 5,928,905; 5,928,906; 5,929,227; 5,932,413; 5,932,451; 5,935,791; 5,935,825; 5,939,291; 5,942,391; European Application No. 320 308; European Application No. 329 822; GB Application No. 2 202 328; PCT Application No. PCT/US87/00880; PCT Application No. PCT/US89/01025; PCT Application WO 88/10315; PCT Application WO 89/06700; and PCT Application WO 90/07641.

Kits

All the essential materials and/or reagents required for detecting a sequence selected from SEQ ID NO:1 through SEQ ID NO:66 in a sample can be assembled together in a kit. This generally will comprise a probe or primers designed to hybridize specifically to individual nucleic acids of interest in the practice of the present invention, such as the nucleic acid sequences in SEQ ID NO:1 through SEQ ID NO:66. Also included can be enzymes suitable for amplifying nucleic acids, including various polymerases (reverse transcriptase, Taq, etc.), deoxynucleotides and buffers to provide the necessary reaction mixture for amplification. Such kits can also include enzymes and other reagents suitable for detection of specific nucleic acids or amplification products. Such kits generally will comprise, in suitable means, distinct containers for each individual reagent or enzyme as well as for each probe or primer pair.

Atonal-Associated Nucleic Acids

A. Nucleic Acids and Uses Thereof

A nucleic acid can be purified on polyacrylamide gels, cesium chloride centrifugation gradients, or by any other means known to one of ordinary skill in the art (see for example, Sambrook et al. 1989, incorporated herein by reference).

The term "nucleic acid" will generally refer to at least one molecule or strand of DNA, RNA or a derivative or mimic thereof, comprising at least one nucleobase, such as, for example, a naturally occurring purine or pyrimidine base found in DNA (e.g. adenine "A," guanine "G," thymine "T" and cytosine "C") or RNA:(e.g. A, G, uracil "U" and C). The term "nucleic acid" encompass the terms "oligonucleotide" and "polynucleotide." The term "oligonucleotide" refers to at least one molecule of between about 3 and about 100 nucleobases in length. The term "polynucleotide" refers to at least one molecule of greater than about 100 nucleobases in length. These definitions generally refer to at least one single-stranded molecule, but in specific embodiments will also encompass at least one additional strand that is partially, substantially or fully complementary to the at least one single-stranded molecule. Thus, a nucleic acid can encompass at least one double-stranded molecule or at least one triple-stranded molecule that comprises one or more complementary strand(s) or "complement(s)" of a particular sequence comprising a strand of the molecule. As used herein, a single stranded nucleic acid can be denoted by the prefix "ss", a double stranded nucleic acid by the prefix "ds", and a triple stranded nucleic acid by the prefix "ts."

Thus, the present invention also encompasses at least one nucleic acid that is complementary to a atonal-associated nucleic acid. In particular embodiments the invention encompasses at least one nucleic acid or nucleic acid segment complementary to the nucleic acid sequences set forth in SEQ ID NO:1 through SEQ ID NO:66, of those which are nucleic acid sequences. Nucleic acid(s) that are "complementary" or "complement(s)" are those that are capable of base-pairing according to the standard Watson-Crick, Hoogsteen or reverse Hoogsteen binding complementarity rules. As used herein, the term "complementary" or "complement(s)" also refers to nucleic acid(s) that are substantially complementary, as can be assessed by the same nucleotide comparison set forth above. The term "substantially complementary" refers to a nucleic acid comprising at least one sequence of consecutive nucleobases, or semiconsecutive nucleobases if one or more nucleobase moieties are not present in the molecule, are capable of hybridizing to at least one nucleic acid strand or duplex even if less than all nucleobases do not base pair with a counterpart nucleobase.

Herein certain embodiments, a "gene" refers to a nucleic acid that is transcribed. As used herein, a "gene segment" is a nucleic acid segment of a gene. In certain aspects, the gene includes regulatory sequences involved in transcription, or message production or composition. In particular embodiments, the gene comprises transcribed sequences that encode for a protein, polypeptide or peptide. In other particular aspects, the gene comprises an atonal-associated nucleic acid, and/or encodes an atonal-associated polypeptide or peptide coding sequences. In keeping with the terminology described herein, an "isolated gene" can comprise transcribed nucleic acid(s), regulatory sequences, coding sequences, or the like, isolated substantially away from other such sequences, such as other naturally occurring genes, regulatory sequences, polypeptide or peptide encoding sequences, etc. In this respect, the term "gene" is used for simplicity to refer to a nucleic acid comprising a nucleotide sequence that is transcribed, and the complement thereof In particular aspects, the transcribed nucleotide sequence comprises at least one functional protein, polypeptide and/or peptide encoding unit. As will be understood by those in the art, this function term "gene" includes both genomic sequences, RNA or cDNA sequences or smaller engineered nucleic acid segments, including nucleic acid segments of a non-transcribed part of a gene, including but not limited to the non-transcribed promoter or enhancer regions of a gene. Smaller engineered gene nucleic acid segments can express, or can be adapted to express using nucleic acid manipulation technology, proteins, polypeptides, domains, peptides, fusion proteins, mutants and/or such like.

In certain embodiments, the nucleic acid sequence is a nucleic acid or nucleic acid segment. As used herein, the term "nucleic acid segment", are smaller fragments of a nucleic acid, such as for non-limiting example, those that encode only part of the atonal-associated peptide or polypeptide sequence. Thus, a "nucleic acid segment" can comprise any part of the atonal-associated gene sequence(s), of from about 2 nucleotides to the full length of the atonal-associated peptide or polypeptide encoding region. In certain embodiments, the "nucleic acid segment" encompasses the full length atonal-associated gene(s) sequence. In particular embodiments, the nucleic acid comprises any part of the SEQ ID NO:1 through SEQ ID NO:66, of from about 2 nucleotides to the full length of the sequence disclosed in SEQ ID NO:1 through SEQ ID NO:66.

In certain embodiments, the nucleic acid segment can be a probe or primer. As used herein, a "probe" is a nucleic acid utilized for detection of another nucleic acid and is generally at least about 10 nucleotides in length. As used herein, a "primer" is a nucleic acid utilized for polymerization of another nucleic acid is generally at least about nucleotides in length. A non-limiting example of this would be the creation of nucleic acid segments of various lengths and sequence composition for probes and primers based on the sequences disclosed in SEQ ID NO:1 through SEQ ID NO:66, of those which are nucleic acid sequences.

The nucleic acid(s) of the present invention, regardless of the length of the sequence itself, can be combined with other nucleic acid sequences, including but not limited to, promoters, enhancers, polyadenylation signals, restriction enzyme sites, multiple cloning sites, coding segments, and the like, to create one or more nucleic acid construct(s). As used herein, a "nucleic acid construct" is a recombinant molecule comprising at least two segments of different nucleic acid sequence. The overall length can vary considerably between nucleic acid constructs. Thus, a nucleic acid segment of almost any length can be employed, with the total length preferably being limited by the ease of preparation or use in the intended recombinant nucleic acid protocol.

In certain embodiments, the nucleic acid construct is a recombinant vector. As used herein, a "recombinant vector" is a nucleic acid comprising multiple segments of nucleic acids utilized as a vehicle for a nucleic acid sequence of interest. In certain aspects, the recombinant vector is an expression cassette. As used herein, an expression cassette is a segment of nucleic acid which comprises a gene of interest which can be transfered between different recombinant vectors by means well known in the art.

In particular embodiments, the invention concerns one or more recombinant vector(s) comprising nucleic acid sequences that encode an atonal-associated protein, polypeptide or peptide that includes within its amino acid sequence a contiguous amino acid sequence in accordance with, or essentially as set forth in, SEQ ID NO:2 through SEQ ID NO:66, of which sequences are amino acid sequences, corresponding to *Homo sapiens* or *Mus musculus* atonal-associated sequence. In other embodiments, the invention concerns recombinant vector(s) comprising nucleic acid sequences from other species that encode an atonal-associated protein, polypeptide or peptide that includes within its amino acid sequence a contiguous amino acid sequence in accordance with, or essentially as set forth in SEQ ID NO:2 through SEQ ID NO:66, of which sequences are amino acid sequences. In particular aspects, the recombinant vectors are DNA vectors.

It will also be understood that amino acid sequences or nucleic acid sequences can include additional residues, such as additional N- or C-terminal amino acids or 5' or 3' sequences, or various combinations thereof, and yet still be essentially as set forth in one of the sequences disclosed herein, so long as the sequence meets the criteria set forth above, including the maintenance of biological protein, polypeptide or peptide activity where expression of a proteinaceous composition is concerned. The addition of terminal sequences particularly applies to nucleic acid sequences that can, for example, include various non-coding sequences flanking either of the 5' and/or 3' portions of the coding region or can include various internal sequences, i.e., introns, which are known to occur within genes.

It will also be understood that this invention is not limited to the particular nucleic acid or amino acid sequences of SEQ ID NO:2 through SEQ ID NO:66, of which sequences are amino acids. Recombinant vectors and isolated nucleic acid segments can therefore variously include these coding regions themselves, coding regions bearing selected alterations or modifications in the basic coding region, and they can encode larger polypeptides or peptides that nevertheless include such coding regions or can encode biologically functional equivalent proteins, polypeptide or peptides that have variant amino acids sequences.

The nucleic acids of the present invention encompass biologically functional equivalent atonal-associated proteins, polypeptides, or peptides or atonal-associated proteins, polypeptides or polypeptides. Such sequences can arise as a consequence of codon redundancy or functional equivalency that are known to occur naturally within nucleic acid sequences or the proteins, polypeptides or peptides thus encoded. Alternatively, functionally equivalent proteins, polypeptides or peptides can be created via the application of recombinant DNA technology, in which changes in the protein, polypeptide or peptide structure can be engineered, based on considerations of the properties of the amino acids being exchanged. Changes designed by man can be introduced, for example, through the application of site-directed mutagenesis techniques as discussed herein below, e.g., to introduce improvements or alterations to the antigenicity of the protein, polypeptide or peptide, or to test mutants in order to examine atonal-associated protein, polypeptide or peptide activity at the molecular level.

Fusion proteins, polypeptides or peptides can be prepared, e.g., where the atonal associated coding regions are aligned within the same expression unit with other proteins, polypeptides or peptides having desired functions. Non-limiting examples of such desired functions of expression sequences include purification or, immunodetection purposes for the added expression sequences, e.g., proteinaceous compositions that can be purified by affinity chromatography or the enzyme labeling of coding regions, respectively EP 266,032, or via deoxynucleoside H-phosphonate intermediates as described by Froehler et al., Nucl. Acids Res., 14:5399-5407, 1986, As used herein an "organism" can be a prokaryote, eukaryote, virus and the like. As used herein the term "sequence" encompasses both the terms "nucleic acid" and "proteanceocous" or "proteanaceous composition." As used herein, the term "proteinaceous composition" encompasses the terms "protein", "polypeptide" and. "peptide." As used herein "artificial sequence" refers to a sequence of a nucleic acid not derived from sequence naturally occurring at a genetic locus, as well as the sequence of any proteins, polypeptides or peptides encoded by such a nucleic acid. A "synthetic sequence", refers to a nucleic acid or proteinaceous composition produced by chemical synthesis in vitro, rather than enzymatic production in vitro (i.e. an "enzymatically produced" sequence) or biological production in vivo (i.e. a "biologically produced" sequence).

Cancer Therapies

Given the present invention is directed to methods and compositions for the treatment of abnormal cell proliferation, a discussion of therapies of cancer, which is the state of abnormal cell proliferation, is warranted.

A wide variety of cancer therapies, such as radiotherapy, surgery, chemotherapy and gene therapy, are known to one of skill in the art, can be used regarding the methods and compositions of the present invention.

Radiotherapeutic Agents

Radiotherapeutic agents and factors include radiation and waves that induce DNA damage for example, g-irradiation, X-rays, UV-irradiation, microwaves, electronic emissions, radioisotopes, and the like. Therapy can be achieved by irradiating the localized tumor site with the above described forms of radiations.

Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

Surgery

Surgical treatment for removal of the cancerous growth is generally a standard procedure for the treatment of tumors and cancers. This attempts to remove the entire cancerous growth. However, surgery is generally combined with chemotherapy and/or radiotherapy to ensure the destruction of any remaining neoplastic or malignant cells. Thus, surgery can be used in the context of the present invention.

Chemotherapeutic Agents

These can be, for example, agents that directly cross-link DNA, agents that intercalate into DNA, or agents that lead to chromosomal and mitotic aberrations by affecting nucleic acid synthesis.

Agents that directly cross-link nucleic acids, specifically DNA, are envisaged and are shown herein, to eventuate DNA damage leading to a synergistic antineoplastic combination. Agents such as cisplatin, and other DNA alkylating agents can be used.

Agents that damage DNA also include compounds that interfere with DNA replication, mitosis, and chromosomal segregation. Examples of these compounds include adriamycin (also known as doxorubicin), VP-16 (also known as etoposide), verapamil, podophyllotoxin, and the like. Widely used in clinical setting for the treatment of neoplasms these compounds, are administered through bolus injections intravenously at doses ranging from 25-75 mg/m2 at 21 day intervals for adriamycin, to 35-100 mg/m2 for etoposide intravenously or orally.

Cancer therapies also include a variety of combination therapies with both chemical and other types of treatments. Chemotherapeutics include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin and methotrexate, or any analog or derivative variant of the foregoing.

Genes

Gene Therapy Administration

For gene therapy, a skilled artisan would be cognizant that the vector to be. utilized must contain the gene of interest operatively linked to a promoter. For antisense gene therapy, the antisense sequence of the gene of interest would be operatively linked to a promoter. One skilled in the art recognizes that in certain instances other sequences such as a 3' UTR regulatory sequences are useful in expressing the gene of interest. Where appropriate, the gene therapy vectors can be formulated into preparations in solid, semisolid, liquid or gaseous forms in the ways known in the art for their respective route of administration. Means known in the art can be utilized to prevent release and absorption of the composition until it reaches the target organ or to ensure timed-release of the composition. A pharmaceutically acceptable form should be employed which does not ineffectuate the compositions of the present invention. In pharmaceutical dosage forms, the compositions can be used alone or in appropriate association, as well as in combination, with other pharmaceutically active compounds. A sufficient amount of vector containing the therapeutic nucleic acid sequence must be administered to provide a pharmacologically effective dose of the gene product.

One skilled in the art recognizes that different methods of delivery can be utilized to administer a vector into a cell. Examples include: (1) methods utilizing physical means, such as electroporation (electricity), a gene gun (physical force) or applying large volumes of a liquid (pressure); and (2) methods wherein said vector is complexed to another entity, such as a liposome, viral vector or transporter molecule.

Accordingly, the present invention provides a method of transferring a therapeutic gene to a host, which comprises administering the vector of the present invention, preferably as part of a composition, using any of the aforementioned routes of administration or alternative routes known to those skilled in the art and appropriate for a particular application. Effective gene transfer of a vector to a host cell in accordance with the present invention to a host cell can be monitored in terms of a therapeutic effect (e.g. alleviation of some symptom associated with the particular disease being treated) or, further, by evidence of the transferred gene or expression of the gene within the host (e.g., using the polymerase chain reaction in conjunction with sequencing, Northern or Southern hybridizations, or transcription assays to detect the nucleic acid in host cells, or using immunoblot analysis, antibody-mediated detection, mRNA or protein half-life studies, or particularized assays to detect protein or polypeptide encoded by the transferred nucleic acid, or impacted in level or function due to such transfer).

These methods described herein are by no means all-inclusive, and further methods to suit the specific application will be apparent to the ordinary skilled artisan. Moreover, the effective amount of the compositions can be further approximated through analogy to compounds known to exert the desired effect.

Furthermore, the actual dose and schedule can vary depending on whether the compositions are administered in combination with other pharmaceutical compositions, or depending on interindividual differences in pharmacokinetics, drug disposition, and metabolism. Similarly, amounts can vary in in vitro applications depending on the particular cell line utilized (e.g., based on the number of vector receptors present on the cell surface, or the ability of the particular vector employed for gene transfer to replicate in that cell line). Furthermore, the amount of vector to be added per cell will likely vary with the length and stability of the therapeutic gene inserted in the vector, as well as also the nature of the sequence, and is particularly a parameter which needs to be determined empirically, and can be altered due to factors not inherent to the methods of the present invention (for instance, the cost associated with synthesis). One skilled in the art can easily make any necessary adjustments in accordance with the exigencies of the particular situation.

It is possible that cells containing the therapeutic gene can also contain a suicide gene (i.e., a gene which encodes a product that can be used to destroy the cell, such as herpes simplex virus thymidine kinase). In many gene therapy situations, it is desirable to be able to express a gene for therapeutic purposes in a host cell but also to have the capacity to destroy the host cell once the therapy is completed, becomes uncontrollable, or does not lead to a predictable or desirable result. Thus, expression of the therapeutic gene in a host cell can be driven by a promoter although the product of said suicide gene remains harmless in the absence of a prodrug. Once the therapy is complete or no longer desired or needed, administration of a prodrug causes the suicide gene product to become lethal to the cell. Examples of suicide gene/prodrug combinations which can be used are Herpes Simplex Virus-thymidine kinase (HSV-tk) and ganciclovir, acyclovir or FIAU; oxidoreductase and cycloheximide; cytosine deaminase and 5-fluorocytosine; thymidine kinase thymidilate kinase (Tdk::Tmk) and AZT; and deoxycytidine kinase and cytosine arabinoside.

The method of cell therapy can be employed by methods known in the art wherein a cultured cell containing a copy of a nucleic acid sequence or amino acid sequence of Math1 is introduced.

In yet another embodiment, the secondary treatment is a secondary gene therapy in which a second therapeutic polynucleotide is administered before, after, or at the same time a first therapeutic polynucleotide encoding all of part of an atonal-associated polypeptide. Delivery of a vector encoding either a full length or partial atonal-associated polypeptide in conjuction with a second vector encoding another gene product will have a combined anti-hyperproliferative effect on target tissues. Alternatively, a single vector encoding both genes can be used.

Immunotherapy

Immunotherapeutics, generally, rely on the use of immune effector cells and molecules to target and destroy cancer cells. The immune effector can be, for example, an antibody specific for some marker on the surface of a tumor cell. The antibody alone can serve as an effector of therapy or it can recruit other cells to actually effect cell killing. The antibody also can be conjugated to a drug or toxin (chemotherapeutic, radionuclide, ricin A chain, cholera toxin, pertussis toxin, etc.) and serve merely as a targeting agent. Alternatively, the effector can be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with Ad-mda7 gene therapy. The general approach for combined therapy is discussed below. Generally, the tumor cell must bear some marker that is amenable to targeting, i.e., is not present on the majority of other cells. Many tumor markers exist and any of these can be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA; MucB, PLAP, estrogen receptor, laminin receptor, erb B and p155.

Combination Treatments

It can be desirable in utilizing the present invention to combine the compositions with other agents effective in the treatment of hyperproliferative disease, such as anti-cancer agents. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell. This process can involve contacting the cells with the expression construct and the agent(s) or multiple factor(s) at the same time. This can be achieved by contacting the cell with a single composition or pharmacological formulation that includes both agents, or by contacting the cell with two distinct compositions or formulations, at the same time, wherein one composition includes the expression construct and the other includes the second agent(s).

Tumor cell resistance to chemotherapy and radiotherapy agents represents a major problem in clinical oncology. One goal of current cancer research is to find ways to improve the efficacy of chemo- and radiotherapy by combining it with gene therapy. For example, the herpes simplex-thymidine kinase (HS-tK) gene, when delivered to brain tumors by a retroviral vector system, successfully induced susceptibility to the antiviral agent ganciclovir (Culver, et al., 1992). In the context of the present invention, it is contemplated that mda-7 gene therapy could be used similarly in conjunction with chemotherapeutic, radiotherapeutic, or immunotherapeutic intervention, in addition to other pro-apoptotic or cell cycle regulating agents.

Alternatively, the gene therapy can precede or follow the other agent treatment by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one can contact the cell with both modalities within about 12-24 h of each other and, more preferably, within about 6-12 h of each other. In some situations, it can be desirable to extend the time period for treatment significantly, however, where several d (2, 3, 4, 5, 6 or 7) to several wk (1, 2, 3, 4, 5, 6, 7 or 8) lapse between the respective administrations.

Various combinations can be employed, gene therapy is "A" and the secondary agent, such as radio- or chemotherapy, is "B":

be a member of a family of related proteins, which can be categorized as death agonists or death antagonists. Different family members have been shown to either possess similar functions to Bcl-2 (e.g., BclXL, BclW, BclS, Mcl-1, A1, Bfl-1) or counteract Bcl-2 function and promote cell death (e.g., Bax, Bak, Bik, Bim, Bid, Bad, Harakiri).

Other agents

It is contemplated that other agents can be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adehesion, or agents that increase the sensitivity of the hyperproliferative cells to apoptotic inducers.

Dosage and Formulation

The amino acid sequences and nucleic acid sequences (active ingredients) of this invention can be formulated and administered to treat a variety of disease states by any means that produces contact of the active ingredient with the agent's site of action in the body of an animal. They can be administered by any conventional means available for use in conjunc-

```
A/B/A   B/A/B   B/B/A   A/A/B   A/B/B   B/A/A   A/B/B/B   B/A/B/B

B/B/B/A   B/B/A/B   A/A/B/B   A/B/A/B   A/B/B/A   B/B/A/A

B/A/B/A   B/A/A/B   A/A/A/B   B/A/A/A   A/B/A/A   A/A/B/A
```

Administration of the therapeutic expression constructs of the present invention to a patient will follow general protocols for the administration of chemotherapeutics, taking into account the toxicity, if any, of the vector. It is expected that the treatment cycles would be repeated as necessary. It also is contemplated that various standard therapies, as well as surgical intervention, can be applied in combination with the described hyperproliferative cell therapy.

Inhibitors of Cellular Proliferation

The tumor suppressor oncogenes function to inhibit excessive cellular proliferation. The inactivation of these genes destroys their inhibitory activity, resulting in unregulated proliferation. The tumor suppressors p53, p16 and C-CAM are specific embodiments utilized in the present invention. Other genes that can be employed according to the present invention include Rb, APC, DCC, NF-1, NF-2, WT-1, MEN-I, MEN-II, zac1, p73, VHL, MMAC1/PTEN, DBCCR-1, FCC, rsk-3, p27, p27/p16 fusions, p21/p27 fusions, anti-thrombotic genes (e.g., COX-1, TFPI), PGS, Dp, E2F, ras, myc, neu, raf, erb, fms, trk, ret, gsp, hst, abl, E1A, p300, genes involved in angiogenesis (e.g., VEGF, FGF, thrombospondin, BAI-1, GDAIF, or their receptors) and MCC.

Regulators of Programmed Cell Death

Apoptosis, or programmed cell death, is an essential process for normal embryonic development, maintaining homeostasis in adult tissues, and suppressing carcinogenesis (Kerr et al., 1972). The Bcl-2 family of proteins and ICE-like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli (Bakhshi et al., 1985; Cleary and Sklar, 1985; Cleary et al., 1986; Tsujimoto et al., 1985; Tsujimoto and Croce, 1986). The evolutionarily conserved Bcl-2 protein now is recognized to tion with pharmaceuticals, either as individual therapeutic active ingredients or in a combination of therapeutic active ingredients. They can be administered alone, or with a pharmaceutically acceptable carrier selected on the basis of the chosen route of administration and standard pharmaceutical practice.

The dosage administered will be a therapeutically effective amount of active ingredient and will, of course, vary depending upon known factors such as the pharmacodynamic characteristics of the particular active ingredient and its mode and route of administration; age, sex, health and weight of the recipient; nature and extent of symptoms; kind of concurrent treatment, frequency of treatment and the effect desired.

The active ingredient can be administered orally in solid dosage forms such as capsules, tablets and powders, or in liquid dosage forms such as elixirs, syrups, emulsions and suspensions. The active ingredient can also be formulated for administration parenterally by injection, rapid infusion, nasopharyngeal absorption or dermoabsorption. The agent can be administered intramuscularly, intravenously, or as a suppository. In addition, parenteral solutions can contain preservatives such as benzalkonium chloride, methyl- or propylparaben and chlorobutanol. Suitable pharmaceutical carriers are described in *Remington's Pharmaceutical Sciences*, a standard reference text in this field.

Additionally, standard pharmaceutical methods can be employed to control the duration of action. These are well known in the art and include control release preparations and can include appropriate macromolecules, for example polymers, polyesters, polyamino acids, polyvinyl, pyrolidone, ethylenevinylacetate, methyl cellulose, carboxymethyl cellulose or protamine sulfate. The concentration of macromolecules as well as the methods of incorporation can be adjusted in order to control release. Additionally, the agent can be incorporated into particles of polymeric materials such as polyesters, polyamino acids, hydrogels, poly (lactic acid) or ethylenevinylacetate copolymers. In addition to being incorporated, these agents can also be used to trap the compound in microcapsules.

Useful pharmaceutical dosage forms for administration of the compounds of this invention can be illustrated as follows:

Capsules: Capsules are prepared by filling standard two-piece hard gelatin capsulates each with a therapeutically effective amount of powdered active ingredient, 175 milligrams of lactose, 24 milligrams of talc and 6 milligrams magnesium stearate.

Soft Gelatin Capsules: A mixture of active ingredient in soybean oil is prepared and injected by means of a positive displacement pump into gelatin to form soft gelatin capsules containing a therapeutically effective amount of the active ingredient. The capsules are then washed and dried.

Tablets: Tablets are prepared by conventional procedures so that the dosage unit is a therapeutically effective amount of active ingredient. 0.2 milligrams of colloidal silicon dioxide, 5 milligrams of magnesium stearate, 275 milligrams of microcrystalline cellulose, 11 milligrams of cornstarch and 98.8 milligrams of lactose. Appropriate coatings can be applied to increase palatability or to delay absorption.

Injectable: A parenteral composition suitable for administration by injection is prepared by stirring 1.5% by weight of active ingredients in 10% by volume propylene glycol and water. The solution is made isotonic with sodium chloride and sterilized.

Suspension: An aqueous suspension is prepared for oral administration so that each 5 millimeters contain a therapeutically effective amount of finely divided active ingredient, 200 milligrams of sodium carboxymethyl cellulose, 5 milligrams of sodium benzoate, 1.0 grams of sorbitol solution U.S.P. and 0.025 millimeters of vanillin.

Accordingly, the pharmaceutical composition of the present invention can be delivered via various routes and to various sites in an animal body to achieve a particular effect (see, e.g., Rosenfeld et al. (1991), supra; Rosenfeld et al., Clin. Res., 39(2), 311A (1991a); Jaffe et al., supra; Berkner, supra). One skilled in the art will recognize that although more than one route can be used for administration, a particular route can provide a more immediate and more effective reaction than another route. Local or systemic delivery can be accomplished by administration comprising application or instillation of the formulation into body cavities, inhalation or insufflation of an aerosol, or by parenteral introduction, comprising intramuscular, intravenous, peritoneal, subcutaneous, intradermal, as well as topical administration.

The composition of the present invention can be provided in unit dosage form wherein each dosage unit, e.g., a teaspoonful, tablet, solution, or suppository, contains a predetermined amount of the composition, alone or in appropriate combination with other active agents. The term "unit dosage form" as used herein refers to physically discrete units suitable as unitary dosages for human and animal subjects, each unit containing a predetermined quantity of the compositions of the present invention, alone or in combination with other active agents, calculated in an amount sufficient to produce the desired effect, in association with a pharmaceutically acceptable diluent, carrier, or vehicle, where appropriate. The specifications for the unit dosage forms of the present invention depend on the particular effect to be achieved and the particular pharmacodynamics associated with the pharmaceutical composition in the particular host.

These methods described herein are by no means all-inclusive, and further methods to suit the specific application will be apparent to the ordinary skilled artisan. Moreover, the effective amount of the compositions can be further approximated through analogy to compounds known to exert the desired effect.

The following examples are offered by way of example, and are not intended to limit the scope of the invention in any manner.

EXAMPLE 1

Mouse Atonal Homolog 1 (Math1)

It has been found that the present methods for the treatment of the hearing impaired have failed to address the problem directly, that is, the regeneration of auditory hair cell populations. The present invention in a preferred embodiment is directed to a member of the bHLH family, the Math1 gene or an another atonal-associated nucleic acid sequence, and its requirement for generation of cerebellar granule neurons and inner ear hair cells. This discovery has wide ramifications not only for understanding neurodevelopment but also for therapies for a variety of prevalent disorders, as described below.

The mouse atonal homolog 1 (Math1) is expressed in the precursors of the cerebellar granule neurons; a few cells in the dorsal portion of the developing spinal cord; the inner ear; Merkel cells (touch receptors on the skins); and joints. Overexpressing Math1 in an otherwise differentiated cell can induce the formation or differentiation into a progenitor or mature inner ear hair cell-like cell.

Math1 expression in the precursors of the cerebellar granule neurons suggests it is required for function in the cerebellum and brain. The cerebellum is essential for fine motor coordination and posture, and its dysfunction disrupts balance, speech and limb movements. Cerebellar development typically begins at about embryonic day 9.5 (E9.5) when a small group of cells in the hindbrain proliferates and migrates rostrally to form the external granule layer, brain stem, and pontine neurons. This population of neuronal progenitors, which continues to express Math1, further proliferates and migrates internally to form the cerebellar granule neurons that are the predominant neuronal population in the cerebellum and brain. Mice that do not express Math1 completely lack cerebellar granule neurons and their precursors. Math1 is thus essential for the generation of these neurons and endows the very sparse population of neurons at E9.5 with the ability to proliferate into billions and then differentiate (Ben-Arie et al., 1997). Both these functions are of great medical significance. To understand normal proliferation provides necessary insight into abnormal proliferation, as observed in cancer. Cerebellar tumors of the primitive neuroectodermal type (e.g., medulloblastoma) are the most common solid malignancy in children. Math1 expressing cells contribute significantly to these tumors.

Math1 is expressed in the non-ossified joint cartilage (see FIG. 6) that typically degenerates in osteoarthritis. This is the most prevalent form of arthritis, with 90% of people over 40 showing some degree of osteoarthritis in one or more joints. Given the properties of Math1 in cellular generation and proliferation, its artificial expression in affected joints can allow regeneration of the cells that constitute non-ossified cartilage.

Disclosed herein are compositions and methods for the use of the Math1 gene, its human homolog (Hath1) or any of its homologs, orthologs, chimeric fusion proteins or derivatives of any suitable atonal-associated nucleic acid sequence or any another atonal-associated nucleic acid sequence. To learn about the functions of Math1 in mammals, the Math1 gene was deleted from a mouse using a strategy that permitted detection of cells that express Math1. Disclosed are the creation and characterization of mice that can be used to screen for compounds which could be utilized to decrease or augment Math1 expression in inner ear hair cells and other cells in which Math1 expression is associated.

Methods are also disclosed for the study, characterization and treatment of neoplastic proliferation of neuroectodermal origin since Math1 expression is essential for the generation and proliferation of cerebellar granule neurons. Also, it has been discovered that Math1 plays a role in the development of cells that produce non-ossified joint cartilage, which are associated with the development of osteoarthitis. These discoveries have led to a method of screening for compounds that can be helpful for the treatment of inner ear hair cell loss and other diseases that occur due to the functional loss of Math1, such as osteoarthritis.

More particularly, the present invention also provides an animal heterozygous for Math1 gene inactivation or an another atonal-associated nucleic acid sequence, wherein at least one Math1 allele or another atonal-associated nucleic acid sequence has been replaced by insertion of a heterologous nucleic acid sequence, wherein the inactivation of the Math1 or atonal-associated sequence prevents expression of the Math1 or atonal-associated allele. The mouse can be further used to generate mice homozygous for Math1 or another atonal-associated sequence gene inactivation and can further include a second heterologous nucleic acid sequence, wherein at least one of the heterologous genes is used to detect expression driven by the Math1 or atonal-associated sequence regulatory elements. The complete or partial inactivation of the functional Math1 or atonal-associated sequence can be detected in, e.g., proprioreceptory cells, granule neurons and their progenitor cells, or non-ossified cartilage cells.

Examples of heterologous nucleic acid sequences are reporter sequences such as b-galactosidase, green fluorescent protein (GFP), blue fluorescent protein (BFP), neomycin, kanamycin, luciferase, b-glucuronidase and chloramphenicol transferase (CAT). The Math1 or atonal-associated sequence can also be replaced under the control of regulatable promoter sequences or can be a tissue-specific promoter sequences. Said promoter sequences can be partial or can contain the entire promoter.

The present invention can also be used as, or as part of, a method for screening for a compound, wherein the administration of the compound affects a developmental and/or pathological condition wherein said condition is a result of reduction in expression of the Math1 or atonal-associated sequence, the method including, administering the compound to a transgenic mouse that is homozygous for Math1 or atonal-associated sequence inactivation, wherein at least one Math1 or atonal-associated allele is inactivated by insertion of a heterologous nucleic acid sequence, wherein the inactivation of the Math1 or atonal-associated sequence prevents expression of the Math1 or atonal-associated gene, and monitoring the mouse for a change in the developmental and/or pathological condition. The types of pathological conditions that can be examined include, but are not limited to loss of hair cells, loss of cerebellar granule neurons or their precursors, lack of granule cell proliferation or migration, lack of cerebellar external granule layer cells, hearing impairment, an imbalance disorder, joint disease, osteoarthritis, abnormal proliferation of neoplastic neuroectodermal cells and formation of medulloblastoma. As used herein, the screen provides for a compound that by upregulating expression of a heterologous nucleic acid sequence is a positive effector and for a compound that by downregulating expression of a heterologous nucleic acid sequence is a negative effector.

Yet another embodiment of the present invention is a method of promoting mechanoreceptive cell growth, that includes contacting a cell with a Math1 or atonal-associated protein or gene in an amount effective to cause said cell to express an inner ear hair cell marker. An example of a hair cell marker for use with the method is calretinin. The cell can be contacted with a vector that expresses a Math1 or atonal-associated nucleic acid sequence or amino acid sequence. Math1 or atonal-associated nucleic acid sequence-expressing recombinant vectors can include an adenoviral vector, a retroviral vector, an adeno-associated vector, a plasmid, a liposome, a protein, a lipid, a carbohydrate and a combination thereof of said vectors. Math1 or atonal-associated sequence can be under the control of, e.g., a cytomegalovirus IE promoter sequence or the cytomegalovirus IE promoter sequence and a SV40 early polyadenylation signal sequence, or any other combination of appropriate promoter sequences, enhancer sequence, and polyadenylation.

Furthermore, a method is disclosed for treating hearing impairment or an imbalance disorder that includes administering to an animal, including a human, with hearing loss or an imbalance disorder a therapeutically effective amount of a Math1 or atonal-associated amino acid sequence or nucleic acid sequence. The hearing or balance impairment can be complete or partial and can affect either one ear or both ears. In a preferred embodiment, there is a substantial impairment of hearing. Hearing and an imbalance disorder can be affected separately or concomitantly in an animal to be treated, and said hearing and/or an imbalance disorder could be as a result of trauma, disease, age-related condition, or could be due to loss of hair cells for any reason.

The present invention is also directed to a composition that includes a Math1 or atonal-associated protein or gene in combination with a delivery vehicle, wherein the delivery vehicle causes a therapeutically effective amount of Math1 or atonal-associated sequence to be delivered into a cell. The delivery vehicle can be further defined as a vector that comprises a Math1 or atonal-associated amino acid sequence or nucleic acid sequence in an animal cell. The vector can be a retroviral or an adenoviral vector or any other nucleic acid based vector which can even be dispersed in a pharmacologically acceptable formulation, and used for intralesional administration. The composition can even be a partially or fully purified protein that is delivered using a liposome, a protein, a lipid or a carbohydrate that promotes the entry of a Math1 or atonal-associated protein into a cell. Examples of proteins that can be used as delivery vehicles include the receptor-binding domains (the non-catalytic regions) of bacterial toxins, such as, e.g., Exotoxin A, cholera toxin and Ricin toxin or protein transduction domains, such as from the HIV TAT protein (Schwarze et al., 1999) (see Example 22). The composition for delivering Math1 can be a fusion protein.

A skilled artisan is aware that methods to treat animals as disclosed in the invention can be either in utero or after birth. Treatment can be given to an embryo and can occur either ex vivo or in vivo.

EXAMPLE 2

Animal Model for Organogenesis

An effective animal model for deficiency in a gene that controls or ganogenesis will most often have both alleles stably inactivated so that, throughout embryogenesis, one or more tissues cannot revert to a functional wild-type allele.

One method of generating animals with an altered genotype is gene targeting (Mansour et al., 1993), in which homologous recombination of newly introduced DNA sequence (i.e., the targeting sequence or construct) and a specific targeted DNA sequence residing in the chromosome results in the insertion of a portion of the newly introduced DNA sequence into the targeted chromosomal DNA sequence. This method is capable of generating animals of any desired genotype, and is especially useful for gene disruption (i.e., to "knock out") at a specific chromosomal gene sequence by inserting a selectable marker into the gene or completely replacing the gene with another nucleotide sequence.

To knock out a genomic sequence, a cloned fragment must be available and intron-exon boundaries within the fragment defined (Mansour et al., 1993). Typically, the targeting construct contains a selectable marker such as Neo (neomycin resistance, see Mansour et al., 1993) flanked by sequences homologous to the chromosomal target DNA, and beyond one of these flanking sequences the herpes simplex virus thymidine kinase gene (HSV-TK, see generally, McKnight et al., 1980). The targeting construct is introduced, e.g., by electroporation, into embryo-derived stem (ES) cells where homologous recombination results in an insertion of the Neomycin resistance marker (Neo), but not the HSV-TK gene, into the targeted chromosomal DNA sequence. The altered ES cells are neomycin resistant and HSV-TK and so are able to grow in the presence of both G418 and gancyclovir antibiotics. Random insertions contain the HSV-TK gene and are thus sensitive to gancyclovir (Mansour, et al.). Positive ES clones are then microinjected into blastocysts to generate germ-line chimeric mice, which are then bred to obtain progeny that are homozygous for the knock out gene. Such general methods of generating knock out animals have been demonstrated using mice. Genes in other animals such as rats, guinea pigs, gerbils, hamsters, and rabbits, can also be used as long as sufficient DNA sequence data are available to make an appropriate targeting construct to knock out the gene of interest.

Although ato and Math1 share a high degree of sequence conservation, there was an apparent discrepancy between their expression patterns and the consequences of their loss of function. Whereas ato is expressed primarily in the PNS of the fly and its absence causes loss of almost all CHOs (Jarman et al., 1993), Math1 is expressed in the CNS and its loss leads to absence of cerebellar granule neurons, the largest neuronal population in the CNS (Ben-Arie et al., 1997). To better understand the functional relations between ato and Math1, the present invention describes generation of a second Math1 null allele in mice (Math1$^{b\text{-}gal/b\text{-}gal}$) by replacement of the Math1 coding region with a b-galactosidase gene (lacZ) and performing a subsequent search for CNS expression of ato in the fruit fly. The Examples describe a functional link between ato and Math1: ato is expressed in the fly brain, and lacZ expression under the control of Math1 regulatory elements (Math1/lacZ) not only replicated the known expression pattern in the CNS (i.e., the neural tube, spinal cord and cerebellum), but appeared in many other cells of the murine PNS. Overexpression of Math1 in Drosophila caused ectopic CHO formation, providing further evidence that ato and Math1 are functionally conserved.

The connections and consistency of the relationship between atonal in Drosophila and Math1 in the mouse suggests that their use as model systems in the art is justified. A family of homologues have been cloned and analyzed in the mouse including. MATH1,2,3,4A, 4B, 4C and 5 (Azakawa et al., 1995; Bartholoma and Nave, 1994; Ben-Arie et al., 1997; Ben-Arie et al., 1996, Fode et al., 1998; Ma et al., 1998; McCormick et al., 1996; Shimizu et al., 1995; Takebayashi et al., 1997). It has been suggested that Math1 and Math5 are the only true ato homologues given their amino acid sequence criteria, sharing 67% and 71% identity with the bHLH domain of ATO, respectively (Ben-Arie et al., 2000). A Xenopus atonal homolog, Xath1 has been ectopically expressed in Drosophila and shown to behave similarly to ato (Kim et al., 1997). Furthermore, the ability of Math1 to induce ectopic CHO formation and to restore CHOs to ato mutant embryos (see Example 13) is strong evidence that Math1, and particularly its basic domain, encodes lineage identity information not unlike that encoded by ato and that mammalian cells expressing Math1 are functionally similar and perhaps evolutionarily related to Drosophila cells that require ato. Thus, the similarities between atonal in Drosophila, Xath1 in Xenopus and Math1 in the mouse indicate that these animals are comparable animal model systems. Furthermore, the widespread use of mice in particular as a model system for humans also suggests that it similarly would allow utilization of the invention in humans.

With advances in molecular genetics now standard in the art, sequences from humans and other species can be used interchangeably in a variety of organisms. For example, the rat inducible hsp70 gene was used to produce transgenic mice that overexpressed inducible hsp70, allowing organs from transgenic mice to be protected from ischemic injury (Marber et al. J. clin. Invest. 95:1446-1456 (1995)) due to the increase in rat hsp70. Sequences in other animals have been interchanged including between humans and rodents to develop rodent models to study human disease, i.e. neurodegenerative diseases. One such example is the expression of the human SCA1 gene, which encodes ataxin-1, in mice (Burright, E. N. et al. Cell 82:937-948 (1995)). Transgenic mice were generated expressing the human SCA1 gene with either a normal or an expanded CAG tract. The data illustrated that the expanded CAG repeats were expressed in sufficient amounts in the Purkinje cells to produce degeneration and ataxia. This example illustrates that a mouse model can be established to study spinocerebellar ataxia type 1, which is an autosomal dominant inherited neurologic disorder. In addition to developing mouse models, Drosophila is a hallmark model system in the field. Warrick et al. (1999) produced transgenic flies which co-expressed human hsp70 and a human mutant polyglutamine (MJDtr-Q78). Expression of the human mutant polyglutamine MJDtr-Q78 alone in the flies resulted in the formation of large aggregates in neurons. However, co-expression with human hsp 70 resulted in suppressed aggregation. These examples illustrate that interchangeability of genes is routine in the field of molecular genetics and model systems provide powerful tools to characterize gene function.

EXAMPLE 3

Generation of Transgenic Math1 Mice

To detect subtle Math1 expression patterns not identified by RNA in situ hybridization, and thus further illuminate this gene's role during embryonic development, Math1 null alleles (Math1$^{\beta\text{-}Gal/\beta\text{-}Gal}$) were generated by replacing the Math1 coding region with β-galactosidase (β-Gal).

The targeting construct, containing a lacZ cassette and a PGK-neo cassette (FIG. 7A), was used to replace the Math1 coding region. To delete the entire coding region of Math1, a targeting construct was generated that contained the 5' and 3' genomic flanking fragments as described previously (Ben-Arie et al., 1997) flanking a pSAbgal/PGK-neo cassette (Friedrich and Soriano, 1991). The construct is designed so that lacZ expression is driven by endogenous Math1 control elements, while an independent PGK promoter drives the expression of the selectable marker neo.

Figure 7:
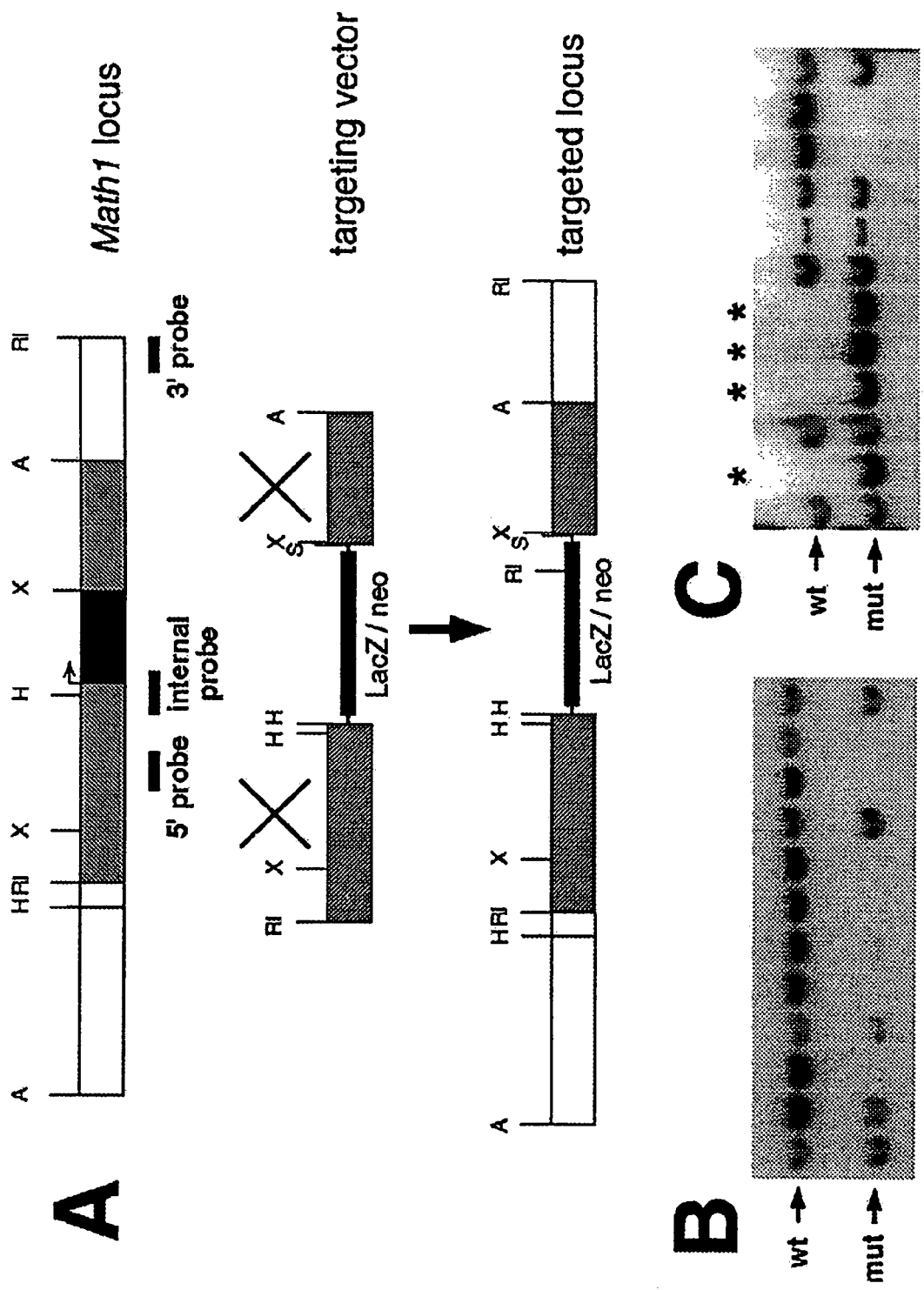
FIG. 7A through 7C show replacement of Math1 coding region by lacZ gene.

The construct was electroporated into ES cells and selection for neo was achieved with G418. Fourteen out of 76 (18%) clones underwent homologous recombination. Genotyping of ES cells, yolk sac and tail DNA was performed using Southern analysis of EcoR I digested DNA and probes previously described (Ben-Arie et al., 1997). The targeting construct was electroporated into embryonic stem (ES) cells; 14/76 (18%) clones exhibited correct homologous recombination at the Math1 locus (FIG. 7B).

Three ES cell lines carrying the Math1$^{+/b\text{-}gal}$ allele were injected into host blastocysts to generate chimeric mice. Math1$^{+/b\text{-}gal}$ mice were identified and intercrossed to generate homozygotes (FIG. 7C). The Math1 deletion was confirmed by Southern analysis using both flanking and internal probes (FIG. 7A).

Math1$^{\beta\text{-}Gal/\beta\text{-}Gal}$ mice show all the phenotypic features reported in the Math1$^{-/-}$ mice (Ben-Arie et al., 1997; 2000).

EXAMPLE 4

X-Gal Staining, Histological and Immunohistochemical Analyses

Embryos were staged by vaginal plug, with the morning of the plug designated E0.5. Embryos were dissected out of the uterus, separated from extraembryonic membranes, and placed in cold phosphate buffered saline (PBS). The embryos were then fixed in 4% paraformaldehyde (PFA) in PBS for 30 minutes, and washed in cold PBS. Yolk sacs or tails were collected before fixation for DNA extraction and genotyping. Equilibration to improve the penetrability of the staining reagents was performed in 0.02% NP40, 0.01% sodium deoxycholate in PBS for 10 minutes at room temperature. Whole mount staining with X-gal (Bonnerot and Nicolas, 1993) was performed for 16-24 hours at 30° C. while shaking in the same equilibration buffer, which also contained 5 mM potassium ferricyanide, 5 mM potassium ferrocyanide, and 40 mg/ml X-gal (dissolved in DMSO). When the desired intensity of staining was achieved, usually within 18 hours, embryos were washed in PBS, postfixed for 30 minutes in buffered formalin, serially dehydrated in 25, 50, and 70% ethanol, and stored at 4° C.

For histological analysis embryos were further dehydrated in 80, 90, and 100% ethanol, treated in Histoclear (National Diagnostics), and embedded in Paraplast (Oxford Labware). Seven to 20 μm sections were cut using in a microtome (Microme). Counterstaining was performed using nuclear fast red (Vector Laboratories). Immunohistochemistry was performed as detailed previously (Ben-Arie et al., 1997). Antibodies: Anti-cytokeratin 18 (DAKO) 1:20; Anti-human Chromogranin A (DAKO) 1:100; Anti-MATH1 (see below) 1:200.

EXAMPLE 5

Expression Patterns in Transgenic Math1 Mice

As expected, β-Gal expression in the cerebellum and dorsal spinal cord is identical to that of Math1, and interestingly, β-Gal is also expressed throughout the otic vesicle epithelia at E12.5 and in the sensory epithelia of the utricle, saccule, semicircular canals, and cochlea at E14.5 and E15.5 (FIGS. 1A and 1B). Utricles were obtained from C57BL/129SVEV mice.

Gross morphological analysis of the inner ear of Math1$^{\beta\text{-}Gal/\beta\text{-}Gal}$ mice at E18.5, one day before full gestation, revealed no obvious defects in overall structure and size compared with wild type (wt) littermates. The branches of the VIII$^{th}$ cranial nerve were present and reached the epithelia, but degenerated due to absence of the hair cells.

The sensory epithelia were examined in detail. The utricles and cochleas of wild-type, Math1$^{+/\beta\text{-}Gal}$, and Math1$^{\beta\text{-}Gal/\beta\text{-}Gal}$ mice were excised to allow viewing of the sensory epithelia with Nomarski optics. Hair bundles were present in both organs of wild-type and heterozygotes, but were completely absent in Math1 null litter-mates. Scanning electron microscopy (SEM) of the cochlea and vestibular organs confirmed the absence of hair bundles in null mice (FIGS. 2A through 2F). To determine whether lack of hair bundles reflects the absence of hair cells, cross-sections of the sensory epithelia of all inner ear organs using both light and transmission electron microscopy (LM and TEM, respectively) were examined (FIGS. 3A through 3F). LM and TEM were carried out as described previously (Lysakowski and Goldberg, 1997). Tissue preparation for SEM consisted of osmication (1% OsO$_4$ in cacodylate buffer), dehydration, critical-point drying, sputter-coating with gold, and examination in a JEOL 35S electron microscope.

Figure 4:
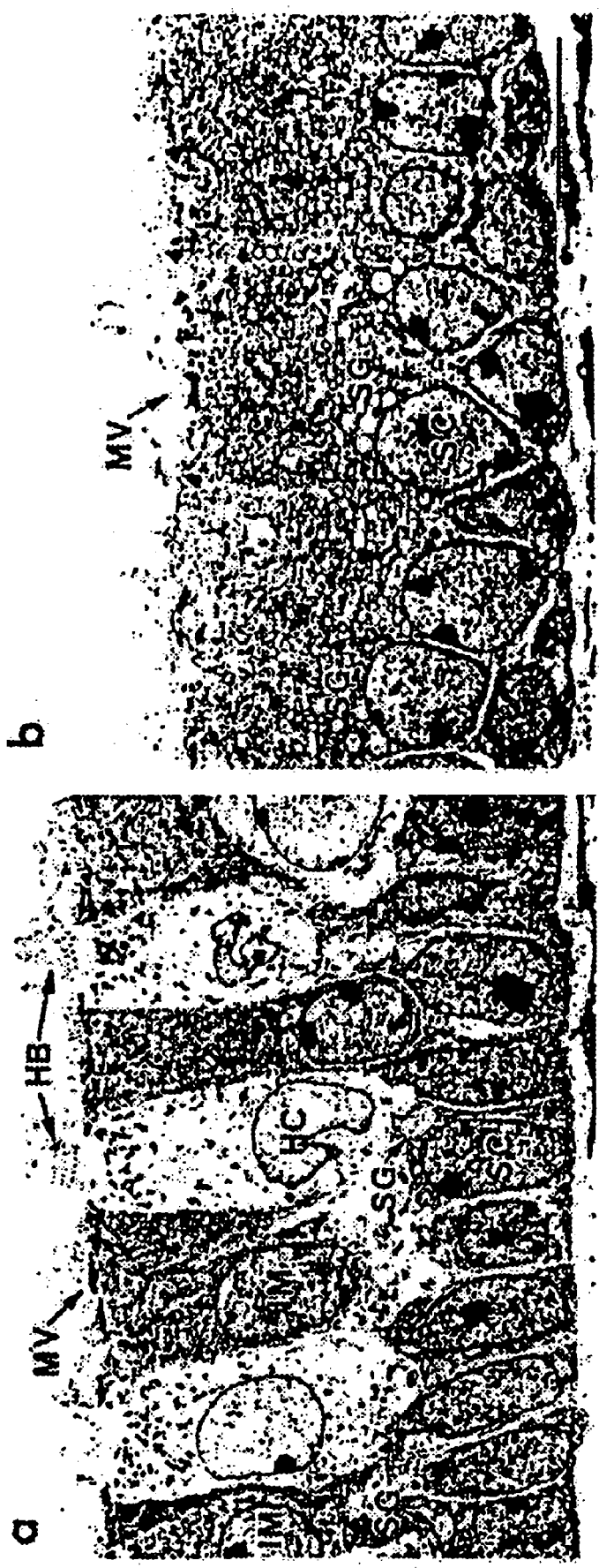
FIGS. 4A and 4B are transmission electron micrographs of E18.5 utricular macula in wild-type and Math1$^{\beta-Gal/\beta-Gal}$ mice.
Figure 5:
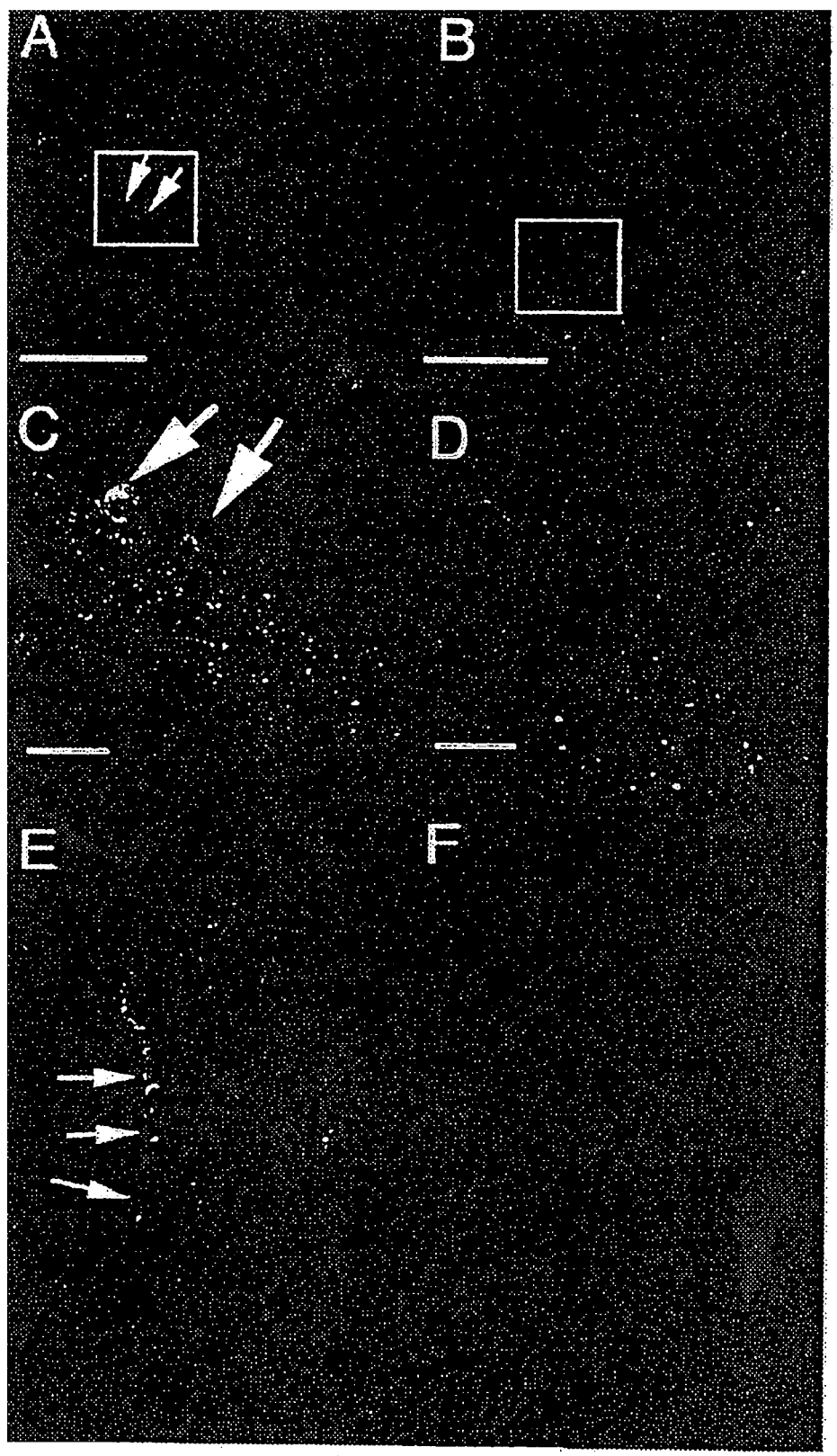
FIGS. 5A through 5F show the Calretinin staining pattern of inner ear sensory epithelia. Sections through the utricle of E16.5 wild-type (FIGS. A5 and 5C) and Math1$^{\beta-Gal/\beta-Gal}$ (FIGS. 5B and 5D) littermates were counterstained with propidium iodide (red) for confocal microscopy. Sections were cut through the crista ampullaris of E18.5 wild-type (FIG. 5E) and Math1$^{\beta-Gal/\beta-Gal}$ (FIG. 5F) were counterstained with DAPI (blue) for immunofluorescent microscopy. The crista is cut at an oblique angle, which accounts for the multiple layers of hair cells in (FIG. 5E). Immunostaining of Calretinin (green, arrows) is evident in hair cells of wild-type (FIGS. 5A, 5C, and 5E) but not null mice (FIGS. 5B, 5D, and 5F). Boxed areas in FIGS. 5A and 5B indicate the regions magnified in FIGS. 5C and 5D. Scale bar equals 100 μm in (FIGS. 5A and 5B), 15 μm in (FIGS. 5C and 5D) and an original magnification of ×200 in (FIGS. 5E and 5F)

Light microscopy revealed that sensory epithelia in null mice are considerably thinner, lack the normal stratification of cell nuclei and stain uniformly, all of which are consistent with the absence of hair cells. TEM clearly distinguishes between hair cells and supporting cells in normal utricles: hair cells have hair bundles, less electron-dense cytoplasm, more apical nuclei, and no secretory granules (FIGS. 4A and 4B). The sensory epithelia of the null mutants lack hair cells entirely but do have supporting cells with normal appearance (Rusch, et al., 1998), including electron-dense cytoplasm, basal nuclei, and secretory granules. However heterozygous Math1$^{+/b\text{-}Gal}$ mice retain hair cells.

EXAMPLE 6

Expression of a Hair Cell Specific Marker in Transgenic Math1 Mice

Lack of hair cells at E18.5 can be due to (1) lack of sensory cell progenitors, (2) the inability of progenitors to differentiate into hair cells, or (3) the inability of hair cells to maintain the differential states, as has been observed in the absence of the POU domain transcription factor Brn3c. The first possibility is unlikely because progenitors give rise to both hair cells and supporting cells. To evaluate the remaining possibilities, the expression of the hair cell specific marker, calretinin and myosin VI were examined. Calretinin is a m ember of the calcium binding family of proteins and is expressed in differentiating hair cells (prior to hair bundle formation) and mature inner ear and auditory hair cells, but not in supporting cells. Calretinin expression in Math1$^{\beta\text{-}Gal/\beta\text{-}Gal}$ and wild-type mice was studied by immunofluorescense on coronal sections of E15.5, E16.5 and E18.5 embryos (FIGS. 5A through 5F).

For immunofluorescence, embryos were fixed for 1.5 hours in 4% paraformaldehyde/PBS at 4° C., sunk through 15% sucrose/PBS for 5 hours then 30% sucrose/PBS overnight, and snap frozen in a 2-methylbutane dry ice bath. 14 μm sections were cut on a cryostat and mounted onto gelatin-coated slides. Sections were fixed onto slides by dipping for 10 minutes in Streck tissue fixative (Streck laboratories) and air drying. Sections were blocked in 30% normal goat serum and 0.3% triton X-100 in PBS for 1 hr at room temperature (RT). Rabbit anti-calretinin polyclonal antibody (Chemicon laboratories) was diluted 1:200 in blocking solution and incubated overnight on sections at 4° C. Sections were washed 3 times (20 minutes each) in Phosphate-Buffered Saline (PBS) at RT. The secondary antibody anti-rabbit antibody, Alexa 488 (Molecular Probes), was diluted 1:400 in blocking solution and used to detect calretinin. Sections were covered and incubated at RT for 2 hours before washing and mounting in Vectashield containing DAPI (Vector). For confocal microscopy, sections were treated with 25 µg/ml RNAse before counterstaining with 50 µg/ml of propidium iodide and mounted in Vectashield without DAPI. Stained sections were viewed under a Bio-Rad 1024 confocal microscope.

Calretinin-positive cells are clearly visible in the sensory epithelia of the semicircular canals and utricles of wild-type mice, but Math1$^{β-Gal/β-Gal}$ embryos lack calretinin expression at all three states. Using the mouse model disclosed herein the present inventors demonstrate that hair cells never develop within the sensory epithelia of Math1$^{β-Gal/β-Gal}$ mice. The presence of the tectorial and otolithic membranes (secreted in part by the supporting cells), together with the TEM results, suggests that the remaining cells in the sensory epithelia of the Math1$^{β-Gal/β-Gal}$ mice are functional supporting cells.

EXAMPLE 7

Math1/lacZ Expression Mimics Math1 Expression in the Developing CNS

Figure 2:
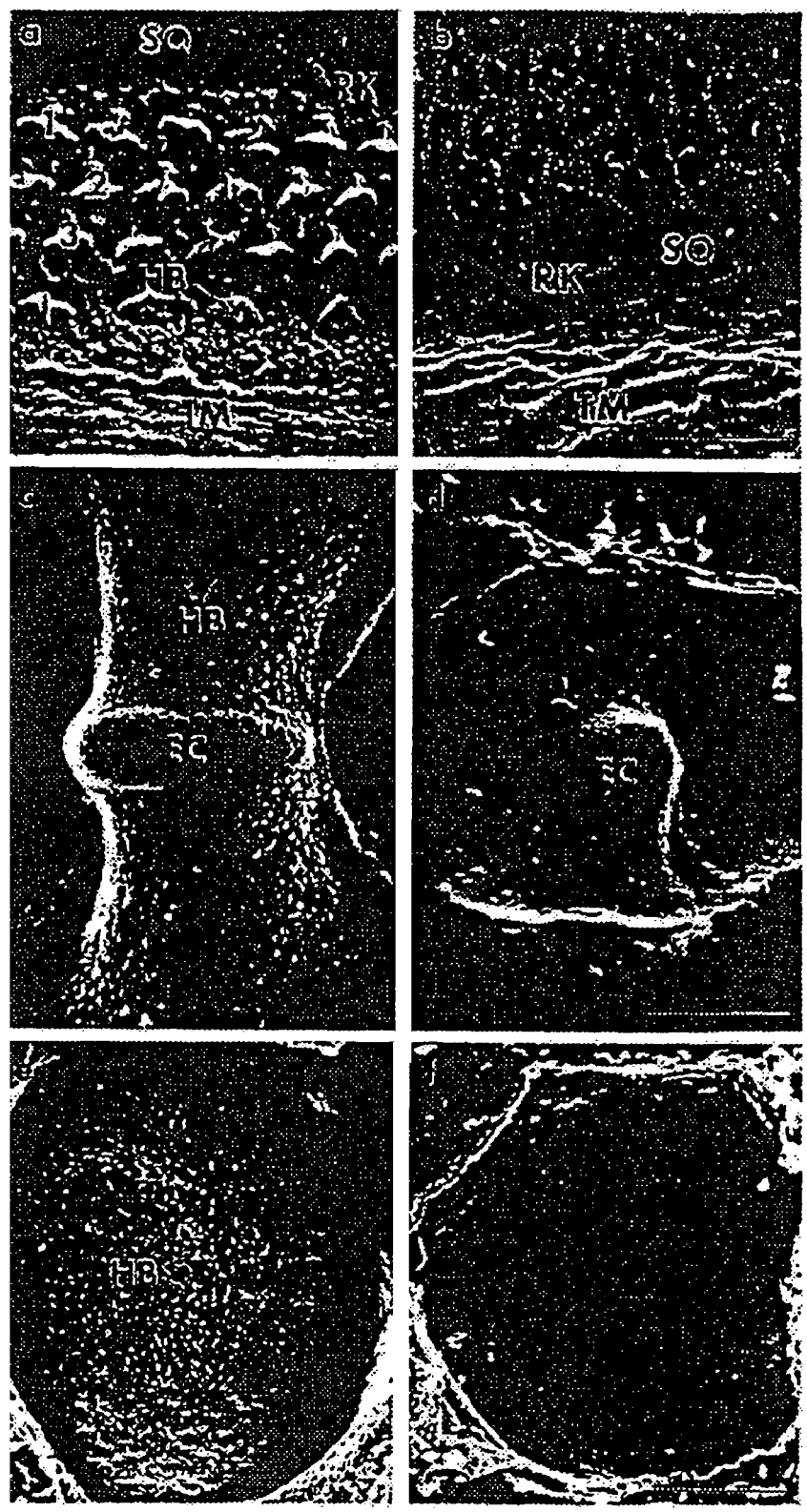
FIGS. 2A through 2F are scanning electron micrographs of E18.5 inner ear sensory epithelia in wild-type and Math1$^{\beta-Gal/\beta-Gal}$ mice. Wild-type mice epithelia are shown in FIGS. 2A, 2C, and 2E and null mouse epithelia in FIGS. 2B, 2D, and 2F. The organ of Corti of the cochlea are shown and indicated in FIGS. 2A and 2B. In the wild-type mouse there are three rows of outer hair cells (1, 2, 3), one row of inner hair cells (I), all with hair bundles (HB). The tectorial membrane (TM), an accessory structure of the cochlea, can be observed at the bottom. Above the sensory epithelium are squamous cells (SQ) with rudimentary kinocilia (RK). In null mice (FIG. 2B), there are only squamous cells. Crista ampullaries of a vertical semicircular canal are depicted in FIGS. 2C and 2D. The null mouse crista is similar to the wild-type in overall shape, including the septum (eminentia) cruciatum (EC), but is smaller. The macula of the uticle is the focus of FIGS. 2E and 2F. Again, the macula of the null mouse is smaller than the wild-type. Scale bars are as follows: 10 μm in FIGS. 2A and 2B, 50 μm in FIGS. 2C and 2D, and 100 μm in FIGS. 2E and 2F.
Figure 3:
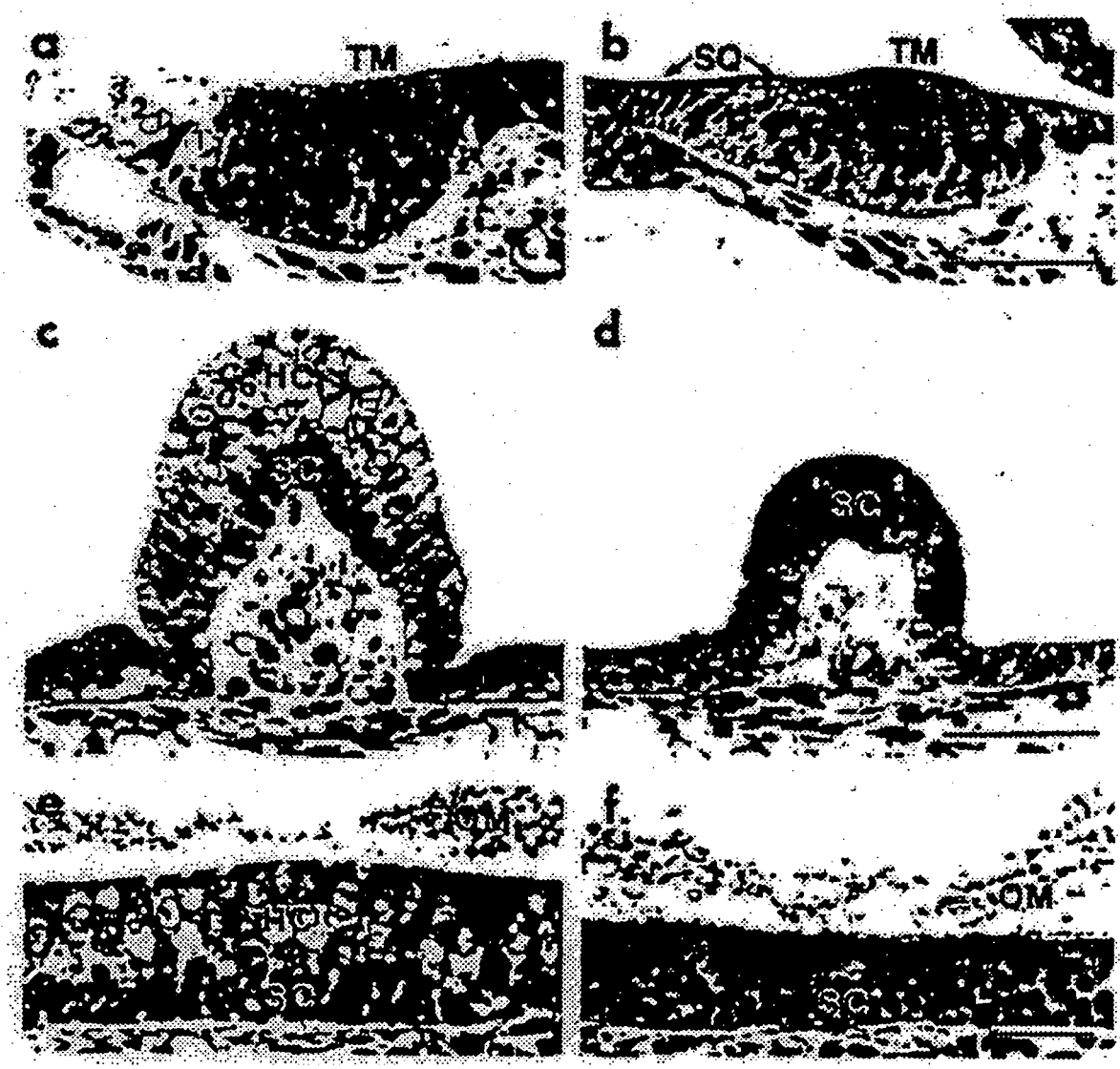
FIGS. 3A through 3F are light micrographs of semi-thin transverse sections of inner ear sensory epithelia in wild-type mice (FIGS. 3A, 3C, and 3E) and Math1$^{\beta-Gal/\beta-Gal}$ (FIGS. 3B, 3D, and 3F), all mice were observed at E18.5. As observed in the cochlea of wild-type mice, FIG. 3A, three outer hair cells (1, 2, 3) and one inner (I) hair cell are present. Conversely, the null mouse cochlea (FIG. 3B) has only squamous cells (SQ) in the same region. Hair cells (HC) and supporting cells (SC) are present in the wild-type crista ampullaris (FIG. 3C) and utricular macula (FIG. 3E), but only supporting cells are present in null mice (FIGS. 3D and 3F). The crista was cut obliquely, accounting for the multiple layers of hair cells in FIG. 3C. The otolithic membrane (OM), an accessory structure of the utricle, is present in both wild-type mice (FIG. 3E) and null mice (FIG. 3F). Scale bars equal 100 μm in (FIGS. 3A and 3B); 50 μm in (FIGS. 3C and 3D); and 25 μm in (FIGS. 3E and 3F).
Figure 8:
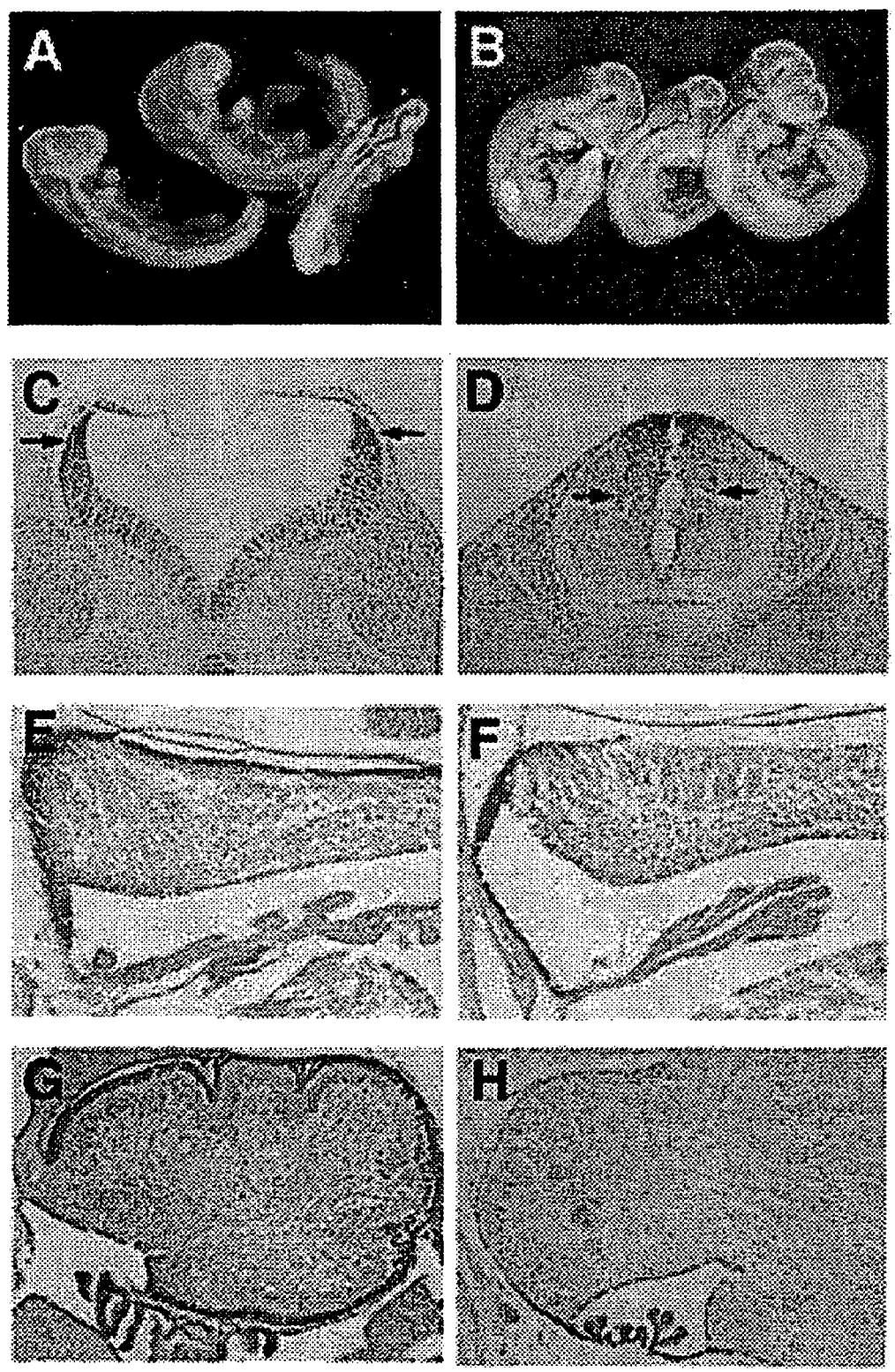
FIGS. 8A through 8H show Math1/lacZ expression and cerebellar phenotype in Math1$^{+/b\text{-}gal}$ and Math1$^{b\text{-}gal/b\text{-}gal}$ mice.

The developing cerebellum at E14.5 and postnatal day 0 (P0) in Math1$^{+/b-gal}$ and Math1$^{b-gal/b-gal}$ mice were analyzed by RNA in situ hybridization analysis. The analysis showed that the expression pattern of the lacZ gene faithfully reproduced the Math1 expression pattern observed by RNA in situ hybridization analysis shown previously (Akazawa et al., 1995; Ben-Arie et al., 1996) (FIGS. 2A, B, E, G). Moreover, the cerebellar phenotype in Math1$^{b-gal/b-gal}$ mice (FIGS. 8F and 8H) was identical to that observed in Math1 null mice (Ben-Arie et al., 1997). At E14.5, the precursors of the EGL are present in the rhombic lip from which they migrate over the cerebellar anlage to populate the EGL (FIG. 8E). Mutant mice displayed far fewer of these cells than heterozygous mice (FIG. 8F). At P0, the neurons of the external granule layer (EGL) were completely lacking (FIG. 8H).

Math1/lacZ expression in the developing hind brain and spinal cord similarly reproduced the expression pattern of Math1 (FIGS. 8C, 8D). The only notable difference between the expression patterns established by in situ hybridization and lacZ staining is that b-galactosidase expression persists in differentiating or migrating cells of the spinal cord because of the stability of the b-GAL protein (FIG. 8D). In summary, the neural tissue expression pattern and cerebellar phenotype associated with the replacement of the Math1 coding region by lacZ is consistent with previously published data on Math1 expression (Akazawa et al., 1995; Ben-Arie et al., 1997; Ben-Arie et al., 1996; Helms and Johnson, 1998), demonstrating that the endogenous control elements were not disrupted by insertion of the lacZ gene. Moreover, many previously undetected clusters of lacZ-expressing cells became apparent upon X-gal staining of whole embryos and sections in Math1$^{+/b-gal}$ mice (see below). It is likely that limitations in the spatial resolution of RNA in situ hybridization techniques used to detect the transcript in earlier studies prevented these sites of expression from being discerned (Akazawa et al., 1995; Ben-Arie et al., 1996). Alternatively, the stability of the lacZ gene product and the increased sensitivity due to signal amplification allowed us to identify sites of relatively low expression levels.

EXAMPLE 8

Math1/lacZ is Expressed in Inner Ear Sensory Epithelia

Figure 9:
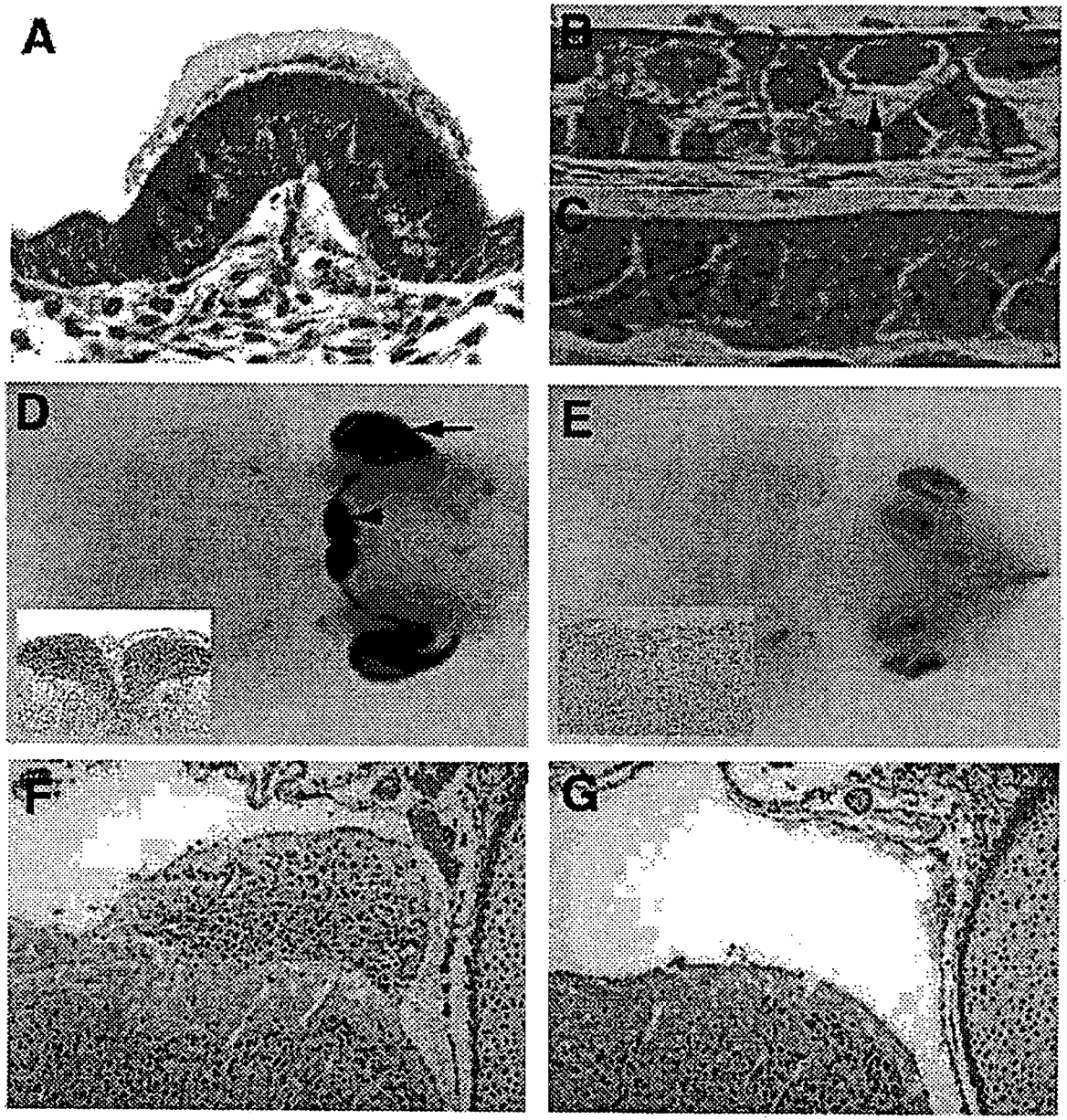
FIG. 9A through 9G shows expression of Math1/lacZ in the inner ear and brain stem and histological analysis of ventral pontine nucleus. X-gal staining of E18.5 Math1$^{+/b\text{-}gal}$ utricular crista (FIG. 9A) and inner ear sensory epithelia of Math1$^{+/b\text{-}gal}$ (FIG. 9B) and Math1$^{bgal/bgal}$ (FIG. 9C). The Math1/lacZ expression in the upper hair cell layer of the sensory epithelia of (FIGS. 9A and 9B) and the characteristic calyx appearance (arrowhead). In the null mice X-gal staining of epithelial cells is non-specific in the absence of hair cells (FIG. 9C). Whole-brain X-gal staining of Math1$^{+/b\text{-}gal}$ (FIG. 9D) and Math1$^{bgal/bgal}$ (FIG. 9E) at E18.5 is demonstrated. There is positive staining of the pontine nucleus (arrowhead) and cerebellum (arrow) in Math1$^{+/b\text{-}gal}$ mice, which is lacking or greatly reduced in null mutants in both the cerebellum, and pontine nucleus (inset).

The sensory organs of the inner ear were among the newly identified sites of Math1/lacZ expression, demonstrated utilizing the methods described in Example 2. Expression in the otic vesicle was first detected at E12.5 and continued until E18.5 throughout much of the sensory epithelia (Bermingham et al., 1999) (FIGS. 9A, 9B). Null mutants displayed Math1/lacZ expression in the inner ear throughout embryogenesis (FIG. 9C). Math1 null mutants lack hair cells in all of the sensory organs (Bermingham et al., 1999), but maintain supporting cells, the other sensory epithelia-derived cells (FIG. 9C). These supporting cells seem to be functional, based on their morphology and the presence of overlying membranes secreted in part by these cells. Although the expression of Math1 in inner ear sensory epithelia was not demonstrated by RNA in situ hybridization analysis, the complete lack of inner ear hair cells in the null mutants leaves little doubt about the authenticity of the Math1/lacZ expression pattern.

Math1 is clearly essential for hair cell development in the inner ear. Its expression pattern and in vivo function are akin to those of Math1's proneural homolog, atonal (ato) (A. P. Jarman, Y. Grau, L. Y. Jan, Y. N. Jan, Cell 73, 1307-21 (1994)). ato is expressed in a ring of epithelial cells within the antennal disc of *Drosophila*. Some of these epithelial cells will subsequently develop into mechanoreceptors in the Johnston organ, which is necessary for hearing and negative geotaxis. It is interesting to note that mechanoreceptor progenitor cells are absent in ato mutants, whereas only the mechanoreceptors, and not their progenitors, are absent in Math1 null mice.

Based on the observations made herein, the present inventors have recognized that Math1 is required for the specification of inner ear hair cells. In a sense, Math1 acts as a "pro-hair cell gene" in the developing sensory epithelia. In conjunction with two recent studies, the present inventors have recognized that the results provided herein provide evidence supporting a lateral inhibition model for the determination of hair cells and supporting cells (Haddon et al., 1998; Adam, et al., 1998), in which the interplay of Delta, Notch, and Serrate1 results in the selection of individual hair cells from clusters of competent cells. Such a model entails that the sensory epithelia express a "pro-hair cell gene" whose function is essential for hair cell fate specification.

The ectopic expression of ato in the fruitfly and its homolog Xath1 in *Xenopus* (Kim et al., 1997) can recruit epithelial cells into specific neuronal fates, and the expression of Math1 in inner ear epithelia strongly suggests loss of a functional Math1 gene is likely to be a common cause of deafness and vestibular dysfunction.

EXAMPLE 9

Math1/lacZ is Expressed in Brain Stem Nuclei

In the brainstem Math1/lacZ staining appeared from E18.5 to P7 in the ventral pons in the regions corresponding to the pontine nuclei (FIG. 9D and inset). This finding is consistent with the hypothesis of Akazawa and colleagues that Math1-positive cells in the developing hind brain are precursors to the bulbopontine neurons (Akazawa et al., 1995). No such staining appeared in the null mutants (FIG. 9E and inset). These data raise the possibility that the absence of lacZ staining in pontine nuclei can be due to failure of their precursors to migrate, proliferate, and/or differentiate. Ventral pontine nuclei were examined upon haematoxylin and eosin staining of sections and were found to be missing in the brain stem of null mice (FIGS. 9F, G). Furthermore, the failure of null mouse newborns to breathe can be due to absence of these brainstem neurons.

EXAMPLE 10

Math1/lacZ is Expressed in Chondrocytes

Figures 6A, 6B:
FIGS. 6A and 6B show the expression pattern of Math1 in mouse articular cartilage using the Math1$^{+/\beta\text{-}Gal}$ heterozygote.

Math1$^{+/b\text{-}Gal}$ heterozygotes displayed expression of Math1 in articular cartilage (FIGS. 6A and 6B). FIG. 6A demonstrates expression in all joints of a forelimb. Upon closer examination of an elbow joint, Math1 is noted to be expressed exclusively in the non-ossified articular chondrocytes.

Figure 10:
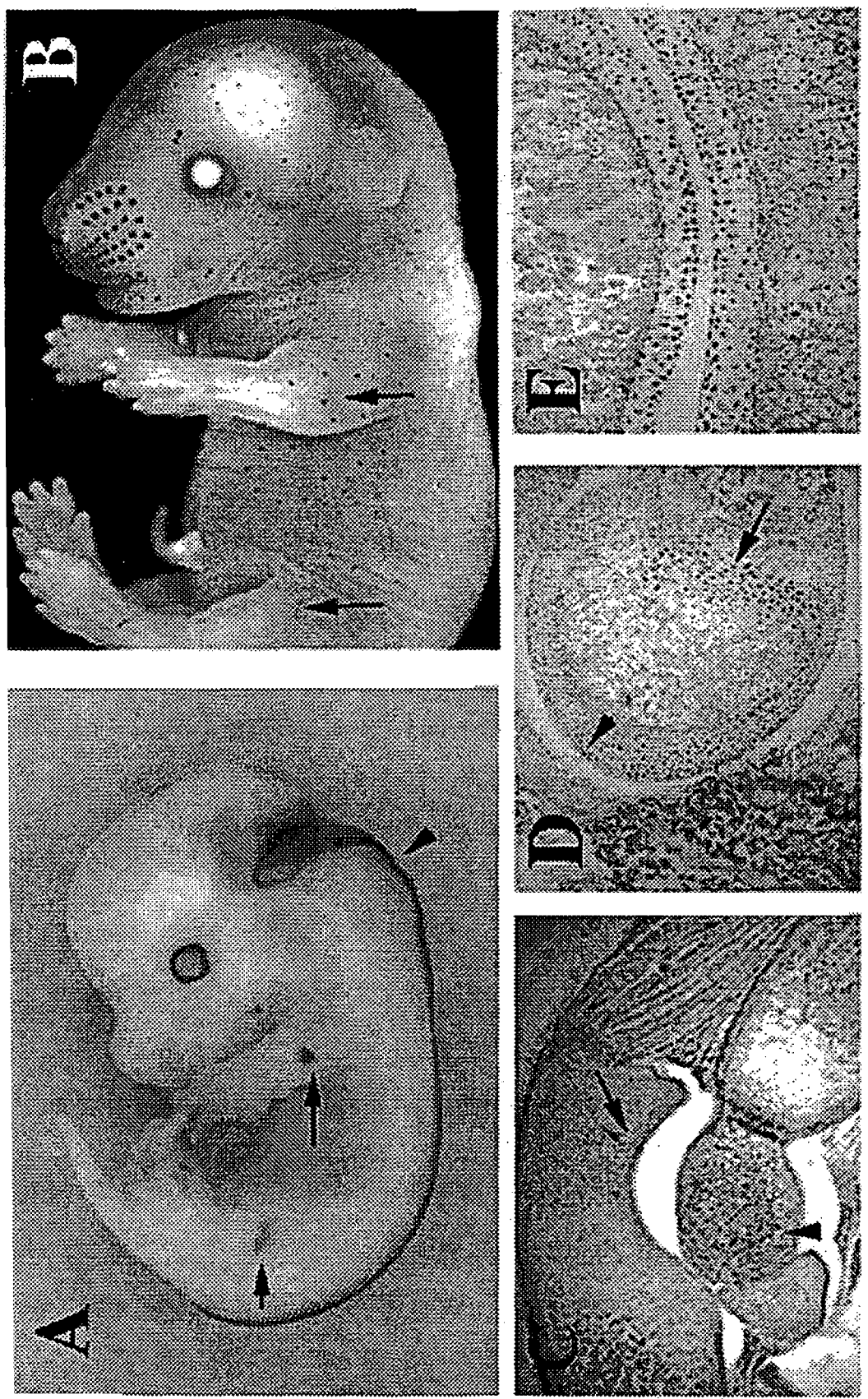
FIGS. 10A through 10E demonstrate Math1/lacZ is expressed in joint chondrocytes. X-gal staining of whole embryos at (FIG. 10A) E12.5 and (FIG. 10B) E16.5 illustrates that Math1/lacZ is expressed in all joints (FIG. 10C). Horizontal section through the elbow joint of E18.5 Math1$^{+/b\text{-}gal}$ mouse shows that it is expressed in resting chondrocytes (arrow).

Expression of Math1/lacZ was detected in the developing proximal joints, such as those of the hip and shoulder, as early as E12.5 (FIG. 10A). X-gal positive staining was detected at subsequent developmental stages in a progressive proximal-distal pattern that paralleled the normal development of joints (FIG. 10B). In the joints, Math1/lacZ expression immediately follows mesenchymal condensation, which begins at E11.5. Condensed mesenchyme cells differentiate into chondrocytes (Bi et al., 1999; Horton et al., 1993; Karsenty, 1998).

Chondrocytes differentiate in three major phases during bone formation: resting, proliferating and hypertrophic. The resting chondrocytes that populate the articular cartilage are referred to as articular chondrocytes (Buckwalter and Mankin, 1998; Poole, 1997). Prior to birth, resting chondrocytes constitute the entire chondrocyte population in joints. To establish which cells expressed Math1/lacZ, sections from E18.5 and P7 Math1$^{+/b\text{-}gal}$ mice were stained with X-gal. Math1/lacZ is expressed in the resting chondrocytes of all joints analyzed at E18.5; resting chondrocytes in the elbow joint are shown in FIG. 10C, and FIG. 10D shows the resting, proliferating, and articular chondrocytes of a P7 mouse.

The joints of E18.5 embryos were examined with anti-MATH1 antibody prepared by the following methods. An EcoR I-Hind III fragment encoding the N-terminal 156 amino acids of the Math1 open reading frame (Math1D) was cloned into the pET 28a+ expression vector (Novagen). Math1D fragment was expressed as a His tag fusion protein. Soluble MATH1D protein was purified according to His-tag kit specifications (Novagen) and 2 mg of protein were used to immunize Chickens (Cocalico Biologicals Inc.).

Expression was found in resting chondrocytes, whereas no expression was observed in null embryos. It should be noted that not all articular cartilage cells express Math1/lacZ (FIG. 10E). Math1/lacZ expression in Math1 null mutants is similar to that in heterozygous mice at E18.5, suggesting that Math1 is not required for resting chondrocyte development.

EXAMPLE 11

Math1/lacZ is Expressed in Merkel Cells

By E14.5 Math1/lacZ-positive cells were apparent around the vibrissae and in the skin of much of the body (FIG. 10B). In the trunk, the stained cells were arranged in a striped pattern defined by the epidermal ridges. This staining was apparent only in the hairy, not the glabrous, skin. All the primary (mystical) vibrissae, including the lateral nasal, maxillary and four large hairs, were positive for Math1/lacZ. Staining was also detected in the secondary vibrissae, including the labial, submental, rhinal, and isolated orbital vibrissae (supra-, infra- and post-orbital) (Yamakado and Yohro, 1979). By E15.5 staining appeared in clusters of cells in the foot pads (FIG. 10B).

Figure 11:
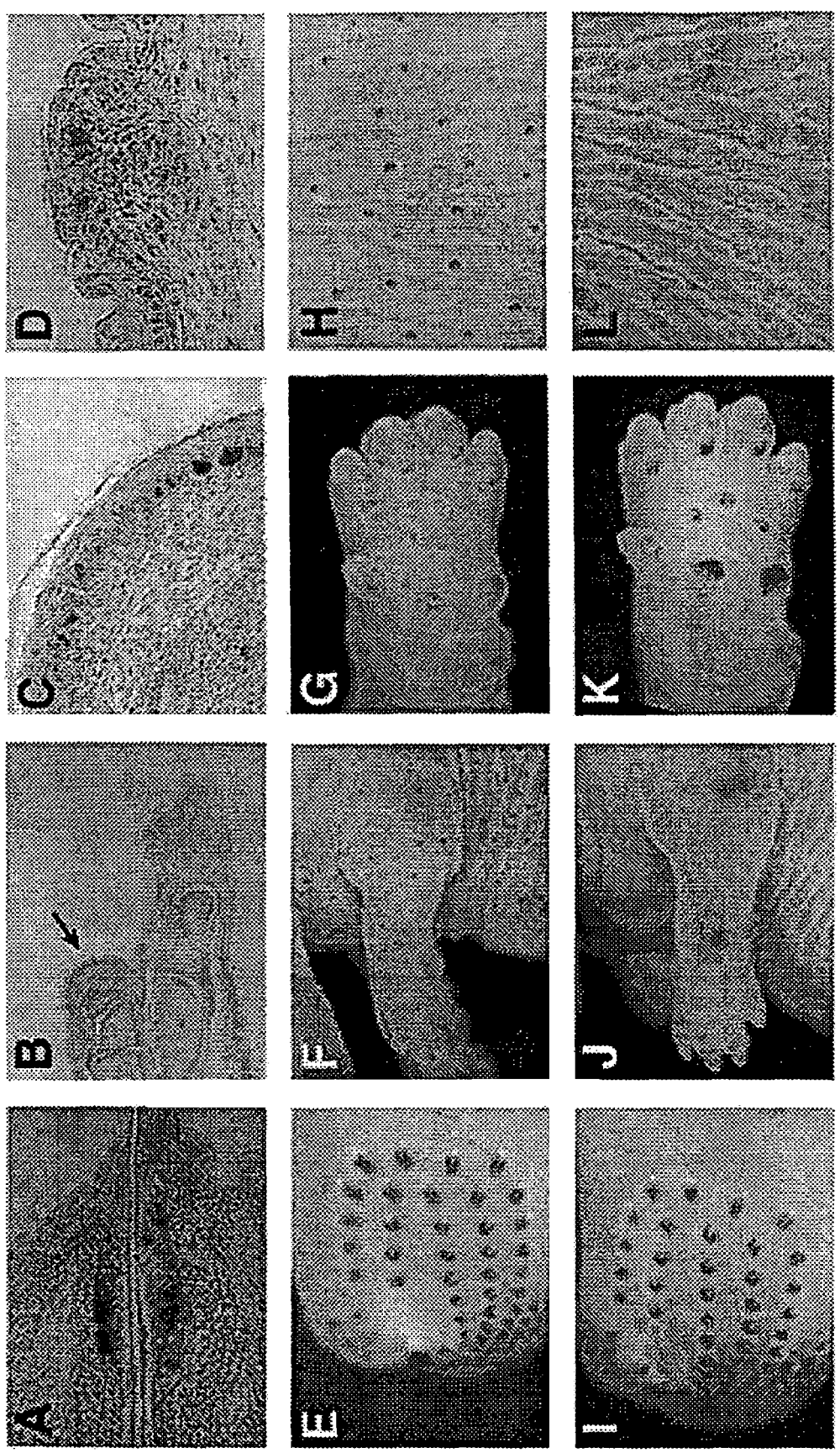
FIGS. 11A through 11L show Math1/lacZ expression in Merkel cells. To identify the structures stained on the hairy and non-hairy skin, E16.5 littermate embryos were stained as whole mounts, sectioned, and microscopically examined. Shown are sections through the vibrissae (FIG. 11A), foot pad at low (FIG. 11B) and high magnification of the region marked by an arrow in B (FIG. 10C), and hairy skin (FIG. 11D). In all sections the localization of the stained cells was as expected from Merkel cells. To look for macroscopic defects in null mice, close-up pictures were taken through a stereomicroscope of Math1$^{+/b\text{-}gal}$ (control, panels E-H) and Math1$^{b\text{-}gal/b\text{-}gal}$ (null, panels I-L) littermate mice. Staining in null mice appeared stronger because of a dosage effect in the vibrissae (E, I), limb joints (F, J), and foot pads (G, K). In contrast, the staining intensity of null (J, L) mice was markedly weaker than that of heterozygous (F, H) mice in the touch domes associated with the hairy skin. The original magnification is was follows: A×200; B×50; C×400; D×500; E-G-H-I-K-L×32; F-J×16.

To identify the Math1/lacZ-positive cells in the vibrissae, footpad, and hairy skin, we examined histological sections from Math1$^{+/b\text{-}gal}$ mice (FIG. 11A-D). Sections through the vibrissae showed that the stained cells are localized to the more apical half of the hair shaft, but are not in the hair itself. Cross sections through the foot pad illustrated staining of cluster of cells in the epidermal layer (FIGS. 11B,C). As shown in FIG. 11D, sections through the truncal skin identified clusters of Math1/lacZ-stained cells. The stained cells were arranged in a horseshoe-shaped pattern centered within an elevated button-like structure in the hairy skin. These button-like structures were identified as touch domes or Haarscheiben (Pinkus, 1905), which are characterized by a thickened epidermis and an elevated dermal papilla with a capillary network. Touch domes are associated with large guard hairs dispersed between other hair types in the coat. The spatial distribution of Math1/lacZ-stained cells, the timing of their appearance at E14.5, and their localization within the mystical pads of the vibrissae and the touch domes in the hairy skin suggest that these cells correspond to Merkel cells, specialized cells in the epidermis that form slow-adapting type I mechanoreceptor complexes with neurites (Munger, 1991).

The results of comparative analysis of the Math1/lacZ expression pattern in heterozygous and homozygous E16.5 animals are shown in FIG. 11E-L. Math1$^{b\text{-}gal/b\text{-}gal}$ embryos displayed a staining pattern similar to that of Math1$^{+/b\text{-}gal}$ littermates in the vibrissae and footpads (FIG. 11E-G, I-K). In contrast, staining in the touch domes of the hairy skin was barely detectable in Math1$^{b\text{-}gal/b\text{-}gal}$ embryos (FIGS. 11H,L). The reduction of staining in null animals was also obvious at E18.5.

To further define Math1/lacZ-positive cells in the skin, Math1$^{+/b\text{-}gal}$ mice were mated to Tabby mice. Tabby (Ta) is a spontaneous X-linked mutation displaying a similar phenotype in hemizygous males and homozygous females (Ferguson et al., 1997). Tabby mutants lack hair follicles (tylotrich), a subset of Merkel cells that are associated with touch domes in the hairy skin of the trunk (Vielkind et al., 1995), and some of the five secondary vibrissae on the head (Gruneberg, 1971). Hence, in a cross of Ta/Ta females with a heterozygous Math1$^{+/b\text{-}gal}$ male, 50% of the male progeny are Ta/Y: Math1$^{+/b\text{-}gal}$, allowing us to assess whether the Math1/lacZ-positive cells correspond to Merkel cells.

Ta/Ta females were time-mated with Math1$^{+/b\text{-}gal}$ males, and embryos were harvested at E16.5. Each pup's gender was determined by PCR on tail DNA, using primers (forward 5'-TGAAGCTTTTGGCTTTGAG-3'; SEQ ID NO:67, and reverse 5'-CCGCTGCCAAATTCTTTGG-3'; SEQ ID NO:68) that yielded a 320 bp product from chromosome X, and a 300 bp product from chromosome Y (Liu et al., 1999). Amplification conditions were: 92° C./1 min, 55° C./1 min, 72° C./1 min for 32 cycles, with an initial denaturation step of 94° C./7 min and last extension step of 72° C./7 min. Amplification products were separated on 2% agarose gels. X-gal-stained embryos were scored independently by 2 individuals, and only then were results matched with the determined gender.

Figure 12:
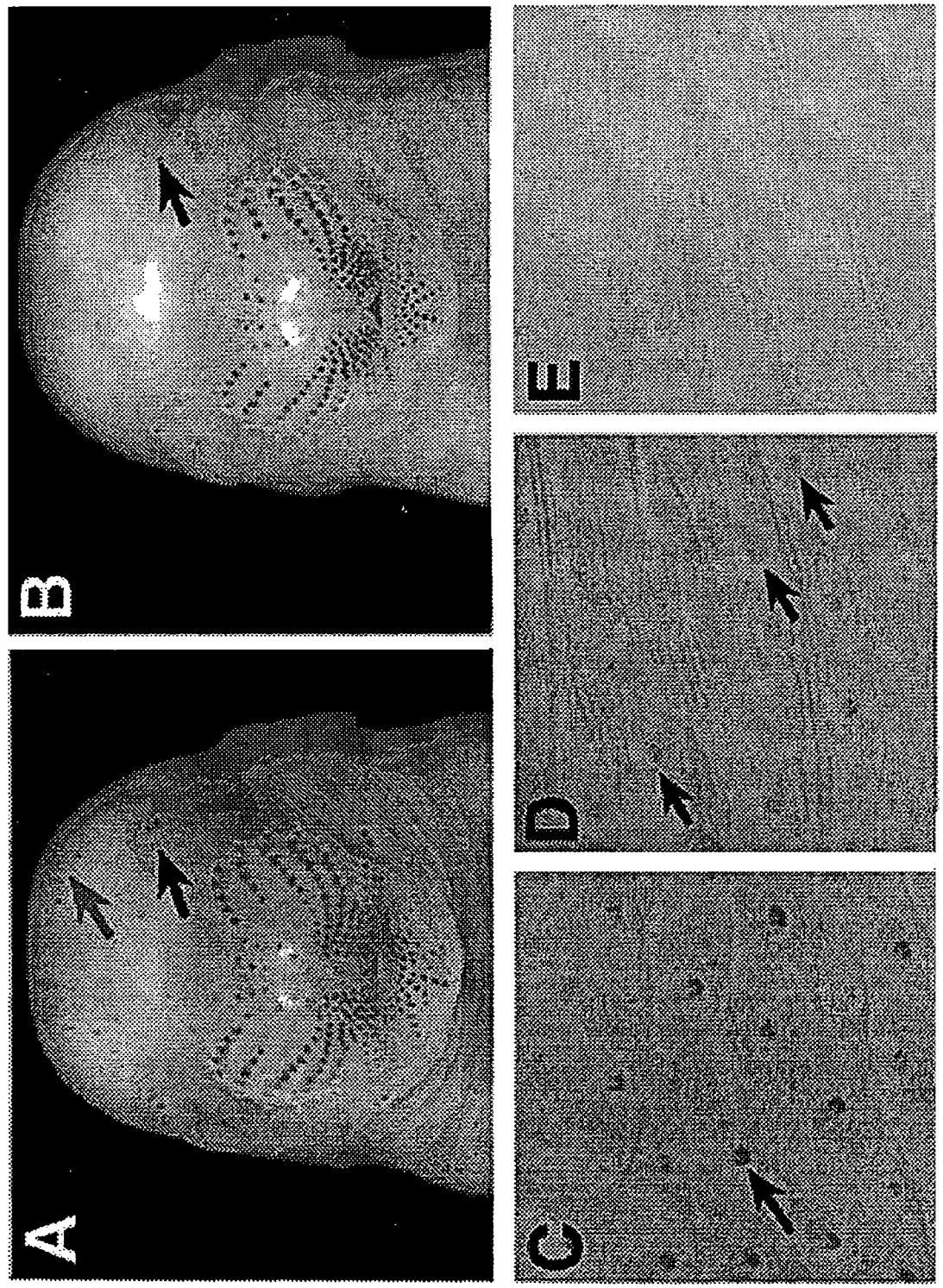
FIGS. 12A through 12E show lack of lacZ-stained touch domes in Tabby mice. Tabby/Tabby females were crossed with Math1$^{+/b\text{-}gal}$ males, and their progeny were X-gal stained and gender-determined at E16.5. Staining around primary vibrissae in the snout was detected in both female embryos heterozygous for the Tabby mutation (FIG. 12A) and male embryos hemizygous for the mutation (FIG. 12B). Secondary vibrissae, which are known to vary in number in the Tabby mutants (black arrows), were also stained. The staining of the touch domes was less intense in the Tabby/X female (FIG. 12D) than Math1$^{+/b\text{-}gal}$ (wt for Tabby) embryos (FIG. 12C), since Tabby is a semidominant mutation. However, patches of stained touch domes were detected in a female embryo that carried a wild-type allele at the Tabby locus (FIG. 12A, red arrow, and 12D). In contrast, a hemizygous male completely lacked both staining and touch domes, due to the loss of hair follicles that abolishes the development of Merkel cells (FIGS. 12B and 12E).

Both Tabby females and males carrying the Math1$^{+/b\text{-}gal}$ allele displayed X-gal staining in the vibrissae and foot pads (FIGS. 12A,B). The effect of the Tabby mutation on the number of secondary vibrissae was quite clear: hemizygous males completely lacked Math1/lacZ-positive cells in the secondary vibrissae (typically lacking in Ta mutants) and on the trunk (FIG. 12E). Females that are heterozygous for Tabby showed patchy staining in the touch domes (although less than wt), as should be anticipated in female carriers of a mutation in a gene that undergoes random X chromosome inactivation (FIGS. 12C,D). The localization and distribution of the positive cells, as well as their absence in selected vibrissae and the trunk of Tabby males, strongly indicate that Math1 is expressed in the Merkel cells associated with guard follicles in the touch domes of the hairy skin.

Figure 13:
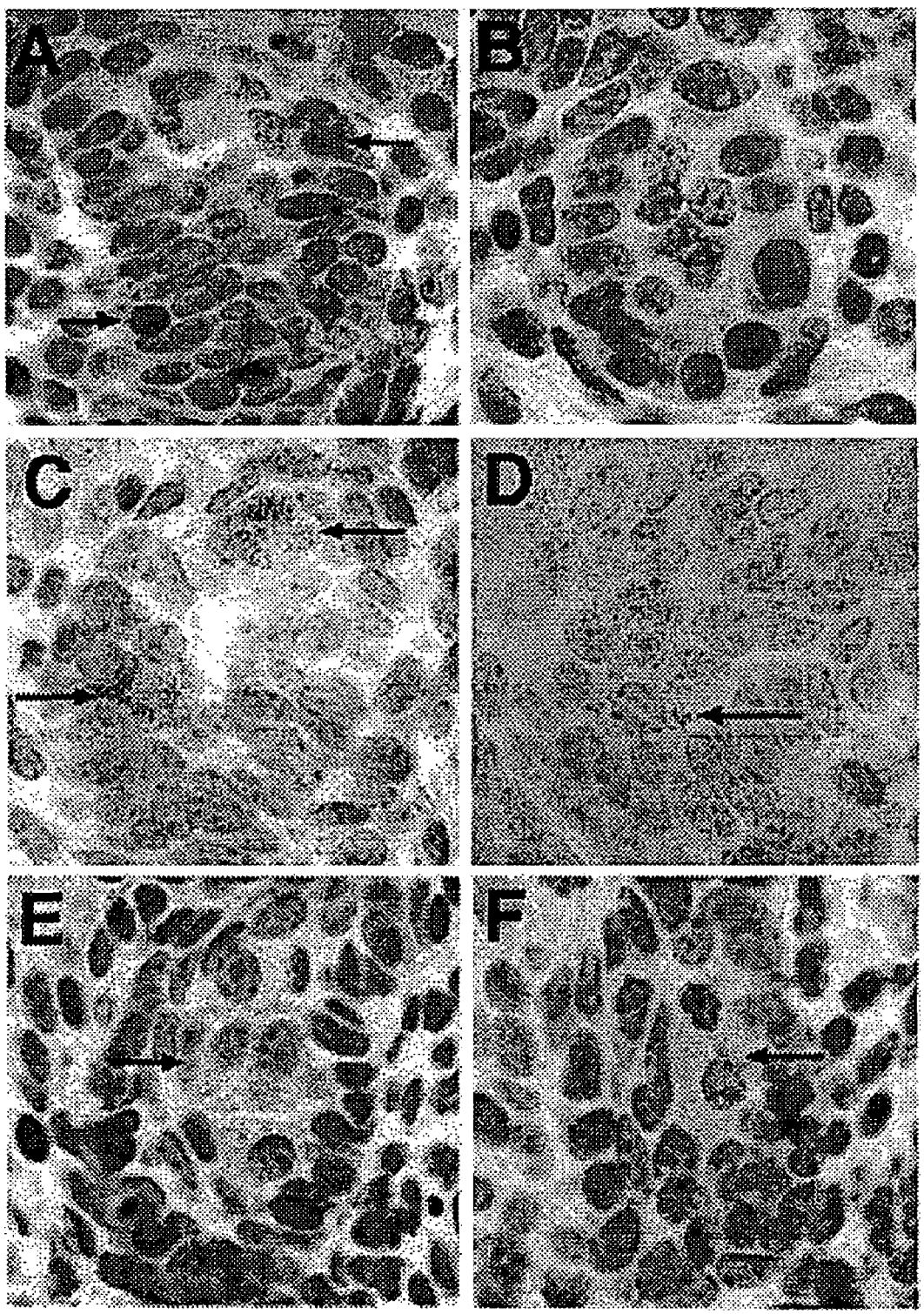
FIGS. 13A through 13F demonstrate marker analysis of Merkel cells in wild type and Math1 null mice. Skin sections from Math1$^{+/+}$ and Math1$^{b\text{-}gal/b\text{-}gal}$ reacted with antibodies against MATH1 (FIGS. 13A and 13B), cytokeratin 18 (FIGS. 13C and 13D), and chromogranin A (FIGS. 13E and 13F). Polyclonal antibodies to MATH1 identify multiple basal nuclei in rare abdominal hair follicles of wild type (FIG. 13A) but not mutant mice (FIG. 13B). Monoclonal antibodies to cytokeratin 18 and chromogranin A identify Merkel cells in both wild type (FIGS. 13C and 13E) and mutant (FIGS. 13D and 13F) mice. The original magnification was 100×.

To ascertain whether Math1/lacZ staining pattern reflects normal Math1 expression pattern, immunohistochemical analysis of MATH 1 was performed on sections from abdominal skin (see Example 2). As seen in FIGS. 13A and B, MATH1-positive cells were detected around the hair follicles of Math1$^{+/+}$ but not Math1$^{b-gal/b-gal}$ mice. Antibodies against two Merkel cells markers were chosen for further analysis: anti-cytokeratin 18, expressed in simple epithelia, and chromogranin, localized to secretory granules of neuroendocrine, endocrine, and neuronal tissues. Both cytokeratin 18 (FIGS. 13C,D) and chromogranin A (FIGS. 13E,F) confirmed the identity of the Math1/lacZ-positive cells as Merkel cells, but did not reveal staining abnormalities in Math1$^{b-gal/b-gal}$ mice. Thus, Math1 does not seem to be essential for the genesis of the neuroendocrine Merkel cells, in contrast to pure neuronal cell types like cerebellar EGL and pontine nuclei. Because Math1 null mutants die at birth, we can not assess whether the entire cluster of Merkel cells is formed or the functional integrity of Merkel cells in these mutants is affected.

EXAMPLE 12

Math1 Partially Rescues Chinese Hamster Ovary Cells (CHO) in Flies Deleted for ato This Example demonstrates that atonal-associated genes can induce the development of CNS cells in animals deficient in a native atonal-associated gene or gene product. This Example also demonstrates that atonal-associated genes can therapeutically function in species in which they are not natively expressed.

Given the remarkable similarity in expression patterns of ato and Math1, and their identical basic domains, Math1 was tested to see if it would mimic the effects of ato overexpression by producing ectopic chordotonal organs as described by the following methods. Wild-type, also known as yw flies, were transformed with a UAS-Math1 construct as described (Brand and Perrimon, 1993). To overexpress Math1 in wild type flies, yw; UAS-Math1 flies were mated to HS-Gal4 flies. The progeny were heat shocked as previously described (Jarman et al., 1993). To rescue the loss of chordotonal organs in ato mutant flies, w; UAS-Math1/UAS-Math1; ato1/TM6 flies were crossed to w; HS-Gal4/CyO; ato1/TM6 flies. Embryos were collected for 3 hr., aged for 3 hr., heat shocked for 30 min. at 37° C. and allowed to develop for the next 12-15 hr. Embryos were fixed in 4% formaldehyde in PBS with 50% heptane. Embryos were washed with 100% ethanol, transferred to PBT and stained with mAb 22C10 as previously described (Kania et al., 1995) to detect PNS neurons. Chordotonal neurons were identified by their distinct morphology and position.

Figure 14:
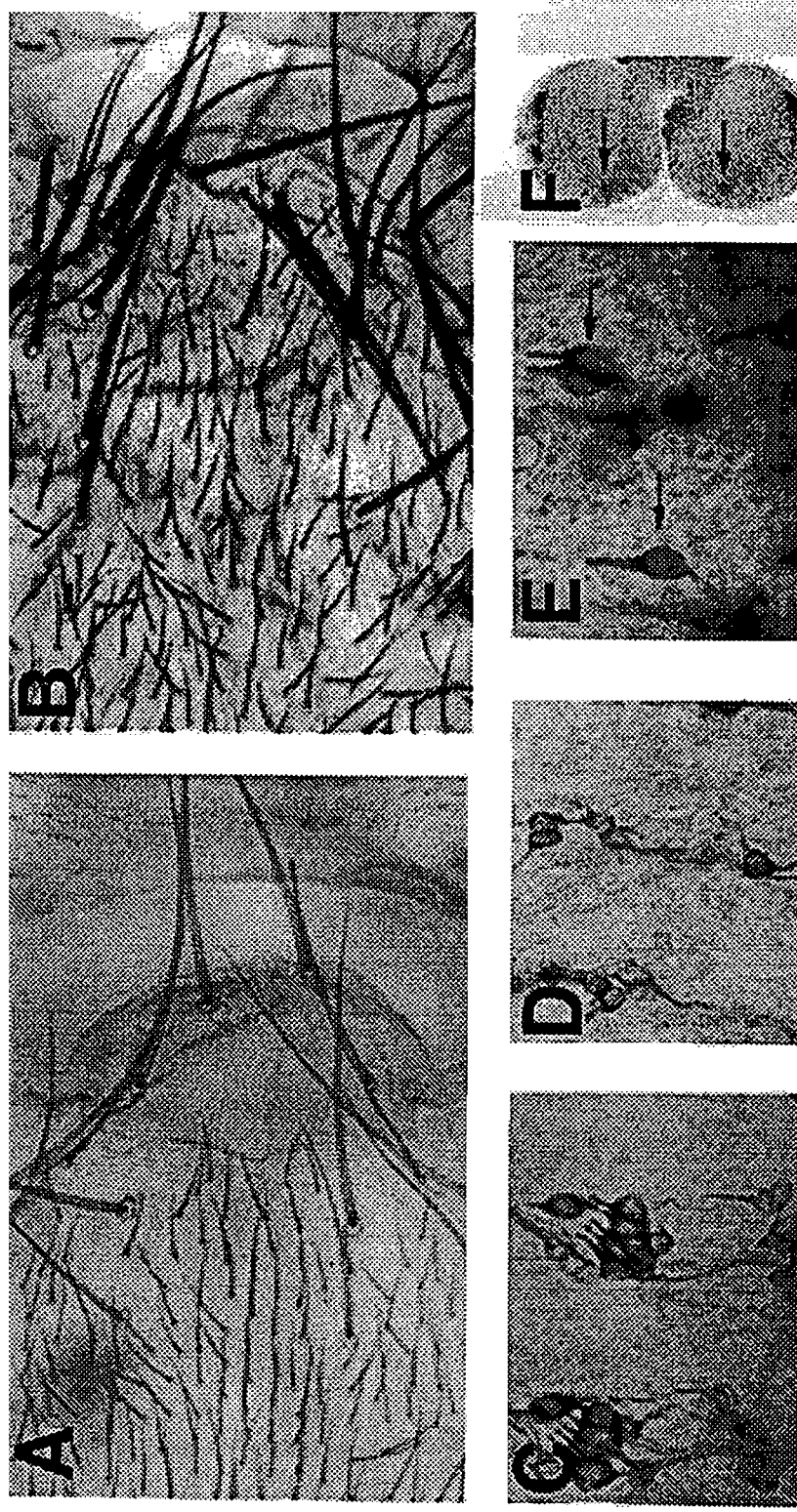
FIGS. 14A through 14G show Math1 rescues the lack of chordotonal neurons in *Drosophila ato* mutant embryos.

Expressing Math1 during pupal development by heat shock using the UAS-Gal4 system (Brand and Perrimon, 1993) resulted in supernumerary external sense organs on the notum (FIGS. 14A,B) and the wing blade, as reported for ato (Jarman et al., 1993),and the Achaete-Scute complex (AS-C) genes (Brand and Perrimon, 1993; Rodriguez et al., 1990). Math1 expression in flies, like ato, produced ectopic chordotonal organs (FIG. 8G), although with less efficiency. Overexpression of the AS-C genes does not, however, result in ectopic chordotonal organs (Jarman et al., 1993). Math1 thus has a similar functional specificity to ato.

Since several ato enhancers are ato-dependent (Sun et al., 1998), they can be activated by Math1, which would then lead to ectopic CHO specification. To determine whether Math1 can substitute for ato function in the fly, and to rule out the possibility that production of CHOs by Math1 is due to ato activation, Math1 was expressed in ato mutant embryos. The mutants lack all chordotonal neurons (FIG. 14C), but overexpressing Math1 partially rescues the loss of these neurons (FIG. 14D) in a manner similar to ato (Chien et al., 1996).

EXAMPLE 13

Significance of Atonal and Math1 in the CNS and PNS

Over the past few years significant progress has been made towards unraveling the roles of bHLH proteins in vertebrate neurogenesis. Neural vertebrate bHLH-encoding genes were isolated and characterized because *Drosophila* homologues such as ato or the AS-C genes had been previously shown to be required for neurogenesis (Anderson, 1995; Guillemot, 1046 1995; Lee, 1997; Takebayashi et al., 1997). Indeed, several genes were shown to be proneural because their absence caused a failure of neuroblast or sensory organ precursor (SOP) specification, whereas their overexpression lead to the recruitment of supernumerary neuronal precursors (Ghysen and Dambly-Chaudiere, 1989). With the exception of neurogenin (Ngn) 1 and 2 (Fode et al., 1998; Ma et al., 1998), it remains uncertain which of the vertebrate homologues play roles similar to their *Drosophila* counterparts, and what precise role different bHLH proteins play in neural development. In *Drosophila*, ato is required for the development of a specific subset of sense organs, the chordotonal organs (Jarman et al., 1993). CHOs are internal mechanosensors of the PNS (McIver, 1985). Thus, ato and the CHOs provide an excellent system in which to ascertain not only the molecular and developmental relationship between invertebrate and vertebrate neurogenesis vis-à-vis the function of the proneural genes, but also the evolutionary conservation of sensory organ function and specification. Seven ato homologues have been cloned and analyzed in the mouse: Mouse Atonal Homologues (MATH) 1, 2, 3, 4A (also known as Ngn2), 4B (Ngn3), 4C (Ngn1), and 5 (Akazawa et al., 1995; Bartholoma and Nave, 1994; Ben-Arie et al., 1997, 1996; Fode et al., 1998; Ma et al., 1998; McCormick et al., 1996; Shimizu et al., 1995; Takebayashi et al., 1997). Most are expressed during neurogenesis in both the CNS and PNS. These homologues vary in the degree of their sequence conservation, and can be divided into three groups. The most distantly related group, the neurogenins, includes Ngn 1, 2 and 3. These gene products share, on average, 53% identity in the bHLH domain with ATO. They are expressed largely in mitotic CNS and sensory ganglia progenitor cells. Recent work suggests that these genes can play a role in neuroblast determination, and can therefore be true proneural genes (Fode et al., 1998; Ma et al., 1998). The second group includes MATH2 and MATH3, which share 57% identity in the bHLH domain with ATO. These proteins have been postulated to function in postmitotic neural cells (Bartholoma and Nave, 1994; Shimizu et al., 1995). Math2 expression is confined to the CNS, while Math3 is expressed in both the CNS and the trigeminal and dorsal root ganglia. The third group includes MATH1 and MATH5, arguably the only true ato homologues by amino acid sequence criteria, sharing 67% and 71% identity with the bHLH domain of ATO, respectively. It is noteworthy that both genes encode a basic domain identical to that of ATO. Interestingly, the basic domain of ATO was shown to be sufficient, in the context of another proneural protein (SCCUTE), to substitute for the loss of ato function (Chien et al., 1996). Math1 was initially shown to be expressed in the precursors of the cerebellar EGL and in the dorsal spinal cord (Ben-Arie et al., 1997, 1996). Math5 is expressed in the dividing progenitors in the developing retina and in the vagal ganglion (Brown et al., 1998). With the exception of Math5 expression in the neural retina, these observations pose a paradox: none of the vertebrate homologs appeared to be expressed in peripheral organs or tissues similar to those where ato is expressed. Jarman et al. (1993) reported that ato is expressed in the CNS. In the examples described herein it is shown that, in addition to the inner proliferation center of the optic lobe, ato is expressed in a small anteriomedial patch of cells in each brain lobe (FIG. 8F). Because it remains unclear, however, precisely what role ato plays in Drosophila CNS development, it has been difficult to argue that ato and its vertebrate homologues display functional conservation. Our experiments reveal sites of previously uncharacterized Math1 expression. As expected, we found that Math1/lacZ expression in the CNS corresponds to that of Math1, but we also found that Math1 is expressed in the skin, the joints, and the inner ear, in striking parallel to ato expression in the fly. Moreover, the expression in the ear (sensory epithelium) and the skin (Merkel cells) is restricted to sensory structures whose function is to convert mechanical stimuli into neuronal electrochemical signals. It is important to point out that in Drosophila, ato appears to play two roles simultaneously. It is required not only to select the precursors of the CHOs (proneural role), but also to specify these precursors as CHO precursors (lineage identity role) (Jarman and Ahmed, 1998; Jarman et al., 1993). The specificity of Math1 expression in the periphery makes it tempting to speculate that it, too, can endow specific cells with very specific lineage identities to distinguish them functionally from other sensory structures. The ability of Math1 to induce ectopic CHO formation and to restore CHOs to ato mutant embryos supports the notion that Math1, and particularly its basic domain, encodes lineage identity information not unlike that encoded by ato. This suggests that the mammalian cells expressing Math1, at least in the ear and the skin, are functionally similar and perhaps evolutionarily related to Drosophila cells that require ato. Furthermore, Math5 expression in the neural retina suggests that the functions of atonal in the fly are carried out by two genes in the mouse: the development of some mechanoreceptors is under the control of Math1 and retinal development is possibly under the control of Math5. It is interesting to note that in the fully sequenced nematode C. elegans, only one homolog of atonal, lin-32, was identified (Zhao and Emmons, 1995). Mutants with the u282 allele of lin-32 are touch-insensitive, which strengthens the argument for evolutionary conservation of atonal function in mechanoreception. The pattern of Math1/lacZ expression in the pontine nuclei suggested this region should be carefully evaluated in null mutants. Although no defects in the pons of Math1 null mice (Ben-Arie et al., 1997) were originally detected, closer analysis revealed the lack of pontine nuclei at this site. These neurons derive from the rhombic lip (Altman and Bayer, 1996) as do the EGL neurons, which are also lacking in Math1 null mice. While it is possible to draw parallels between Math1 and ato expression in the skin and ear, it is not clear that such is the case for the joints. ato expression in the fly joints is required for the formation of leg CHOs. In contrast, Math1 is expressed in resting and articular chondrocytes that do not have any described neural function, and for which no parallels exist in the fly. It can be that Math1 expression in cartilage indicates a novel role for a mechanosensory gene, or it can simply reflect similarities in the molecular events underlying the development of the various Math1-expressing cell types. Alternatively, CHOs can also function as joint structural elements in the fly, or articular cartilage can have a mechanoreceptive or transducive capacity yet to be described. There is no evidence at this point to support one or another of these possibilities. Analyzing the functions of ato and Math1 will enhance our understanding of neural development and the evolutionary conservation of sensory function. The sites and specificity of Math1 expression can make it suitable as a tool of gene therapy or gene activation approaches to illnesses such as hearing loss and osteoarthritis that are due to age-related or environmental damage.

EXAMPLE 14

Atonal-Associated Nucleic Acid Delivery Using Adenovirus

Human adenoviruses are double-stranded DNA tumor viruses with genome sizes of approximate 36 kb. As a model system for eukaryotic gene expression, adenoviruses have been widely studied and well characterized, which makes them an attractive system for development of adenovirus as a gene transfer system. This group of viruses is easy to grow and manipulate and they exhibit a broad host range in vitro and in vivo. In lytically infected cells, adenoviruses are capable of shutting off host protein synthesis, directing cellular machineries to synthesize large quantities of viral proteins, and producing copious amounts of virus.

The E1 region of the genome includes E1A and E1B, which encode proteins responsible for transcription regulation of the viral genome, as well as a few cellular genes. E2 expression, including E2A and E2B, allows synthesis of viral replicative functions, e.g. DNA-binding protein, DNA polymerase, and a terminal protein that primes replication. E3 gene products prevent cytolysis by cytotoxic T cells and tumor necrosis factor and appear to be important for viral propagation. Functions associated with the E4 proteins include DNA replication, late gene expression, and host cell shutoff. The late gene products include most of the virion capsid proteins, and these are expressed only after most of the processing of a single primary transcript from the major late promoter has occurred. The major late promoter (MLP) exhibits high efficiency during the late phase of the infection.

As only a small portion of the viral genome appears to be required in cis, adenovirus-derived vectors offer excellent potential for the substitution of large DNA fragments when used in connection with cell lines such as 293 cells. Ad5-transformed human embryonic kidney cell lines have been developed to provide the essential viral proteins in trans. The inventors thus reasoned that the characteristics of adenoviruses rendered them good candidates for use in targeting Math1 deficient cells in vivo. In another embodiment these constructs include a Hath1 or any atonal-associated nucleic acid sequence.

Particular advantages of an adenovirus system for delivering foreign proteins to a cell include: (i) the ability to substitute relatively large pieces of viral DNA by foreign DNA; (ii) the structural stability of recombinant adenoviruses; (iii) the safety of adenoviral administration to humans; (iv) lack of any known association of adenoviral infection with cancer or malignancies; (v) the ability to obtain high titers of the recombinant virus; and (vi) the high infectivity of Adenovirus.

One advantage of adenovirus vectors over retroviruses is a higher level of gene expression. Additionally, adenovirus replication is independent of host gene replication, unlike retroviral sequences. Because adenovirus transforming genes in the E1 region can be readily deleted and still provide efficient expression vectors, oncogenic risk from adenovirus vectors is thought to be negligible.

In general, adenovirus gene transfer systems are based upon recombinant, engineered adenovirus that is rendered replication-incompetent by deletion of a portion of its genome, such as E1, and yet still retains its competency for infection. Relatively large foreign proteins can be expressed when additional deletions are made in the adenovirus genome. For example, adenoviruses deleted in both E1 and E3 regions are capable of carrying up to 10 Kb of foreign DNA and can be grown to high titers in 293. Surprisingly, persistent expression of transgenes following adenoviral infection is possible. Use of the adenovirus gene transfer system can be more useful for the delivery of Math1 to cells in nascent or damaged cartilage in joints. In particular, the Math1 adenovirus can be used to deliver Math1, and confer Math1 gene expression in, non-ossified joint cartilage that has been damaged as a consequence of osteoarthritis.

EXAMPLE 15

Math1-Adenovirus Constructs

Recombinant virions for the controlled expression of Math1 can be constructed to exploit the advantages of adenoviral vectors, such as high titer, broad target range, efficient transduction, and non-integration in target cells for the transformation of cells into hair cells. In a specific embodiment these constructs include a Hath1 or any atonal-associated nucleic acid sequence. In one embodiment of the invention, a replication-defective, helper-independent adenovirus is created that expresses wild type Math1 sequences under the control of the human cytomegalovirus promoter or the metallothionine promoter.

Control functions on expression vectors are often provided from viruses when expression is desired in mammalian cells. For example, commonly used promoters are derived from polyoma, adenovirus 2 and simian virus 40 (SV40). The early and late promoters of SV40 virus are particularly useful because both are obtained easily from the virus as a fragment which also contains the SV40 viral origin of replication. Smaller or larger SV40 fragments can also be used provided there is included the approximately 250 bp sequence extending from the HindIII site toward the BglI site located in the viral origin of replication. Further, it is also possible, and often desirable, to use promoter or control sequences normally associated with the Math1 gene sequence, namely the Math1 promoter, provided such control sequences are compatible with the host cell systems or the target cell. One such target cell is located in the inner ear of a human patient in need of inner ear hair cells.

An origin of replication can be provided by construction of the vector to include an exogenous origin, such as can be derived from SV40 or other viral (e.g. polyoma, adeno, VSV, BPV) source, or can be provided by the host cell chromosomal replication mechanism. If the vector is integrated into the host cell chromosome, the latter is often sufficient.

EXAMPLE 16

Atonal-Associated Nucleic Acid Delivery Using Retrovirus

Another approach for gene delivery capitalizes on the natural ability of viruses to enter cells, bringing their own genetic material with them. Retroviruses have promise as gene delivery vectors due to their ability to integrate their genes into the host genome, transferring a large amount of foreign genetic material, infecting a broad spectrum of species and cell types and because they are easily packaged in special cell-lines. Retroviruses can be particularly useful for the delivery of Math1 into inner ear hair cells that have reduced expression of Math1, or that are in need of over-expression of Math1. In another embodiment these constructs include a Hath1 or any atonal-associated nucleic acid sequence.

EXAMPLE 17

Math1 Retroviral Constructs

The Math1 open reading frame (ORF) was excised from pBluescript by an EcoR I-XbaI digest. The fragment was gel purified, and blunt ended using Klenow DNA polymerase. The retroviral vector pLNCX (purchased from CLONTECH) was linearized with HpaI, and ligated with the Math1 ORF fragment. The ligation was transformed into transformation competent *E. coli* cells. The resulting antibiotic resistant colonies were assayed for the presence of the correct construct.

The cloning, reproduction and propagation retroviral expression vectors is well known to those of skill in the art. One example of a retroviral gene transfer and expression system that has been used to express Math1 is the CLONTECH pLNCX, pLXSN and LAPSN expression vectors. For propagation of these vectors PT67 and EcoPack packaging cell lines can be used. For more information on mammalian cell culture, the following general references can be used: *Culture of Animal Cells*, Third Edition, edition by R. I. Freshney (Wiley-Liss, 1993); and *Current Protocols in Molecular Biology*, ed. By F. M. Ausubel, et al., (Greene Publishing Associates and Wiley & Sons, 1994), relevant portions incorporated herein by reference.

In another embodiment constructs can be generated which include a Hath1 or any atonal-associated nucleic acid sequence.

EXAMPLE 18

Maintenance of Packaging Cell Lines

The maintenance of packaging cell lines, such as the 293 and PT67 packaging cell lines, is described briefly. A vial of frozen cells is transferred from liquid $N_2$ to a 37° C. water bath until just thawed. In order avoid osmotic shock to the cells, and to maximize cell survival, 1 ml of (Dulbecco's Modified Eagle Medium) DMEM is added to the tube and the mixture is transferred to a 15-ml tube. Another 5 ml of DMEM is added and the cells are mixed. After repeating these steps the final volume in the tube should be about 12 ml. Next, the cells are centrifuged at 500×g for 10 min. Finally, the supernatant is removed and the cells are resuspended in maintenance media as described in the next step. Generally, the cells are maintained in DMEM (high glucose: 4.5 g/L) containing 10% Fetal Bovine Serum (FBS), and 4 mM L-glutamine. If desired or necessary, 100 U/ml penicillin/100

μg/ml streptomycin can be added. It is recommended that are plated at 3-5×10$^5$ per 100-mm plate and split every 2 to 3 days, when they reach 70-80% confluency (confluence is 3-4×10$^6$ per 100-mm plate). The PT67 cell line, for example, has a very short doubling time (<16 h) and should be split before they become confluent. The doubling time for Eco-Pack-293 cells is 24-36 h.

Cells are split be removing the medium and washing the cells once with PBS. After treatment with 1-2 ml of trypsin-EDTA solution for 0.5-1 min, 5 to 10 ml of media and serum is added to stop trypsinization. The cells are dispersed gently, but thoroughly, by pipetting and are resuspended. Alternatively, a predetermined portion of the cells is replated in a 100-mm plate in 10 ml of medium, followed by rotation or shaking of the plate to distribute the cells evenly. A ratio of up to 1:20 for the PT67 or EcoPack-293 cells is common.

Generally, the percentage of PT67 or EcoPack-293 cells capable of packaging retroviral vectors decreases slowly with continued passage of the cell line. Therefore, packaging cells should be reselected after 2 months of growth in culture. Alternatively, new high-titer cells can be purchased from, e.g., CLONTECH, or low passage number stocks can be frozen, stored and thawed to increase the viral yield.

EXAMPLE 19

Methods Utilizing a Retroviral Vector

The following protocol is used to transfect the retroviral vector for virus production, infection of target cells, and selection of stable clones. Other methods and vectors can also be used with the present invention to express Math1, such as those described in *Retroviruses*, ed. by J. M. Coffin & H. E. Varmus (1996, Cold Spring Harbor Laboratory Press, NY) and *Current Protocols in Molecular Biology*, ed. by F. M. Ausubel et al. (1994, Greene Publishing Associates and Wiley & Sons), incorporated herein by reference. In another embodiment these constructs include a Hath1 or any atonal-associated nucleic acid sequence.

Briefly, the transfection of the retroviral vector into PT67 cells was as follows. Math1 was cloned into pLNX as described hereinabove. The packaging cells were plated to a density of 5-7×10$^5$ cells per 100-mm plate 12-24 hours before transfection. 1-2 hours before transfection, the medium replace with fresh medium. 25 μM chloroquine can be added just prior to transfection. Chloroquine increases transfection efficiency 2-3 fold. A 25 mM stock solution of chloroquine can be made in distilled water and filter sterilized.

To each 100-mm plate 10-15 μg of plasmid DNA using the desired method is transfected using, e.g., standard calcium-phosphate procedures (CalPhos Mammalian Transfection Kit, #K2050-1). The final volume of transfection mixture should not exceed 1 ml. The transfection solution is added to the medium and the plate is rotated to ensure even distribution. About 8 hours after transfection, a glycerol shock treatment can be performed to increase the uptake of DNA. After 10 to 24 hours post-transfection the medium was removed and the cells were washed twice with PBS, before adding 5 ml DMEM containing 10% FBS. The culture was incubated for an additional 12-48 hours to allow increase in virus titer. The virus titer reaches a maximum ~48 hours post-transfection and is generally at least 30% of maximum between 24 and 72 hours post-transfection.

Alternatively, a stable virus-producing cell lines can also be selected. To obtain stable virus-producing cell lines, the transfected packaging cells are plated in a selection medium 2-3 days post-transfection. For G418 selection of neomycin resistance, the cells are selected in the presence of G418 (0.5 mg/ml "active") for one week. Vectors carrying other selectable markers such as Puro, Bleo, or Hyg, can be used to obtain stable virus producing cell populations as well. Cell populations producing virions that produce titers of 10$^5$-10$^6$ recombinant virus particles per ml are common. Generally, 10$^5$-10$^6$ recombinant virus particles per ml is suitable for most purposes. For some studies, higher titer clones can be required. In this case, after antibiotic selection, individual clones are selected using, e.g., clone cylinders or limiting dilution, prior to propagation.

Viral titer can be determined in a variety or ways, one such method is described hereinbelow. The viral titer produced by transiently transfected or stable virus-producing packaging cell lines is determined as follows, NIH/3T3 cells are plated one day prior to beginning the titer procedure. Cells are plated in 6-well plates at a density of 5×10$^4$-1×10$^5$ cells per well and 4 ml of media are added per well. Virus-containing medium is collected from packaging cells, and polybrene is added to a final concentration of 4 μg/ml. The medium is filter-sterilized through a 0.45-μm filter. Polybrene is a polycation that reduces the charge repulsion between the virus and the cellular membrane. The filter should be cellulose acetate or polysulfonic (low protein binding) but not nitrocellulose. Nitrocellulose binds proteins in the retroviral membrane, and consequently destroys the virus. Serial dilutions are prepared as follows: six 10-fold serial dilutions are usually sufficient. To dilute the virus use fresh medium containing 4 μg/ml of polybrene. Next, NIH/3T3 target cells are infected by adding virus-containing medium to the wells. After 48 hours, the NIH/3T3 cells are stained. The titer of virus corresponds to the number of colonies present at the highest dilution that contains colonies, multiplied by the dilution factor. For example, the presence of four colonies in the 10$^5$ dilution would represent a viral titer of 4×10$^5$.

For the infection of cells, the following procedure was followed. The target cells were plated 12-18 hours before infection at a cell density of 3-5×10$^5$ per 100-mm plate. For the infection of cells that can be used for a biological assay, control cells can be treated with an insert-free virus produced under identical conditions. Half-maximal infection generally occurs after 5-6 hours of exposure of cells to virus, with maximal infection occurring after approximately 24 hours, of exposure. The actual reverse transcription and integration of the retrovirus takes place within 24-36 hours of infection, depending on cell growth kinetics. Expression can be observed at 24 hours, and reaches a maximum at approximately 48 hours. Alternatively, infections can be conducted sequentially, about 12 hours apart. Sequential infection generally increases the efficiency of infection and also increases viral copy number. A minimum of 12 hours between each infection is recommended in order to ensure that cellular receptors will be unoccupied by viral envelope.

EXAMPLE 20

Screening Assays

Finally, the present invention also provides candidate substance screening methods that are based upon whole cell assays, in vivo analysis and transformed or immortal cell lines in which a reporter gene is employed to confer on its recombinant hosts a readily detectable phenotype that emerges only under conditions where Math1 would be expressed, is under-expressed or is over-expressed. Generally, reporter genes encode a polypeptide not otherwise produced by the host cell that is detectable by analysis, e.g., by chromogenic, fluorometric, radioisotopic or spectrophotometric analysis. In the present invention the Math1 gene has been replaced with β-galactosidase in a mouse.

An example of a screening assay of the present invention is presented herein. Math1 expressing cells are grown in microtiter wells, followed by addition of serial molar proportions of the small molecule candidate to a series of wells, and determination of the signal level after an incubation period that is sufficient to demonstrate, e.g., calretinin expression in controls incubated solely with the vehicle used to resuspend or dissolve the compound. The wells containing varying proportions of candidate are then evaluated for signal activation. Candidates that demonstrate dose related enhancement of reporter gene transcription or expression are then selected for further evaluation as clinical therapeutic agents. The stimulation of transcription can be observed in the absence of expressed Math1, in which case the candidate compound might be a positive stimulator of hair cell differentiation. Alternatively, the candidate compound might only give a stimulation in the presence of low levels of Math1, which would suggest that it functions to stabilize the formation of Math1 dimers or the interaction of Math1 with one or more transcriptional factors. Candidate compounds of either class might be useful therapeutic agents that would stimulate production of inner ear hair cells and thereby address the need of patients with hearing loss or balance control impairments.

EXAMPLE 21

Transfection of Cells with Math1 Retroviral Vectors

The present invention provides recombinant host cells transformed or transfected with a polynucleotide that encodes Math1, as well as transgenic cells derived from those transformed or transfected cells. In another embodiment these constructs include a Hath1 or any atonal-associated nucleic acid sequence. Preferably, a recombinant host cell of the present invention is transfected with a polynucleotide containing a functional Math1 nucleic acid sequence or a chimeric Math1 gene. Methods of transforming or transfecting cells with exogenous polynucleotides, such as DNA molecules, are well known in the art and include techniques such as calcium-phosphate- or DEAE-dextran-mediated transfection, protoplast fusion, electroporation, liposome mediated transfection, direct microinjection and adenovirus infection.

Math1 expression using recombinant constructs can be used to target the delivery of Math1 to cells in need thereof. Different promoter-vector combinations can be chosen by a person skilled in these arts to drive Math1 expression in different cell types. In some cases, the desired outcome can not be protein, but RNA, and recombinant vectors would include those with inserts present in either forward or reverse orientations. In addition, some vectors, for instance retroviruses or artificial recombination systems, can be designed to incorporate sequences within a cellular or viral genome in order to achieve constitutive or inducible expression of protein or RNA.

Many of the vectors and hosts are available commercially and have specific features that facilitate expression or subsequent purification. For instance DNA sequences to be expressed as proteins often appear as fusion with unrelated sequences that encode polyhistidine tags, or HA, FLAG, myc and other epitope tags for immunochemical purification and detection, or phosphorylation sites, or protease recognition sites, or additional protein domains such as glutathione S-transferase (GST), maltose binding protein (MBP) (New England Biolabs), and so forth that facilitate purification.

Vectors can also be designed that contain elements for polyadenylation, splicing, and termination, such that incorporation of naturally occurring genomic DNA sequences that contain introns and exons can be produced and processed, or such that unrelated introns and other regulatory signals require RNA processing prior to production of mature, translatable RNAs. Proteins produced in the systems described above are subject to a variety of post-translational modifications, such as glycosylation, phosphorylation, nonspecific or specific proteolysis or processing.

EXAMPLE 22

Delivery of Math1 as an Amino Acid Sequence

A peptide (11 amino acids) derived from HIV has been recently described that when fused to full length proteins and injected into mice allow a rapid dispersal to the nucleus of all cells of the body (Schwarze et al., 1999). Schwarze et al. made fusion proteins to Tat ranging in size from 15 to 120 kDa. They documented a rapid uptake of the fusion proteins to the nuclei of cells throughout the animal, and the functional activity of said proteins was retained.

In an embodiment of the present invention there are constructs containing the Tat or Tat-HA nucleic acid sequence operatively linked to a Math1 nucleic acid sequence. In another embodiment these constructs include a Hath1 or any atonal-associated nucleic acid sequence. The vectors are expressed in bacterial cultures and the fusion protein is purified. This purified Tat-Math1 protein or Tat-Hath1 protein is injected into animal to determine the efficiency of the Tat delivery system into the inner ear, skin, cerebellum, brain stem, spinal cord and joints. Analysis is carried out to determine the potential of the Tat-Math1/Tat-Hath1 protein in hair cell and neuronal regeneration. This is a viable therapeutic approach either in its own right or in association with other methods or genes.

It should be understood that the methods to screen for compounds which affect Math1 expression disclosed herein are useful notwithstanding that effective candidates can not be found, since it is of practical utility to know what upstream effector is necessary for Math1 transcription.

REFERENCES

All patents and publications are herein incorporated by reference to the same extent as if each individual publication was specifically and individually indicated to be incorporated by reference.

PUBLICATIONS

Akazawa, C., Ishibashi, M., Shimizu, C., Nakanishi, S., and Kageyama, R. (1995). A mammalian helix-loop-helix factor structurally related to the product of Drosophila proneural gene atonal is a positive transcriptional regulator expressed in the developing nervous system. J Biol Chem 270, 8730-8.

Alder, J., Cho, N., and Hatten, M. (1996). Embryonic precursor cells from the rhombic lip are specified to a cerebellar granule neuron identity. Neuron 17, 389-399.

Altman, J., and Bayer, S. A. (1996). Development of the Cerebellar System: In Relation to its Evolution, Sturcture, and Functions. Boca Raton, Fla.: CRC Press.

Anderson, D. J. (1995). Neural development. Spinning skin into neurons. Curr Biol 5, 1235-8.

Bartholomä, A., and Nave, K. A. (1994). NEX-1: a novel brain-specific helix-loop-helix protein with autoregulation and sustained expression in mature cortical neurons. Mech Dev 48, 217-28.

Ben-Arie, N., Hassan, B. A., Birmingham, N. A., Malicki, D. M., Armstrong, D., Matzuk, M., Bellen, H. J., and Zoghbi, H. Y. (2000). Functional conservation of atonal and Math1 in the CNS and PNS. Development 127: 1039-1048.

Ben-Arie, N., Bellen, H. J., Armstrong, D. L., McCall, A. E., Gordadze, P. R., Guo, Q., Matzuk, M. M., and Zoghbi, H. Y. (1997). Math1 is essential for genesis of cerebellar granule neurons. Nature 390, 169-172.

Ben-Arie, N., McCall, A. E., Berkman, S., Eichele, G., Bellen, H. J., and Zoghbi, H. Y. (1996). Evolutionary conservation of sequence and expression of the bHLH protein Atonal suggests a conserved role in neurogenesis. Human Molecular Genetics 5, 1207-1216.

Bermingham, N. A., Hassan, B. A., Price, S. D., Vollrath, M. A., Ben-Arie, N., Eatock, R. A., Bellen, H. J., Lysakowski, A., and Zoghbi, H. Y. (1999). Math1: An essential gene for the generation of inner ear hair cells. Science 284, 1837-41.

Bi, W., Deng, J. M., Zhang, Z., Behringer, R. R., and de Crombrugghe, B. (1999). Sox9 is required for cartilage formation. Nat Genet 22, 85-9.

Bonnerot, C., and Nicolas, J. F. (1993). Application of LacZ gene fusions to postimplantation development. Methods Enzymol 225, 451-69.

Boyan, G. S. (1993). Another look at insect audition: the tympanic receptors as an evolutionary specialization of the chordotonal system. J Insect Physiol 39, 187-200.

Brand, A. H., and Perrimon, N. (1993). Targeted gene expression as a means of altering cell fates and generating dominant phenotypes. Development 118, 401-15.

Brown, N. L., Kanekar, S., Vetter, M. L., Tucker, P. K., Gemza, D. L., and Glaser, T. (1998). Math5 encodes a murine basic helix-loop-helix transcription factor expressed during early stages of retinal neurogenesis. Development 125, 4821-4833.

Buckwalter, J. A., and Mankin, H. J. (1998). Articular cartilage: tissue design and chondrocyte-matrix interactions. Instr Course Lect 47, 477-86.

Chien, C. T., Hsiao, C. D., Jan, L. Y., and Jan, Y. N. (1996). Neuronal type information encoded in the basic-helix-loop-helix domain of proneural genes. Proc Natl Acad Sci U S A 93, 13239-44.

Davis, R. L., Cheng, P. F., Lassar, A. B., and Weintraub, H. (1990). The MyoD DNA binding domain contains a recognition code for muscle-specific gene activation. Cell 60, 733-46.

Dreller, C., and Kirschner, W. H. (1993). Hearing in honeybees: localization of the audiotory sense organ. J. Comp Physio A 173, 275-279.

Eberl, D. F. (1999). Feeling the vibes: chordotonal mechanisms in insect hearing. Curr Opin Neurobiol 9, 389-393.

Ferguson, B. M., Brockdorff, N., Formstone, E., Ngyuen, T., Kronmiller, J. E., and Zonana, J. (1997). Cloning of Tabby, the murine homolog of the human EDA gene: evidence for a membrane-associated protein with a short collagenous domain. Hum Mol Genet 6, 1589-94.

Fode, C., Gradwohl, G., Morin, X., Dierich, A., LeMeur, M., Goridis, C., and Guillemot, F. (1998). The bHLH protein NEUROGENIN 2 is a determination factor for epibranchial placode-derived sensory neurons. Neuron 20, 483-94.

Friedrich, G., and Soriano, P. (1991). Promoter traps in embryonic stem cells: a genetic screen to identify and mutate developmental genes in mice. Genes Dev 5, 1513-23.

Ghysen, A., and Dambly-Chaudiere, C. (1989). Genesis of the Drosophila peripheral nervous system. Trends Genet 5, 251-5.

Graneberg, H. (1971). The tabby syndrome in the mouse. Proc R Soc Lond B Biol Sci 179, 139-156.

Guillemot, F. (1995). Analysis of the role of basic-helix-loop-helix transcription factors in the development of neural lineages in the mouse. Biol Cell 84, 227-241.

Hatten, M. E., and Heintz, N. (1995). Mechanisms of neural patterning and specification in the developing cerebellum. Ann Rev Neurosci 18, 385-408.

Helms, A. W., and Johnson, J. E. (1998). Progenitors of dorsal commissural inteneurons are defined by MATH1 expression. Development 125, 919-28.

Horton, W. A., Machado, M. A., Ellard, J., Campbell, D., Putnam, E. A., Aulthouse, A. L., Sun, X., and Sandell, L. J. (1993). An experimental model of human chondrocyte differentiation. Prog Clin Biol Res 383B, 533-40.

Jarman, A. P., and Ahmed, I. (1998). The specificity of proneural genes in determining Drosophila sense organ identity. Mech Dev 76, 117-25.

Jarman, A. P., Grau, Y., Jan, L. Y., and Jan, Y. N. (1993). atonal is a proneural gene that directs chordotonal organ formation in the Drosophila peripheral nervous system. Cell 73, 1307-21.

Kania, A., Salzberg, A., Bhat, M., D'Evelyn, D., He, Y., Kiss, I., and Bellen, H. J. (1995). P-element mutations affecting embryonic peripheral nervous system development in Drosophila melanogaster. Genetics 139, 1663-1678.

Karsenty, G. (1998). Genetics of skeletogenesis. Dev Genet 22, 301-13.

Lee, J. E. (1997). Basic helix-loop-rhelix genes in neural development. Curr. Opin. Neurobiol 7, 13-20.

Lee, K. J., Mendelsohn, M., and Jessell, T. M. (1998). Neuronal patterning by BMPs: a requirement for GDF7 in the generation of a discrete class of commissural inteneurons in the mouse spinal cord. Genes Dev 12, 3394-407.

Liu, X. Y., Dangel, A. W., Kelley, R. I., Zhao, W., Denny, P., Botcherby, M., Cattanach, B., Peters, J., Hunsicker, P. R., Mallon, A. M., Strivens, M. A., Bate, R., Miller, W., Rhodes, M., Brown, S. D., and Herman, G. E. (1999). The gene mutated in bare patches and striated mice encodes a novel 3beta-hydroxysteroid dehydrogenase. Nat Genet 22, 182-7.

Ma, Q., Chen, Z., del Barco Barrantes, I., de la Pompa, J. L., and Anderson, D. J. (1998). neurogenin1 is essential for the determination of neuronal precursors for proximal cranial sensory ganglia. Neuron 20, 469-82.

McCormick, M. B., Tamimi, R. M., Snider, L., Asakura, A., Bergstrom, D., and Tapscott, S. J. (1996). NeuroD2 and neuroD3: distinct expression patterns and transcriptional activation potentials within the neuroD gene family. Mol Cell Biol 16, 5792-800.

McIver, S. B. (1985). Mechanoreception. In Comprehensive Insect Physiology, Biochemistry, and Pharmacology (G. A. Kerkut and L. I. Gilbert, Eds.), pp. 71-132. Oxford: Pergamon Press.

Moulins, M. (1976). Ultrastructure of chordotonal organs. In Structure and Function of Proprioceptors in the Invertebrates (P. J. Mill, Ed.), pp. 387-426. London: Chapman and Hall.

Munger, B. L. (1991). The Biology of Merkel Cells. In Physiology, Biochemistry, and Molecular Biology of the Skin, second edition (L. A. Goldsmith, Ed.), pp. 836-856. Oxford, UK: Oxford University Press.

Pinkus, F. (1905). Über Hautsinnesorgane neben dem menschlichen Haar (Haarscheiben) und ihre verglei chend-anatomische Bedeutung. Arch mikr Anat 65, 121-179.

Poole, C. A. (1997). Articular cartilage chondrons: form, function and failure. J Anat 191, 1-13.

Rodriguez, I., Hernandez, R., Modolell, J., and Ruiz-Gomez, M. (1990). Competence to develop sensory organs is temporally and spatially regulated in *Drosophila* epidermal primordia. Embo J 9, 3583-92.

Sambrook, Fritsch, Maniatis, In: Molecular Cloning: A Laboratory Manual, Vol. 1, Cold Spring Harbor Laboratory Press, Cold Spring Harbor, N.Y., Ch. 7,7.19-17.29, 1989.

Schwarze, S. R., Ho, A., Vocero-Akbani, A. and Dowdy, S. F. (1999). In vivo protein transduction: delivery of a biologically active protein in the mouse. Science 285, 1569-72.

Shimizu, C., Akazawa, C., Nakanishi, S., and Kageyama, R. (1995). MATH-2, a mammalian helix-loop-helix factor structurally related to the product of *Drosophila* proneural gene atonal, is specifically expressed in the nervous system. Eur J Biochem 229, 23948.

Sun, Y., Jan, L. Y., and Jan, Y. N. (1998). Transcriptional regulation of atonal during development of the *Drosophila* peripheral nervous system. Development 125, 3731-40.

Takebayashi, K., Takahashi, S., Yokota, C., Tsuda, H., Nakanishi, S., Asashima, M., and Kageyama, R. (1997). Conversion of ectoderm into a neural fate by ATH-3, a vertebrate basic helix-loop-helix gene homologous to *Drosophila* proneural gene atonal. Embo J 16, 384-95.

Tautz, D., and Pfeifle, C. (1989). A nonradioactive in situ hybridization method for the localization of specific RNAs in *Drosophila* embryos reveals translation control of the segmentation gene hunchback. Chromosoma 98, 81-85.

Vaessin, H., Caudy, M., Bier, E., Jan; L. Y., and Jan, Y. N. (1990). Role of helix-loop-helix proteins in *Drosophila* neurogenesis. Cold Spring Harb Symp Quant Biol 55, 23945.

van Staaden, M. J., and Römer, H. (1998). Evolutionary transition from stretch to hearing organs in ancient grasshoppers. Nature 384, 773-776.

Vielkind, U., Sebzda, M. K., Gibson, I. R., and Hardy, M. H. (1995). Dynamics of Merkel cell patterns in developing hair follicles in the dorsal skin of mice, demonstrated by a monoclonal antibody to mouse keratin 18. Acta Anat 152, 93-109.

Yamakado, M., and Yohro, T. (1979). Subdivision of mouse vibrissae on an embryological basis, with descriptions of variations in the number and arrangement of sinus hairs and cortical barrels in BALB/c (nu/+; nude, nu/nu) and hairless (hr/hr) strains. Am J Anat 155, 153-173.

Zhao, C., and Emmons, S. W. (1995). A transcription factor controlling development of peripheral sense organs in *C. elegans*. Nature 373, 74-78.

Patents

U.S. Pat. No. 5,840,873, issued Nov. 24, 1998
U.S. Pat. No. 5,843,640, issued Dec. 1, 1998
U.S. Pat. No. 5,843,650, issued Dec. 1. 1998
U.S. Pat. No. 5,843,651, issued Dec. 1, 1998
U.S. Pat. No. 5,843,663, issued Dec. 1, 1998
U.S. Pat. No. 5,846,708, issued Dec. 8, 1998
U.S. Pat. No. 5,846,709, issued Dec. 8, 1998
U.S. Pat. No. 5,846,717, issued Dec. 8, 1998
U.S. Pat. No. 5,846,726, issued Dec. 8, 1998
U.S. Pat. No. 5,846,729, issued Dec. 8, 1998
U.S. Pat. No. 5,846,783, issued Dec. 8, 1998
U.S. Pat. No. 5,849,481, issued Dec. 15, 1998
U.S. Pat. No. 5,849,483, issued Dec. 15, 1998
U.S. Pat. No. 5,849,486, issued Dec. 15, 1998
U.S. Pat. No. 5,849,487, issued Dec. 15, 1998
U.S. Pat. No. 5,849,497, issued Dec. 15, 1998
U.S. Pat. No. 5,849,546, issued Dec. 15, 1998
U.S. Pat. No. 5,849,547, issued Dec. 15, 1998
U.S. Pat. No. 5,851,770, issued Dec. 22, 1998
U.S. Pat. No. 5,851,772, issued Dec. 22, 1988
U.S. Pat. No. 5,853,990, issued Dec. 29, 1998
U.S. Pat. No. 5,853,993, issued Dec. 29, 1998
U.S. Pat. No. 5,853,992, issued Dec. 29, 1998
U.S. Pat. No. 5,856,092, issued Jan. 5, 1999
U.S. Pat. No. 5,858,652, issued Jan. 12, 1999
U.S. Pat. No. 5,861,244, issued Jan. 19, 1999
U.S. Pat. No. 5,863,732, issued Jan. 26, 1999
U.S. Pat. No. 5,863,753, issued Jan. 26, 1999
U.S. Pat. No. 5,866,331, issued Feb. 2, 1999
U.S. Pat. No. 5,866,336, issued Feb. 2, 1999
U.S. Pat. No. 5,866,337, issued Feb. 2, 1999
U.S. Pat. No. 5,900,481, issued May 4, 1999
U.S. Pat. No. 5,905,024, issued May 18, 1999
U.S. Pat. No. 5,910,407, issued Jun. 8, 1999
U.S. Pat. No. 5,912,124, issued Jun. 15, 1999
U.S. Pat. No. 5,912,145, issued Jun. 15, 1999
U.S. Pat. No. 5,912,148, issued Jun. 15, 1999
U.S. Pat. No. 5,916,776, issued Jun. 29, 1999
U.S. Pat. No. 5,916,779, issued Jun. 29, 1999
U.S. Pat. No. 5,919,626, issued Jul. 6, 1999
U.S. Pat. No. 5,919,630, issued Jul. 6, 1999
U.S. Pat. No. 5,922,574, issued Jul. 13, 1999
U.S. Pat. No. 5,925,517, issued Jul. 20, 1999
U.S. Pat. No. 5,925,525, issued Jul. 20, 1999
U.S. Pat. No. 5,928,862, issued Jul. 27, 1999
U.S. Pat. No. 5,928,869, issued Jul. 27, 1999
U.S. Pat. No. 5,928,870, issued Jul. 27, 1999
U.S. Pat. No. 5,928,905, issued Jul. 27, 1999
U.S. Pat. No. 5,928,906, issued Jul. 27, 1999
U.S. Pat. No. 5,929,227, issued Jul. 27, 1999
U.S. Pat. No. 5,932,413, issued Aug. 3, 1999
U.S. Pat. No. 5,932,451, issued Aug. 3, 1999
U.S. Pat. No. 5,935,791, issued Aug. 10, 1999
U.S. Pat. No. 5,935,825, issued Aug. 10, 1999
U.S. Pat. No. 5,939,291, issued Aug. 17, 1999
U.S. Pat. No. 5,942,391, issued Aug. 24, 1999
European Application No. 320 308
European Application No. 329 822
GB Application No. 2 202 328
PCT Application No. PCT/US87/00880
PCT Application No. PCT/US89/01025
PCT Application WO 88/10315
PCT Application WO 89/06700
PCT Application WO 90/07641

One skilled in the art readily appreciates that the present invention is well adapted to carry out the objectives and obtain the ends and advantages mentioned as well as those inherent therein. Sequences, mutations, complexes, methods, treatments, pharmaceutical compositions, procedures and techniques described herein are presently representative of the preferred embodiments and are intended to be exemplary and are not intended as limitations of the scope. Changes therein and other uses will occur to those skilled in the art which are encompassed within the spirit of the invention or defined by the scope of the pending claims.

What is claimed is:

1. A method of treating animal for imbalance disorder, comprising delivering directly to a cell in an inner ear of said animal a therapeutically effective amount of an atonal-associated amino acid molecule or nucleic acid molecule, wherein said amino acid molecule has hair cell generating activity and the sequence of said amino acid molecule has at least about 80% identity to SEQ ID NO:58 (Hath1) and comprises at least about 80% identity to SEQ ID NO:70, and wherein said nucleic acid molecule encodes said amino acid molecule, and wherein upon said delivery step the imbalance disorder is treated.

2. The method of claim 1 wherein said delivery comprises injecting into an inner ear a therapeutically effective amount of an atonal-associated amino acid molecule or nucleic acid molecule.

3. The method of claim 1, wherein said atonal-associated amino acid molecule or nucleic acid molecule is Math 1.

4. The method of claim 1, wherein said atonal-associated amino acid molecule or nucleic acid molecule is Hath1.

5. The method of claim 1, wherein said amino acid molecule is administered by a delivery vehicle.

6. The method of claim 5, wherein said delivery vehicle for said nucleic acid molecule is selected from the group consisting of an adenoviral vector, a retroviral vector, and adeno-associated viral vector, a plasmid, a liposome.

7. The method of claim 5, wherein said delivery vehicle for said nucleic acid molecule is selected from the group consisting of a viral vector or a non-viral vector.

8. The method of claim 1, wherein said cell contains an alteration in an atonal-associated nucleic acid molecule or amino acid molecule.

* * * * *

SEQUENCE LISTING

<160> NUMBER OF SEQ ID NOS: 70

<210> SEQ ID NO 1
<211> LENGTH: 1065
<212> TYPE: DNA
<213> ORGANISM: Human

<400> SEQUENCE: 1

```
atgtcccgcc tgctgcatgc agaagagtgg gctgaagtga aggagttggg agaccaccat      60
cgccagcccc agccgcatca tctcccgcaa ccgccgccgc cgccgcagcc acctgcaact     120
ttgcaggcga gagagcatcc cgtctacccg cctgagctgt ccctcctgga cagcaccgac     180
ccacgcgcct ggctggctcc cactttgcag ggcatctgca cggcacgcgc cgcccagtat     240
tgctacatt  ccccggagct gggtgcctca gaggccgctg cgccccggga cgaggtggac     300
ggccggggg  agctggtaag gaggagcagc ggcggtgcca gcagcagcaa gagccccggg     360
ccggtgaaag tgcgggaaca gctgtgcaag ctgaaaggcg gggtggtggt agacgagctg     420
ggctgcagcc gccaacgggc cccttccagc aaacaggtga atggggtgca gaagcagaga     480
cggctagcag ccaacgccag ggagcggcgc aggatgcatg gctgaaccga gccttcgac      540
cagctgcgca atgttatccc gtcgttcaac aacgacaaga agctgtccaa atatgagacc     600
ctgcagatgg cccaaatcta catcaacgcc ttgtccgagc tgctacaaac gcccagcgga     660
ggggaacagc caccgccgcc tccagcctcc tgcaaaagcg accaccacca ccttcgcacc     720
gcggcctcct atgaaggggg cgcgggcaac gcgaccgcag ctggggctca gcaggcttcc     780
ggagggagcc agcggccgac cccgcccggg agttgccgga ctcgcttctc agccccagct     840
tctgcgggag ggtactcggt gcagctggac gctctgcact tctcgacttt cgaggacagc     900
gccctgacag cgatgatggc gcaaaagaat ttgtctcctt ctctccccgg gagcatcttg     960
cagccagtgc aggaggaaaa cagcaaaact tcgcctcggt cccacagaag cgacggggaa    1020
ttttcccccc attcccatta cagtgactcg gatgaggcaa gttag                    1065
```

<210> SEQ ID NO 2
<211> LENGTH: 354
<212> TYPE: PRT
<213> ORGANISM: Human

<400> SEQUENCE: 2

Met Ser Arg Leu Leu His Ala Glu Glu Trp Ala Glu Val Lys Glu Leu
1               5                   10                  15

Gly Asp His His Arg Gln Pro Gln Pro His His Leu Pro Gln Pro Pro
                20                  25                  30

Pro Pro Pro Gln Pro Pro Ala Thr Leu Gln Ala Arg Glu His Pro Val
            35                  40                  45

Tyr Pro Pro Glu Leu Ser Leu Leu Asp Ser Thr Asp Pro Arg Ala Trp
        50                  55                  60

Leu Ala Pro Thr Leu Gln Gly Ile Cys Thr Ala Arg Ala Ala Gln Tyr
65                  70                  75                  80

Leu Leu His Ser Pro Glu Leu Gly Ala Ser Glu Ala Ala Ala Pro Arg
                85                  90                  95

Asp Glu Val Asp Gly Arg Gly Glu Leu Val Arg Arg Ser Ser Gly Gly
                100                 105                 110

Ala Ser Ser Ser Lys Ser Pro Gly Pro Val Lys Val Arg Glu Gln Leu
            115                 120                 125

```
Cys Lys Leu Lys Gly Gly Val Val Asp Glu Leu Gly Cys Ser Arg
    130                 135                 140
Gln Arg Ala Pro Ser Ser Lys Gln Val Asn Gly Val Gln Lys Gln Arg
145                 150                 155                 160
Arg Leu Ala Ala Asn Ala Arg Glu Arg Arg Arg Met His Gly Leu Asn
                165                 170                 175
His Ala Phe Asp Gln Leu Arg Asn Val Ile Pro Ser Phe Asn Asn Asp
            180                 185                 190
Lys Lys Leu Ser Lys Tyr Glu Thr Leu Gln Met Ala Gln Ile Tyr Ile
        195                 200                 205
Asn Ala Leu Ser Glu Leu Leu Gln Thr Pro Ser Gly Gly Glu Gln Pro
    210                 215                 220
Pro Pro Pro Ala Ser Cys Lys Ser Asp His His Leu Arg Thr
225                 230                 235                 240
Ala Ala Ser Tyr Glu Gly Gly Ala Gly Asn Ala Thr Ala Ala Gly Ala
                245                 250                 255
Gln Gln Ala Ser Gly Gly Ser Gln Arg Pro Thr Pro Pro Gly Ser Cys
            260                 265                 270
Arg Thr Arg Phe Ser Ala Pro Ala Ser Ala Gly Gly Tyr Ser Val Gln
        275                 280                 285
Leu Asp Ala Leu His Phe Ser Thr Phe Glu Asp Ser Ala Leu Thr Ala
    290                 295                 300
Met Met Ala Gln Lys Asn Leu Ser Pro Ser Leu Pro Gly Ser Ile Leu
305                 310                 315                 320
Gln Pro Val Gln Glu Glu Asn Ser Lys Thr Ser Pro Arg Ser His Arg
                325                 330                 335
Ser Asp Gly Glu Phe Ser Pro His Ser His Tyr Ser Asp Ser Asp Glu
            340                 345                 350
Ala Ser

<210> SEQ ID NO 3
<211> LENGTH: 420
<212> TYPE: DNA
<213> ORGANISM: MOUSE

<400> SEQUENCE: 3
tcgtcccacg cgtccgcgcc aagcccgcgg cgcggaggac accgtgctcg gttccgggct     60
gcggggacat tcccggacac acaccggagc agcagctgcg ccgcgacaca tctggagccg    120
cgtaggatgt tcgtcaaatc tgagactctg gagttgaagg aggaagagga ggtactgatg    180
ctgctgggct cggcttcccc ggcctcggcg accctgaccc cgatgtcctc cagcgcggac    240
gaggaggagg acgaggagct cgccggccg ggctccgcgc gtgggcagcg tggagcggaa    300
gccgggcagg gggtgcaggg cagtccggcg tcgggtgcct ggggttgccg gacagggcgg    360
ctgctatgca ctgtgcacga gtgctagcgt gtgccgtcgc gctcacgggc cgtctgcaga    420

<210> SEQ ID NO 4
<211> LENGTH: 645
<212> TYPE: DNA
<213> ORGANISM: MOUSE

<400> SEQUENCE: 4
atggcgcctc atcccttgga tgcgctcacc atccaagtgt ccccagagac acaacaacct     60
tttcccggag cctcggacca cgaagtgctc agttccaatt ccaccccacc tagccccact    120
```

-continued

```
ctcatatccta gggactgctc cgaagcagaa gtgggtgact gccgagggac ctcgaggaag     180
ctccgcgccc gacgcggagg gcgcaacagg cccaagagcg agttggcact cagcaaacag     240
cgaagaagcc ggcgcaagaa ggccaatgat cgggagcgca atcgcatgca aacctcaac      300 tcggcgctgg atgcgctgcg cggtgtcctg cccaccttcc cggatgacgc caaacttaca     360
aagatcgaga ccctgcgctt cgcccacaac tacatctggg cactgactca gacgctgcgc     420
atagcggacc acagcttcta tggcccggag cccctgtgc cctgtggaga gctggggagc      480
cccggaggtg gctccaacgg ggactggggc tctatctact ccccagtctc ccaagcgggt    540
aacctgagcc ccacggcctc attggaggaa ttccctggcc tgcaggtgcc cagctcccca    600
tcctatctgc tcccgggagc actggtgttc tcagacttct tgtga                    645
```

<210> SEQ ID NO 5
<211> LENGTH: 214
<212> TYPE: PRT
<213> ORGANISM: MOUSE

<400> SEQUENCE: 5

```
Met Ala Pro His Pro Leu Asp Ala Leu Thr Ile Gln Val Ser Pro Glu
 1               5                  10                  15

Thr Gln Gln Pro Phe Pro Gly Ala Ser Asp His Glu Val Leu Ser Ser
            20                  25                  30

Asn Ser Thr Pro Pro Ser Pro Thr Leu Ile Pro Arg Asp Cys Ser Glu
        35                  40                  45

Ala Glu Val Gly Asp Cys Arg Gly Thr Ser Arg Lys Leu Arg Ala Arg
    50                  55                  60

Arg Gly Gly Arg Asn Arg Pro Lys Ser Glu Leu Ala Leu Ser Lys Gln
65                  70                  75                  80

Arg Arg Ser Arg Arg Lys Lys Ala Asn Asp Arg Glu Arg Asn Arg Met
                85                  90                  95

His Asn Leu Asn Ser Ala Leu Asp Ala Leu Arg Gly Val Leu Pro Thr
            100                 105                 110

Phe Pro Asp Asp Ala Lys Leu Thr Lys Ile Glu Thr Leu Arg Phe Ala
        115                 120                 125

His Asn Tyr Ile Trp Ala Leu Thr Gln Thr Leu Arg Ile Ala Asp His
    130                 135                 140

Ser Phe Tyr Gly Pro Glu Pro Val Pro Cys Gly Glu Leu Gly Ser
145                 150                 155                 160

Pro Gly Gly Gly Ser Asn Gly Asp Trp Gly Ser Ile Tyr Ser Pro Val
                165                 170                 175

Ser Gln Ala Gly Asn Leu Ser Pro Thr Ala Ser Leu Glu Glu Phe Pro
            180                 185                 190

Gly Leu Gln Val Pro Ser Ser Pro Ser Tyr Leu Leu Pro Gly Ala Leu
        195                 200                 205

Val Phe Ser Asp Phe Leu
    210
```

<210> SEQ ID NO 6
<211> LENGTH: 1412
<212> TYPE: DNA
<213> ORGANISM: MOUSE

<400> SEQUENCE: 6

```
cgtgctcggt tccgggctgc ggggacattc ccggacacac accggagcag cagctgcgcc    60
gcgacacatc tggagccgcg taggatgttc gtcaaatctg agactctgga gttgaaggag   120
```

```
gaagaggagg tactgatgct gctgggctcg gcttccccgg cctcggcgac cctgacccccg    180
atgtcctcca gcgcggacga ggaggaggac gaggagctgc gccggccggg ctccgcgcgt    240
gggcagcgtg gagcggaagc cgggcagggg gtgcagggca gtccggcgtc gggtgccggg    300
ggttgccggc cagggcggct gctgggcctg atgcacgagt gcaagcgtcg cccgtcgcgc    360
tcacgggccg tctcccgagg tgccaagacg cggagacgg tgcagcgcat caagaagacc     420
cgcaggctca aggccaacaa ccgcgagcgc aaccgcatgc acaacctaaa cgccgcgctg    480
gacgcgctgc gcgaggtgct gcccaccttc cccgaggatg ccaagctcac gaagatcgag    540
acgctgcgct tcgcccacaa ttacatctgg gcgctcaccg agactctgcg cctggcggac    600
cactgcgccg gcgccggtgg cctccagggg gcgctcttca cggaggcggt gctcctgagc    660
ccgggagctg cgctcggcgc cagcggggac agcccttctc caccttcctc ctggagctgc    720
accaacagcc cggcgtcatc ctccaactcc acgtccccat acagctgcac tttatcgccc    780
gctagccccg ggtcagacgt ggactactgg cagcccccac ctccggagaa gcatcgttat    840
gcgcctcacc tgcccctcgc cagggactgt atctagagct gcgggtctcc ctctctcgtc    900
ctctacccgg ccctcttccc atccttctcc cgcccctcac cctccacgcc ccggactcca    960
cttcacagag cagaggtggc ccttgcaatc ccctcggcgg ctggtgcatt cggggggtgga   1020
gaccagctct ggtttattga agatgtgagg atttatggtc aaagaggact atggcgtgtg    1080
ggagtgggg ctggcgtggg gaacctcgta agactgtaaa agacactgag aaaaagtacc     1140
ataactaacg agtgtgcaga gcagactgac gctcctcccc tctctcagag ctgctggagg    1200
agaactccgg gcaggcagtt cgtgtgaatc tctcagaggg aatgcaactg gtccctgtga    1260
tcttttcacc ttcgtttcta catagagatg ttaatgtcag tcgaaagaaa tgtattttag    1320
catctgaatg aatttactgg taataatatt atccacacat ttgcaatggc tggcatctgc    1380
tctattccca ttgctgtctg caggctgtgg ga                                  1412
```

<210> SEQ ID NO 7
<211> LENGTH: 263
<212> TYPE: PRT
<213> ORGANISM: MOUSE

<400> SEQUENCE: 7

Met Phe Val Lys Ser Glu Thr Leu Glu Leu Lys Glu Glu Glu Val
1               5                   10                  15

Leu Met Leu Leu Gly Ser Ala Ser Pro Ala Ser Ala Thr Leu Thr Pro
            20                  25                  30

Met Ser Ser Ser Ala Asp Glu Glu Asp Glu Glu Leu Arg Arg Pro
        35                  40                  45

Gly Ser Ala Arg Gly Gln Arg Gly Ala Glu Ala Gly Gln Gly Val Gln
    50                  55                  60

Gly Ser Pro Ala Ser Gly Ala Gly Gly Cys Arg Pro Gly Arg Leu Leu
65                  70                  75                  80

Gly Leu Met His Glu Cys Lys Arg Arg Pro Ser Arg Ser Arg Ala Val
                85                  90                  95

Ser Arg Gly Ala Lys Thr Ala Glu Thr Val Gln Arg Ile Lys Lys Thr
            100                 105                 110

Arg Arg Leu Lys Ala Asn Asn Arg Glu Arg Asn Arg Met His Asn Leu
        115                 120                 125

Asn Ala Ala Leu Asp Ala Leu Arg Glu Val Leu Pro Thr Phe Pro Glu
    130                 135                 140

Asp Ala Lys Leu Thr Lys Ile Glu Thr Leu Arg Phe Ala His Asn Tyr
145                 150                 155                 160

Ile Trp Ala Leu Thr Glu Thr Leu Arg Leu Ala Asp His Cys Ala Gly
            165                 170                 175

Ala Gly Gly Leu Gln Gly Ala Leu Phe Thr Glu Ala Val Leu Leu Ser
            180                 185                 190

Pro Gly Ala Ala Leu Gly Ala Ser Gly Asp Ser Pro Ser Pro Pro Ser
        195                 200                 205

Ser Trp Ser Cys Thr Asn Ser Pro Ala Ser Ser Asn Ser Thr Ser
    210                 215                 220

Pro Tyr Ser Cys Thr Leu Ser Pro Ala Ser Pro Gly Ser Asp Val Asp
225                 230                 235                 240

Tyr Trp Gln Pro Pro Pro Glu Lys His Arg Tyr Ala Pro His Leu
            245                 250                 255

Pro Leu Ala Arg Asp Cys Ile
            260

<210> SEQ ID NO 8
<211> LENGTH: 1957
<212> TYPE: DNA
<213> ORGANISM: MOUSE

<400> SEQUENCE: 8
gatacacaca gatctagagg ctccaggaga cgatgcgaca ctcagcctga aaagatttgg      60
aagatccaaa atgaaaactg attattgaat gaaattaaaa cctaaggtaa attaaggtta     120
aagaaccatg ttaacactac cgtttgacga gtctgtcgta atgcccgaat cccagatgtg     180
cagaaagttt gctagacaat gtgaggacca gaaacaaatt aagaaccag agagctttcc      240 aaaacaagtt gtccttcgag gaaagagcat taaaagggcc cctggagaag aaaccgagaa     300
agaagaggag gaagaagaca gagaggaaga agatgagaat ggcttgtcca gaaggagggg     360
gctcaggaaa aaaagacca ccaaactacg actggaaagg gtcaagttca ggagacagga      420
agctaatgcg cgcgagagga accggatgca cggcctcaat gatgctctgg acaatttgcg     480
aaaagtggtc ccctgttact ctaaaaccca aaaactgtcc aaaatagaaa ctttacgact     540
ggccaaaaat tacatctggg cactttctga aattctgagg attggcaaga gaccggatct     600
gctcacgttc gtccaaaact tatgcaaagg tctttcccag ccaactacaa acttggtggc     660
aggctgctta cagctcaacg ccagaagttt cctgatgggt cagggtgggg aggctgccca     720
ccacacaagg tcaccctact ccacattcta cccaccctac cacagccctg agctggccac     780 tccccaggg catgggactc ttgataattc aagtccatg aaaccctaca attactgcag       840
tgcatatgaa tccttctatg aaagtacctc ccctgagtgt gccagccctc agtttgaagg     900
tcccttaagt cctcccccaa ttaactataa tgggatattt ccctgaagc aagaagaaac     960 cttggactat ggcaaaaatt acaattatgg catgcattac tgtgcagtgc cacccaggg     1020 tccccttggg cagggtgcca tgttcaggtt gccaccgac agccactcc cttacgactt     1080 acatctgcgc agccaatctc tcactatgca agatgaatta aatgcagttt ttcataatta     1140
atgaggaaaa tgaaaataaa cagtggtcat tcacctccca ctctaattaa ggcaaagcag     1200
atgcttgtgg gctgcgtaat tggcacaact ctatctaagg tgtttactag tttctgaagt     1260
gtgtctcaaa gattgtgacc atttctatg tcataataaa tcccttttcg tatgagaact      1320
tcctttcctt ccctcttgtc tgtatcacac tgtgattctc tctctctctc tctctctctc     1380

-continued

```
tctctctctc tctctctctt actggcagaa tatttctttc ttgttttagt ttcttttcaaa    1440 ttcacttaat ttgtttgaac aaggtgtcta agatgttgct gaataaagac atgcacacag    1500
catacttcaa tgtctatttc agttgtacag ttatgatgaa atgcatgtt ataaaaatca    1560 gatgagtaaa atgtgtttat aattactagg attcatatat gtatctctga aattttagtt    1620
tttaaaatat taagagctaa ccatgaaatt aaaaggtgca tttggggatg cacaacggta    1680
tcaaaagcta tgcaattttc tgtttattag ggacaaaaat aagtgtattc agttggtaac    1740
aactattcct cttcaagcat tttcagagga ggaaacacgg tatttggggg aggttatcag    1800
tgtcataatt tggggacaat taattcaatc atgaagaaaa aaaatattag cacttgtttt    1860
gtattgttca ggattttct gtacaggttt gttacagtgt ataattgtgt tttccatcct    1920
acagtttaaa agcaattaaa catagatatt tccactt                              1957
```

<210> SEQ ID NO 9
<211> LENGTH: 337
<212> TYPE: PRT
<213> ORGANISM: MOUSE

<400> SEQUENCE: 9

```
Met Leu Thr Leu Pro Phe Asp Glu Ser Val Met Pro Glu Ser Gln
1               5                  10                  15

Met Cys Arg Lys Phe Ala Arg Gln Cys Glu Asp Gln Lys Gln Ile Lys
            20                  25                  30

Lys Pro Glu Ser Phe Pro Lys Gln Val Val Leu Arg Gly Lys Ser Ile
        35                  40                  45

Lys Arg Ala Pro Gly Glu Glu Thr Glu Lys Glu Glu Glu Glu Asp
    50                  55                  60

Arg Glu Glu Glu Asp Glu Asn Gly Leu Ser Arg Arg Gly Leu Arg
65                  70                  75                  80

Lys Lys Lys Thr Thr Lys Leu Arg Leu Glu Arg Val Lys Phe Arg Arg
                85                  90                  95

Gln Glu Ala Asn Ala Arg Glu Arg Asn Arg Met His Gly Leu Asn Asp
            100                 105                 110

Ala Leu Asp Asn Leu Arg Lys Val Val Pro Cys Tyr Ser Lys Thr Gln
        115                 120                 125

Lys Leu Ser Lys Ile Glu Thr Leu Arg Leu Ala Lys Asn Tyr Ile Trp
    130                 135                 140

Ala Leu Ser Glu Ile Leu Arg Ile Gly Lys Arg Pro Asp Leu Leu Thr
145                 150                 155                 160

Phe Val Gln Asn Leu Cys Lys Gly Leu Ser Gln Pro Thr Thr Asn Leu
                165                 170                 175

Val Ala Gly Cys Leu Gln Leu Asn Ala Arg Ser Phe Leu Met Gly Gln
            180                 185                 190

Gly Gly Glu Ala Ala His His Thr Arg Ser Pro Tyr Ser Thr Phe Tyr
        195                 200                 205

Pro Pro Tyr His Ser Pro Glu Leu Ala Thr Pro Gly His Gly Thr
    210                 215                 220

Leu Asp Asn Ser Lys Ser Met Lys Pro Tyr Asn Tyr Cys Ser Ala Tyr
225                 230                 235                 240

Glu Ser Phe Tyr Glu Ser Thr Ser Pro Glu Cys Ala Ser Pro Gln Phe
                245                 250                 255

Glu Gly Pro Leu Ser Pro Pro Ile Asn Tyr Asn Gly Ile Phe Ser
            260                 265                 270
```

```
Leu Lys Gln Glu Glu Thr Leu Asp Tyr Gly Lys Asn Tyr Asn Tyr Gly
            275                 280                 285

Met His Tyr Cys Ala Val Pro Pro Arg Gly Pro Leu Gly Gln Gly Ala
            290                 295                 300

Met Phe Arg Leu Pro Thr Asp Ser His Phe Pro Tyr Asp Leu His Leu
305                 310                 315                 320

Arg Ser Gln Ser Leu Thr Met Gln Asp Glu Leu Asn Ala Val Phe His
                325                 330                 335

Asn

<210> SEQ ID NO 10
<211> LENGTH: 1056
<212> TYPE: DNA
<213> ORGANISM: MOUSE

<400> SEQUENCE: 10
atgtcccgcc tgctgcatgc agaagagtgg gctgaggtaa aagagttggg ggaccaccat      60
cgccatcccc agccgcacca cgtcccgccg ctgacgccac agccacctgc taccctgcag     120
gcgagagacc ttcccgtcta cccggcagaa ctgtccctcc tggatagcac cgacccacgc     180
gcctggctga ctcccacttt gcagggcctc tgcacggcac gcgccgccca gtatctgctg     240
cattctcccg agctgggtgc ctccgaggcc gcggcgcccc gggacgaggc tgacagccag     300
ggtgagctgg taaggagaag cggctgtggc ggcctcagca agagcccgg gcccgtcaaa     360
gtacgggaac agctgtgcaa gctgaagggt ggggttgtag tggacgagct ggctgcagc     420
cgccagcgag ccccttccag caaacaggtg aatggggtac agaagcaaag gaggctggca     480
gcaaacgcaa gggaacggcg caggatgcac gggctgaacc acgccttcga ccagctgcgc     540
aacgttatcc cgtccttcaa caacgacaag aagctgtcca atatgagac cctacagatg     600
gcccagatct acatcaacgc tctgtcggag ttgctgcaga ctcccaatgt cggagagcaa     660
ccgccgccgc ccacagcttc ctgcaaaaat gaccaccatc accttcgcac cgcctcctcc     720
tatgaaggag gtgcgggcgc ctctgcggta gctggggctc agccagcccc gggagggggc     780
ccgagaccta ccccgcccgg gccttgccgg actcgcttct caggcccagc ttcctctggg     840
ggttactcgg tgcagctgga cgcttttgcac ttcccagcct cgaggacag ggccctaaca     900
gcgatgatgg cacagaagga cctgtcgcct tcgctgcccg ggggcatcct gcagcctgta     960
caggaggaca cagcaaaac atctcccaga tcccacagaa gtgacggaga gttttccccc    1020
cactctcatt acagtgactc tgatgaggcc agttag                             1056

<210> SEQ ID NO 11
<211> LENGTH: 351
<212> TYPE: PRT
<213> ORGANISM: MOUSE

<400> SEQUENCE: 11

Met Ser Arg Leu Leu His Ala Glu Glu Trp Ala Glu Val Lys Glu Leu
1               5                   10                  15

Gly Asp His His Arg His Pro Gln Pro His His Val Pro Pro Leu Thr
                20                  25                  30

Pro Gln Pro Pro Ala Thr Leu Gln Ala Arg Asp Leu Pro Val Tyr Pro
            35                  40                  45

Ala Glu Leu Ser Leu Leu Asp Ser Thr Asp Pro Arg Ala Trp Leu Thr
    50                  55                  60

Pro Thr Leu Gln Gly Leu Cys Thr Ala Arg Ala Ala Gln Tyr Leu Leu
```

|    |    |    |    |    | 65  |    |    |    |    | 70  |    |    |    |    | 75  |    |    |    |    | 80  |
|---|---|---|---|---|---|---|---|---|---|---|---|---|---|---|---|---|---|---|---|---|

His Ser Pro Glu Leu Gly Ala Ser Glu Ala Ala Pro Arg Asp Glu
                85                  90                  95

Ala Asp Ser Gln Gly Glu Leu Val Arg Arg Ser Gly Cys Gly Gly Leu
            100                 105                 110

Ser Lys Ser Pro Gly Pro Val Lys Val Arg Glu Gln Leu Cys Lys Leu
            115                 120                 125

Lys Gly Gly Val Val Asp Glu Leu Gly Cys Ser Arg Gln Arg Ala
            130                 135                 140

Pro Ser Ser Lys Gln Val Asn Gly Val Gln Lys Gln Arg Arg Leu Ala
145                 150                 155                 160

Ala Asn Ala Arg Glu Arg Arg Met His Gly Leu Asn His Ala Phe
                165                 170                 175

Asp Gln Leu Arg Asn Val Ile Pro Ser Phe Asn Asn Asp Lys Lys Leu
            180                 185                 190

Ser Lys Tyr Glu Thr Leu Gln Met Ala Gln Ile Tyr Ile Asn Ala Leu
            195                 200                 205

Ser Glu Leu Leu Gln Thr Pro Asn Val Gly Glu Gln Pro Pro Pro
210                 215                 220

Thr Ala Ser Cys Lys Asn Asp His His His Leu Arg Thr Ala Ser Ser
225                 230                 235                 240

Tyr Glu Gly Gly Ala Gly Ser Ala Val Ala Gly Ala Gln Pro Ala
                245                 250                 255

Pro Gly Gly Gly Pro Arg Pro Thr Pro Pro Gly Pro Cys Arg Thr Arg
            260                 265                 270

Phe Ser Gly Pro Ala Ser Ser Gly Gly Tyr Ser Val Gln Leu Asp Ala
            275                 280                 285

Leu His Phe Pro Ala Phe Glu Asp Arg Ala Leu Thr Ala Met Met Ala
            290                 295                 300

Gln Lys Asp Leu Ser Pro Ser Leu Pro Gly Gly Ile Leu Gln Pro Val
305                 310                 315                 320

Gln Glu Asp Asn Ser Lys Thr Ser Pro Arg Ser His Arg Ser Asp Gly
                325                 330                 335

Glu Phe Ser Pro His Ser His Tyr Ser Asp Ser Asp Glu Ala Ser
                340                 345                 350

<210> SEQ ID NO 12
<211> LENGTH: 3261
<212> TYPE: DNA
<213> ORGANISM: MOUSE

<400> SEQUENCE: 12
aatctataca tggcaaaaat gtatatgaaa tccaaggaca tggtggagct ggtcaacaca      60
caatcctgga tggacaaagg tctgagctct caaaatgaga tgaaggagca agagagaaga     120
ccgggctctt atggaatgct cggaaccttaa ctgaagagc atgacagtat tgaggaggat     180
gaagaagagg aagaagatgg agataaaacct aaaagaagag gtcccaagaa aaagaagatg     240
actaaagctc gccttgaaag attcagggct cgaagagtca aggccaatgc tagagaacgg     300
acccggatgc atggcctgaa tgatgccttg ataatcttaa ggagagtcat gccatgttac     360
tctaaaactc aaaagctttc caagatagag actcttcgac tggcaaggaa ctacatctgg     420
gccttgtctg aagtcctgga gactggtcag acacttgaag ggaagggatt tgtagagatg     480
ctatgtaaag gtctctctca acccacaagc aacctggttg ctggatgcct ccaactgggg     540

```
cctcaatcta ccctcctgga gaagcatgag gaaaaatctt caatttgtga ctctactatc      600
tctgtccaca gcttcaacta tcagtctcca gggctcccca gccctcctta tggccatatg      660
gaaacacatt ctctccatct caagcctcaa ccatttaaga gtttgggtga ctcttttggg      720
agccatccac ctgactgcag tacccccccct tatgagggtc cactcacacc accectgagc     780 attagtggca acttctcctt aaagcaagac ggctcccctg atttggaaaa atcctacaat      840
ttcatgccac attataccte tgcaagtcta agttcagggc atgtgcattc aactcccttt      900
cagactggca ctccccgcta tgatgttcct gtagacctga gctatgattc ctactcccac      960
catagcattg gaactcagct caatacgatc ttctctgatt agagcaataa gataagcacc     1020
aatatttcag agaatgaagt ggagattttt ttcacatttc tagtggctga gctaaactct     1080
cagaaaattt aaaagaacct ttggatatgc atcaaacata atagtcctag tttgttcaga     1140
acttcctgta cctgctaact ttcttcccat taacttctca cattggacca gtcctacatt     1200
tggtaaactt aagtgaatat atttgatggt ttgaggccac atggtaatag aacagaaaga     1260
aagcccaggc cctgttccaa tggtgccaaa gattaattga atgctctgcc aattaacttt     1320
ccatttccag tgttttttatt gctttctgat aaacatgaag caactgttcc aaatcaacat     1380 ataccttttca cctcccacac attttttaaat ttaaaagcaa tcaaagcaaa tagcaaaaat    1440
ggaatgatta tacagaactg gaaggagcat caagtacatg tctgttggct tatagaatac     1500
aaaatttgtg tgaatttgac aaatcatctt tgtgtctatt taaatataac ttccagagcc     1560
taaaataata acttggatgt taccataaat aaccagtatg ttcttttaaga gatcagctct     1620 acttattact gtgctgaaag gtatacacac ctttttttagt gattggagaa ccatgataga     1680
agcctcacac aaactttatt ctttatacta tttaaaaaac aactgtctta gtactaggag     1740
acaagcaaga aagacattga aatttctctt ctggcacaca gaaatatcac ctagctcatt     1800
tcttagctcc cgtgactata gggctgtaga attttgcagg tattcaggtg cttcagttag     1860
aatcagaact cagccaggtt catactgtag agcaataaaa tggtggttgg ctgctatccc     1920
aactaacaca gttaaagaac tctgcctcac acatagccac tggaaaaatg tggatattct     1980
ccagcaagat gaatttcact gtttaaagca atgcaattaa agccatagag tttcgtccac     2040
tccagtatca tatattccag aactgttgta atcaatcttg aattcttaca acataaatgc     2100
aactccttac ttcccaccta acactgattg ttatattgtc ttcaattcca agatattatg     2160
caattatatg caaaattttg attagaatca aaattaagag tcaatgaatc tgtctgtatc     2220
ttcaggacgg gttttgatca gttttaagaa agtttatttt cctttatgtg gcatctcttt     2280
tctttgtaac cacactggtt cagccaagtt tctcttctcc agagaaatta gctctgagaa     2340
attttactat catgatccat cttccacagc aattatttag gttcaactca agagtataca     2400
tagtttattt atagtgggtg aggatacacc tccaagaata aattttaaca acattaatga     2460
catatgaata tgccattttta tctaccaaac tatatatgta tctcttttct ttattgccct     2520
tatttatttc ttcacactga gagttatttt gtgtccatct tattgcagca cttactctgc     2580
tctactttgc acctttggat tataaatatg tttaaaagtc tgtaaagacg tcttaaacaa     2640
ctcgtgacag taattcacca cccctaagac cttgaatcac cctagtggaa ataggcaagg     2700
agaattattg atagaatcat cctatgtaat ttttttttgag aatttgctct acctagcatt     2760
tatgtttata gataattgct atctgcatta tttattaggt tctatttatt taatttatct     2820 ttcttttcttt ttatgtaaac atttgtgccc catagatata gcctcaaagc ttcactggga     2880
aactagctta tatgtttgga gtgagagaaa aggagaaaat cagttcttga ttgcttgcaa     2940
```

```
tggttttata aaacagagca ataatttgaa tagatatgca acttaatggt tttagaattt    3000
ttcctttaag gtgcaacaga gttacattat tatttatgac tttggagaat gtagtacatg    3060
tgaaccagga ctgtaggctt gtgaagagag atttttataa taaatacaaa tttagtactg    3120
tactatgctt ggaaagaact tgttctttaa ataatgttta gtcttctggg agtgttttca    3180
gataaaatga agcaattgtt taaaagaaat ggctgttttc cctcccttt ccagtagcaa     3240 taaagctttg agtgttatta c                                              3261

<210> SEQ ID NO 13
<211> LENGTH: 501
<212> TYPE: DNA
<213> ORGANISM: ZEBRA FISH
<220> FEATURE:
<221> NAME/KEY: misc_feature
<222> LOCATION: (115)..(115)
<223> OTHER INFORMATION: n can be any nucleotide

<400> SEQUENCE: 13
atgttaacgg taccgtttga agagccagat atgatgcgcg agtctcagtt tggcgccacg    60
ttcacgcgtc aggaagacgt ccggacactc agcagcgccg agctcaagga ggcanaggac    120
gacaacacgg acagggagga ggaggaggag agagaggagg actataacgg gctgccaaag    180
aagaagggtc cccgcaaaaa gaaatccgag ggacgcggtg accgagtcaa aatgcgccgt    240
caggaagcaa acgcgcgtga gcgcagccgc atgcacggtc taaacgacgc gctcgaaagc    300
ctgcgcaaag tcgtgccgtg ctactccaaa acgcagaaac tctccaagat cgaaaccctg    360
gggctgggca agaattacat ttgggctctg tctgagactt tgagcgcagg aaagcgacct    420
ggcctgcttg ggttggtagc aaccctgggc gtgggctggt ctagaggaca gaccagcttg    480
gtgggggagt gcctgcagct a                                              501

<210> SEQ ID NO 14
<211> LENGTH: 609
<212> TYPE: DNA
<213> ORGANISM: HUMAN

<400> SEQUENCE: 14
tttgacattg aattatgctg tgtgcatgtc tttattcaac agtatattct tagacacctt    60
gttcaaacaa attaaataag tttaaaagaa aattaaaaag aaaaaaatct ttccagtaga    120
aacagaatca cagtgcttca cagacaaaag gaaaggaaaa gaagttctca tacgaaagaa    180
gatttattat tacatagaaa attctcacaa tagttgaaac acacttcaga aactagtaaa    240
caccttagat agagttgtgc caattactca gcccacaagc atctgctttg tcttaattag    300 acagggagg tgaatgacca ctgtttattt tcatttttcct cattaattat gaaaaactgc     360
atttaattca tcttgcattg tgagagattg gctgcgcaga tgtaagtcgt aagggaagtg    420
gctgtcggtg ggcaacctga acatggcacc ctgcccaagg ggaccctgg gtggcactgc     480 acagtaatgc atgccgtaat tgtaattttt accatagtcc aaggtttctt cttgcttcag    540
ggaaaatatc ccattatagg taattggggg aggacttaag ggaccttcaa actgagggct    600
ggcacactc                                                            609

<210> SEQ ID NO 15
<211> LENGTH: 675
<212> TYPE: DNA
<213> ORGANISM: HUMAN
```

```
<400> SEQUENCE: 15
tagagagcgg caggagacga tgcgacactc agcctgaaaa gatttggaag acccaaaatg    60
aaaactgatt attgaatgaa attaaaacct aaggtaattt aagattagag aaccatgtta   120
acactaccgt ttgatgagtc tgttgtaatg ccagaatccc agatgtgcag aaagttttct   180
agagaatgcg aggaccagaa gcaaattaag aagccagaaa gcttttccaa acagattgtc   240
cttcgaggaa agagcatcaa aagggcccct ggagaagaaa ccgagaaaga agaaggag     300 gaagacaggg aagaggaaga tgaaaatggg ttgcctagaa ggaggggtct taggaaaaaa   360
aagacaacaa agctgcgatt ggaaagggtc aagttcagga acaggaagc gaacgcgcgc   420 gagaggaaca ggatgcacgg cctcaacgac gctctggaca acttaagaaa agtggtccgc   480
tgttattcta tgacccagag actgtccaaa atagagactg tactactggc aaaaactac    540 atctgggcac tgtctgatat gctgagaatc ggcaagagac cagatctgct cacgattcgg   600
caaagctgat gcatagggtc ttgccagcca actacagact tggtggcagg ctggtcgcag   660
ctcaacgaca ggagt                                                    675

<210> SEQ ID NO 16
<211> LENGTH: 1476
<212> TYPE: DNA
<213> ORGANISM: DROSPHILA
<220> FEATURE:
<221> NAME/KEY: misc_feature
<222> LOCATION: (203)..(217)
<223> OTHER INFORMATION: n can be any nucleotide

<400> SEQUENCE: 16
ctccaccctc gtgtgccgtt gagcgtgaaa gtcacaaatt atgggcgaca gagggagagg    60
gagagagaga gaggggaaga tcccatggca tgatagtacc aatttggcaa gatatgacgc   120
gtgcctggcg cgagagagat gacaacaggc gaagtgtagg cgtttcacca ccgagcgaaa   180
gggagggaaa catatctaac ccntaagtca ccccagntcc tcgggagat cctttggccg    240 ggccatggta atagctgcga ggatcctggg gccaggggtc atttgcgggc catttacaca   300
aacttggtca gaacggcggt gaaaatattt gtagaatgca tctcgcgggg gttgaccgta   360
gtcaagtctg gatccgatcg gatcgtttca gttgcaacga actttcaag ccgcgcggat    420 ctgcaatgag ctactactac tcgtctgcct ccgaggagga tggcagttcc cagtatctgg   480
gcagtcccaa ctacaacttg acccagttgc cgccagtttc tggccaggat acgacagg     540 gggctttctt atcgccggaa tggcaattct tggatgccgc aggcggaact caaacggaac   600
taggacccat aatggaggtg caaggacagc acacccagcc gcagaccaaa cggcggagta   660
acagctccac aggatcggac ggtaggaaga gcagtccaga gcagaccaat ctcagtccca   720
cggtccagaa gagaagacga caggctgcca atgcgcggga aggaagcgg atgaatggat    780 taaatgcggc tttcgagcgc ctaagggaag tggtgcccgc tccgtccatt gaccagaaat   840
tgtccaagtt cgagactctc cagatggccc agtcctacat cctggcgctg tgcgatctcc   900
tcaacaacgg gacgtggaa gtggatgccg ctgcatacac catcttcggc gacagcgata    960
gtggatttgg attgagcgga ggatccttgt catagatgga tgatactaga ctaaagttat  1020
gtgattttct tcttactgta gattaagtta aatatgtaat gaaataaatt gaatgttta    1080 attgaatgct aaaaataatt tcaatttcaa aggcattatt catggaacgc atcgcttgat  1140
tgtgaaccaa gtgttcaatc caaaatgagc tactcatcta accctttcta ccaattataa  1200
ccagcccact actatacaca gatccccaga ttcaattggc catcagatcg tttggctgcg  1260
```

-continued

```
cctcaatgat ttcgaaaacg atcataaatt aattactcaa cagttcattg ataggcgtac    1320
ttcaagtttt grtctaaccc cgaacgattc cgaaactgcg aagccaccac agtgggcggt    1380
gtagcgtgac acccctgaac tcctggccag aactcctctc attgaataaa aaaggcagct    1440
gagtccttcg gcttcggttg ggtgctgttt tttttt                              1476
```

<210> SEQ ID NO 17
<211> LENGTH: 189
<212> TYPE: PRT
<213> ORGANISM: DROSOPHILA

<400> SEQUENCE: 17

```
Met Ser Tyr Tyr Tyr Ser Ser Ala Ser Glu Glu Asp Gly Ser Ser Gln
1               5                   10                  15

Tyr Leu Gly Ser Pro Asn Tyr Asn Leu Thr Gln Leu Pro Pro Val Ser
            20                  25                  30

Gly Gln Asp Tyr Gly Gln Gly Ala Phe Leu Ser Pro Glu Trp Gln Phe
        35                  40                  45

Leu Asp Ala Ala Gly Gly Thr Gln Thr Glu Leu Gly Pro Ile Met Glu
    50                  55                  60

Val Gln Gly Gln His Thr Gln Pro Gln Thr Lys Arg Arg Ser Asn Ser
65                  70                  75                  80

Ser Thr Gly Ser Asp Gly Arg Lys Ser Ser Pro Glu Gln Thr Asn Leu
                85                  90                  95

Ser Pro Thr Val Gln Lys Arg Arg Arg Gln Ala Ala Asn Ala Arg Glu
            100                 105                 110

Arg Lys Arg Met Asn Gly Leu Asn Ala Ala Phe Glu Arg Leu Arg Glu
        115                 120                 125

Val Val Pro Ala Pro Ser Ile Asp Gln Lys Leu Ser Lys Phe Glu Thr
    130                 135                 140

Leu Gln Met Ala Gln Ser Tyr Ile Leu Ala Leu Cys Asp Leu Leu Asn
145                 150                 155                 160

Asn Gly Asp Val Glu Val Asp Ala Ala Ala Tyr Thr Ile Phe Gly Asp
                165                 170                 175

Ser Asp Ser Gly Phe Gly Leu Ser Gly Gly Ser Leu Ser
            180                 185
```

<210> SEQ ID NO 18
<211> LENGTH: 1074
<212> TYPE: DNA
<213> ORGANISM: CHICKEN

<400> SEQUENCE: 18

```
ttttccttt cccttttcct cgcggagccg cggccgcttt gccttcccct acagcgagga     60
gctccgcttt ctcctctatt tatttctaaa ccgttattgc ttaaccgcag ccccgggagt    120
gcctttccat gtgagtacgg gggacacagg cacctgcgat gcggtgcggc cgtgccaagc    180
actcccaccc tccctccgtc cctccttggg gttactttgg gatatttttt ccctcccttt    240 cccctcccc tcagcacctt ccccccgctc ccctgccgc ccactgacgg ctccggcttc    300
tctcccgcag gatgcccgcg gaggcggcga gcagcggcgg cgtttcggag ccgcccggag    360
ctccgcggga gcggcggagg agacgcggcc gtgcgcgggc gcggaccgag gctttgctgc    420
acaccctcaa acggagccgc cgggtgaaag ccaacgaccg ggagcggaac cgcatgcacc    480
acctcaacgc gcgcgctggat gagctccgca gcgtcctgcc gacctccccc gacgacacca    540
```

```
aactcaccaa aatcgaaacc ctgcgcttcg cttacaacta catctgggcc ctctccgaga    600
cccttcgttt ggccgagcag tgcctccctc ctcccccgc cttccgcggg ccccccgcgc    660
cccccagccc cggcagcgac gccggttcgt ggctgtccag cggttccccg gccgccccct    720
cgctctgcgc ctccgcctcc ggcccagca gcccggccac ctccgaggac tgcggctacg    780
tccctcgga cgccctgcgg gccttccgcg gctgccccc cgccgcccg ggcgctccct    840
gccgctagcc ctgccgtgc gtgtctccgt ccccccccac cttctccgta tcccgttgca    900
cttttcagcc cctcccgccc ccagcccct ctctccgggg tgccctttcc cttcgccccc    960
ccgcctcgtt ttccatacga cttggaaaac ccggcaaaga aaagcgacag atttgctgcc   1020
gcagacgagg tgaaaagtca attttacaat ttgtagctct ccggtgaaga aaaa          1074

<210> SEQ ID NO 19
<211> LENGTH: 178
<212> TYPE: PRT
<213> ORGANISM: CHICKEN

<400> SEQUENCE: 19

Met Pro Ala Glu Ala Ala Ser Ser Gly Gly Val Ser Glu Pro Pro Gly
1               5                   10                  15

Ala Pro Arg Glu Arg Arg Arg Gly Arg Ala Arg Ala Arg Thr
            20                  25                  30

Glu Ala Leu Leu His Thr Leu Lys Arg Ser Arg Arg Val Lys Ala Asn
        35                  40                  45

Asp Arg Glu Arg Asn Arg Met His His Leu Asn Ala Ala Leu Asp Glu
    50                  55                  60

Leu Arg Ser Val Leu Pro Thr Phe Pro Asp Asp Thr Lys Leu Thr Lys
65                  70                  75                  80

Ile Glu Thr Leu Arg Phe Ala Tyr Asn Tyr Ile Trp Ala Leu Ser Glu
                85                  90                  95

Thr Leu Arg Leu Ala Glu Gln Cys Leu Pro Pro Pro Ala Phe Arg
            100                 105                 110

Gly Pro Pro Ala Pro Pro Ser Pro Gly Ser Asp Ala Gly Ser Trp Leu
        115                 120                 125

Ser Ser Gly Ser Pro Ala Ala Pro Ser Leu Cys Ala Ser Ala Ser Gly
    130                 135                 140

Pro Ser Ser Pro Ala Thr Ser Glu Asp Cys Gly Tyr Val Pro Ser Asp
145                 150                 155                 160

Ala Leu Arg Ala Phe Arg Gly Leu Pro Pro Ala Ala Pro Gly Ala Pro
                165                 170                 175

Cys Arg

<210> SEQ ID NO 20
<211> LENGTH: 790
<212> TYPE: DNA
<213> ORGANISM: CHICKEN

<400> SEQUENCE: 20
gcagccgccg ggcccccggg ccgctccgac gccgcccggg cgcgtgccag cgcccccga     60
ccgcccgacg gccgtcgacc agcggccgcg ccccctctc cccgcccccc gcaggatgcc    120
ggtgaaggcg gagagcccgg cgcccgcggc ggaggacgaa ctgctgctgc tgcgcctcgc    180
ctcgcccgcc ccctcggcct cgctgccgtc cagcgccggc gaggaggacg aggacgagga    240
ggacgggcgg ccgcggcggc tgcaggaggg cgctcggcgg gcggggcggc agcgagggcc    300
```

-continued

```
cccgcgggcg gcgcgcacgg cggagacggc gcagcgcatc aagcggagcc ggcggctgaa      360
agccaacaac cgcgagcgca accgcatgca caacctgaac gcggcgctgg acgcgctgcg      420
cgacgtgctg cccaccttcc ccgaggacgc caagctcacc aagatcgaga cgctgcgctt      480
cgcccacaac tacatctggg cgctcaccga gacgctgcgc ctggccgggg ccgcccgcct      540 gggggggcgcc gccgacgccg cgccggggc ggccgccgag ggcagcccct cgcccgcctc      600
gtcgtggagc ggcggcgcca gccccgcgcc ctccgcctcg ccctacgcct gcactttatc      660
gcccggcagc ccgccggct cgcctcgga cgccgagcac tggccgcccc cgcggggccg      720
cttcgccccg ccgccgccgc cccaccgctg cctctaacgc ggcccgggcg gccctcgctc      780
ctccgacgtg                                                              790
```

<210> SEQ ID NO 21
<211> LENGTH: 213
<212> TYPE: PRT
<213> ORGANISM: CHICKEN

<400> SEQUENCE: 21

```
Met Pro Val Lys Ala Glu Ser Pro Ala Pro Ala Ala Glu Asp Glu Leu
1               5                  10                  15

Leu Leu Leu Arg Leu Ala Ser Pro Ala Pro Ser Ala Ser Leu Pro Ser
            20                  25                  30

Ser Ala Gly Glu Glu Asp Glu Asp Glu Glu Asp Gly Arg Pro Arg Arg
        35                  40                  45

Leu Gln Glu Gly Ala Arg Arg Ala Gly Arg Gln Arg Gly Pro Pro Arg
    50                  55                  60

Ala Ala Arg Thr Ala Glu Thr Ala Gln Arg Ile Lys Arg Ser Arg Arg
65                  70                  75                  80

Leu Lys Ala Asn Asn Arg Glu Arg Asn Arg Met His Asn Leu Asn Ala
                85                  90                  95

Ala Leu Asp Ala Leu Arg Asp Val Leu Pro Thr Phe Pro Glu Asp Ala
            100                 105                 110

Lys Leu Thr Lys Ile Glu Thr Leu Arg Phe Ala His Asn Tyr Ile Trp
        115                 120                 125

Ala Leu Thr Glu Thr Leu Arg Leu Ala Gly Ala Ala Arg Leu Gly Gly
    130                 135                 140

Ala Ala Asp Ala Ala Pro Gly Ala Ala Ala Glu Gly Ser Pro Ser Pro
145                 150                 155                 160

Ala Ser Ser Trp Ser Gly Gly Ala Ser Pro Ala Pro Ser Ala Ser Pro
                165                 170                 175

Tyr Ala Cys Thr Leu Ser Pro Gly Ser Pro Ala Gly Ser Ala Ser Asp
            180                 185                 190

Ala Glu His Trp Pro Pro Arg Gly Arg Phe Ala Pro Pro Pro Pro
        195                 200                 205

Pro His Arg Cys Leu
    210
```

<210> SEQ ID NO 22
<211> LENGTH: 450
<212> TYPE: DNA
<213> ORGANISM: MOUSE

<400> SEQUENCE: 22

```
atgaagtcgg cctgcaaacc ccacggccct ccggcgggag ctcgcggcgc gccccgtgc       60 gcgggcgcag ccgagcgcgc ggtctcgtgc gcggggcccg ggcggctgga gagcgcggcg      120
```

| | |
|---|---|
| cgcaggcgtc tggcggccaa cgcgcgcgag cggcgccgca tgcaggggct gaacacggcg | 180 |
| ttcgaccggc tgcgcagggt ggtgccgcag tggggccagg acaagaagct gtccaagtac | 240 |
| gagacactgc agatggcgct cagctacatc atcgcgctca cccgcatcct agccgaagcc | 300 |
| gagcgggact gggtcgggct gcgctgcgag cagcggggcc gcgatcaccc ctacctccct | 360 |
| ttcccgggtg ctaggctcca ggtagaccct gagccctatg gcagaggct cttcggcttc | 420 |
| cagccggagc ccttccccat ggccagctaa | 450 |

<210> SEQ ID NO 23
<211> LENGTH: 149
<212> TYPE: PRT
<213> ORGANISM: MOUSE

<400> SEQUENCE: 23

Met Lys Ser Ala Cys Lys Pro His Gly Pro Pro Ala Gly Ala Arg Gly
1               5                   10                  15

Ala Pro Pro Cys Ala Gly Ala Ala Glu Arg Ala Val Ser Cys Ala Gly
            20                  25                  30

Pro Gly Arg Leu Glu Ser Ala Ala Arg Arg Leu Ala Ala Asn Ala
        35                  40                  45

Arg Glu Arg Arg Arg Met Gln Gly Leu Asn Thr Ala Phe Asp Arg Leu
    50                  55                  60

Arg Arg Val Val Pro Gln Trp Gly Gln Asp Lys Lys Leu Ser Lys Tyr
65                  70                  75                  80

Glu Thr Leu Gln Met Ala Leu Ser Tyr Ile Ile Ala Leu Thr Arg Ile
                85                  90                  95

Leu Ala Glu Ala Glu Arg Asp Trp Val Gly Leu Arg Cys Glu Gln Arg
            100                 105                 110

Gly Arg Asp His Pro Tyr Leu Pro Phe Pro Gly Ala Arg Leu Gln Val
        115                 120                 125

Asp Pro Glu Pro Tyr Gly Gln Arg Leu Phe Gly Phe Gln Pro Glu Pro
    130                 135                 140

Phe Pro Met Ala Ser
145

<210> SEQ ID NO 24
<211> LENGTH: 861
<212> TYPE: DNA
<213> ORGANISM: MOUSE

<400> SEQUENCE: 24

| | |
|---|---|
| attcttttga gtcgggagaa ctaggtaaca attcggaaac tccaaagggt ggatgagggg | 60 |
| cgcgcgggt gtgtgtgggg gatactctgg tcccccgtgc agtgacctct aagtcagagg | 120 |
| ctggcacaca cacaccttcc attttttccc aaccgcagga tggcgcctca tcccttggat | 180 |
| gcgctcacca tccaagtgtc cccagagaca caacaaccct ttcccggagc ctcggaccac | 240 |
| gaagtgctca gttccaattc cacccccacct agccccactc tcatacctag ggactgctcc | 300 |
| gaagcagaag tgggtgactg ccgagggacc tcgaggaagc tccgcgcccg acgcggaggg | 360 |
| cgcaacaggc ccaagagcga gttggcactc agcaaacagc gaagaagccg gcgcaagaag | 420 |
| gccaatgatc gggagcgcaa tcgcatgcac aacctcaact cggcgctgga tgcgctgcgc | 480 |
| ggtgtcctgc ccaccttccc ggatgacgcc aaacttacaa agatcgagac cctgcgcttc | 540 |
| gcccacaact acatctgggc actgactcag acgctgcgca tagcggacca cagcttctat | 600 |

```
ggcccggagc ccctgtgcc ctgtggagag ctggggagcc ccggaggtgg ctccaacggg     660
gactggggct ctatctactc cccagtctcc caagcgggta acctgagccc cacggcctca     720
ttggaggaat ccctggcct gcaggtgcca agctccccat cctatctgct cccgggagca      780
ctggtgttct cagacttctt gtgaagagac ctgtctggct ctgggtggtg ggtgctagtg     840
gaaagggagg ggaccacagc c                                                861
```

<210> SEQ ID NO 25
<211> LENGTH: 214
<212> TYPE: PRT
<213> ORGANISM: MOUSE

<400> SEQUENCE: 25

```
Met Ala Pro His Pro Leu Asp Ala Leu Thr Ile Gln Val Ser Pro Glu
 1               5                  10                  15

Thr Gln Gln Pro Phe Pro Gly Ala Ser Asp His Glu Val Leu Ser Ser
             20                  25                  30

Asn Ser Thr Pro Pro Ser Pro Thr Leu Ile Pro Arg Asp Cys Ser Glu
         35                  40                  45

Ala Glu Val Gly Asp Cys Arg Gly Thr Ser Arg Lys Leu Arg Ala Arg
     50                  55                  60

Arg Gly Gly Arg Asn Arg Pro Lys Ser Glu Leu Ala Leu Ser Lys Gln
 65                  70                  75                  80

Arg Arg Ser Arg Arg Lys Lys Ala Asn Asp Arg Glu Arg Asn Arg Met
                 85                  90                  95

His Asn Leu Asn Ser Ala Leu Asp Ala Leu Arg Gly Val Leu Pro Thr
            100                 105                 110

Phe Pro Asp Asp Ala Lys Leu Thr Lys Ile Glu Thr Leu Arg Phe Ala
        115                 120                 125

His Asn Tyr Ile Trp Ala Leu Thr Gln Thr Leu Arg Ile Ala Asp His
    130                 135                 140

Ser Phe Tyr Gly Pro Glu Pro Pro Val Pro Cys Gly Glu Leu Gly Ser
145                 150                 155                 160

Pro Gly Gly Gly Ser Asn Gly Asp Trp Gly Ser Ile Tyr Ser Pro Val
                165                 170                 175

Ser Gln Ala Gly Asn Leu Ser Pro Thr Ala Ser Leu Glu Glu Phe Pro
            180                 185                 190

Gly Leu Gln Val Pro Ser Ser Pro Ser Tyr Leu Leu Pro Gly Ala Leu
        195                 200                 205

Val Phe Ser Asp Phe Leu
    210
```

<210> SEQ ID NO 26
<211> LENGTH: 72
<212> TYPE: DNA
<213> ORGANISM: MOUSE

<400> SEQUENCE: 26

```
atgcacgggc tgaatgcggc gctggacaac ccgagaaagg tggtaccttg ctactctaag     60
acacagaagc tc                                                          72
```

<210> SEQ ID NO 27
<211> LENGTH: 24
<212> TYPE: PRT
<213> ORGANISM: MOUSE

<400> SEQUENCE: 27

Met His Gly Leu Asn Ala Ala Leu Asp Asn Pro Arg Lys Val Val Pro
1               5                   10                  15

Cys Tyr Ser Lys Thr Gln Lys Leu
            20

<210> SEQ ID NO 28
<211> LENGTH: 66
<212> TYPE: DNA
<213> ORGANISM: MOUSE

<400> SEQUENCE: 28
atgcatggcc tgaatgatgc cttggataat cttagaagag tcatgccatg ttactctaaa    60
actcaa                                                              66

<210> SEQ ID NO 29
<211> LENGTH: 22
<212> TYPE: PRT
<213> ORGANISM: MOUSE

<400> SEQUENCE: 29

Met His Gly Leu Asn Asp Ala Leu Asp Asn Leu Arg Arg Val Met Pro
1               5                   10                  15

Cys Tyr Ser Lys Thr Gln
            20

<210> SEQ ID NO 30
<211> LENGTH: 1385
<212> TYPE: DNA
<213> ORGANISM: MOUSE

<400> SEQUENCE: 30
cttaggaagc gccaagcccg cggagcggag gacaccgtgc tcggttccgg gtgggggaca    60
ttcccggaca cacccggag cagcagctgc gccggaacat ggagccgcg taggtaagtg     120 tgcatgccgc ggcttttccat tcgcaggcag tgtccccacg caggctcacg ccgcccacgc   180
taactccatc gtttagacgc agtgacttct gtgaccggca aaggtggct cgagcccggg    240 gcgctcctcc ccagctctgt cctcgccatc ttcgcgaatg cacattgagg gagatggagg   300 gggggggggcg gggcgcggcg ccagcgacac tttaccctgt ccattctggg aataaatttc   360
atctgcctct tctttctcag gatgttcgtc aaatctgaga ctctggagtt gaaggaggaa   420
gaggaggtac tgatgctgct gggctcggct tccccggcct cggcgaccct gaccccgatg   480
tcctccagcg cggacgagga ggaggacgag gagctgcgcc ggccgggctc cgcgcgtggg   540
cagcgtggag cggaagccga gcaggggtg cagggcagtc cggcgtcggg tgccgggggt    600
tgccggccag ggcggctgct gggcctgatg cacgagtgca agcgtcgccc gtcgcgctca   660
cgggccgtct cccgaggtgc caagacggcg gagacggtgc agcgcatcaa gaagacccgc   720
aggctcaagg ccaacaaccg cgagcgcaac cgcatgcaca acctaaacgc cgcgctggac   780
gcgctgcgcg aggtgctgcc cacccttccc gaggatgcca agctcacgaa gatcgagacg   840
ctgcgcttcg cccacaatta catctgggcg ctcaccgaga ctctgcgcct ggcggaccac   900
tgcgccggcg ccgtggcct ccaggggcg ctcttcacgg aggcggtgct cctgagcccg    960
ggagctgcgc tcggcgccag cggggacagc ccttctccac cttcctcctg gagctgcacc   1020
aacagcccgg cgtcatcctc caactccacg tccccataca gctgcacttt atcgcccgct   1080
agccccgggt cagacgtgga ctactggcag ccccacctc cggagaagca tcgttatgcg    1140

-continued

```
cctcacctgc ccctcgccag ggactgtatc tagagctgcg ggtctccctc tctcgtctcc    1200
tacccgggcc ctccttccca tccttctccc gccccccacc ctccacgccc cggaatccac    1260
ttcacagaac agaagttggc cctttgcaat cccctccgcg gctggtgctt cgggggttgg    1320
aaaacaactc tggtttattg aaattaagat tttggtcaaa agaatatgc ttttggaat     1380 tgggg                                                               1385
```

<210> SEQ ID NO 31
<211> LENGTH: 263
<212> TYPE: PRT
<213> ORGANISM: MOUSE

<400> SEQUENCE: 31

```
Met Phe Val Lys Ser Glu Thr Leu Glu Leu Lys Glu Glu Glu Glu Val
1               5                   10                  15

Leu Met Leu Leu Gly Ser Ala Ser Pro Ala Ser Ala Thr Leu Thr Pro
            20                  25                  30

Met Ser Ser Ser Ala Asp Glu Glu Asp Glu Glu Leu Arg Arg Pro
        35                  40                  45

Gly Ser Ala Arg Gly Gln Arg Gly Ala Glu Ala Glu Gln Gly Val Gln
    50                  55                  60

Gly Ser Pro Ala Ser Gly Ala Gly Gly Cys Arg Pro Gly Arg Leu Leu
65                  70                  75                  80

Gly Leu Met His Glu Cys Lys Arg Arg Pro Ser Arg Ser Arg Ala Val
                85                  90                  95

Ser Arg Gly Ala Lys Thr Ala Glu Thr Val Gln Arg Ile Lys Lys Thr
            100                 105                 110

Arg Arg Leu Lys Ala Asn Asn Arg Glu Arg Asn Arg Met His Asn Leu
        115                 120                 125

Asn Ala Ala Leu Asp Ala Leu Arg Glu Val Leu Pro Thr Phe Pro Glu
    130                 135                 140

Asp Ala Lys Leu Thr Lys Ile Glu Thr Leu Arg Phe Ala His Asn Tyr
145                 150                 155                 160

Ile Trp Ala Leu Thr Glu Thr Leu Arg Leu Ala Asp His Cys Ala Gly
                165                 170                 175

Ala Gly Gly Leu Gln Gly Ala Leu Phe Thr Glu Ala Val Leu Leu Ser
            180                 185                 190

Pro Gly Ala Ala Leu Gly Ala Ser Gly Asp Ser Pro Ser Pro Pro Ser
        195                 200                 205

Ser Trp Ser Cys Thr Asn Ser Pro Ala Ser Ser Asn Ser Thr Ser
    210                 215                 220

Pro Tyr Ser Cys Thr Leu Ser Pro Ala Ser Pro Gly Ser Asp Val Asp
225                 230                 235                 240

Tyr Trp Gln Pro Pro Pro Glu Lys His Arg Tyr Ala Pro His Leu
                245                 250                 255

Pro Leu Ala Arg Asp Cys Ile
            260
```

<210> SEQ ID NO 32
<211> LENGTH: 3541
<212> TYPE: DNA
<213> ORGANISM: MOUSE

<400> SEQUENCE: 32

```
cagctgggca aggaaaatat gaaacacaag tgatctatat ccacagaata aacactaagt    60
```

```
ttatgtgtct tttgacaagg tctcatgtag ctcagactgg ggttaaactt tttatgctac   120
taaagataaa cttcaatatg ctaataaaga taaactcctg attttctgc ttccacctct    180
taaggcttgg gatcataggc atgtgccatc atgtctttct cagtttagat ttataccagg   240
tattttgtgg tataacattt ttatattttc cttttccag aatctataca tggcaaaaat    300
gtatatgaaa tccaaggaca tggtggagct ggtcaacaca caatcctgga tggacaaagg   360
tctgagctct caaaatgaga tgaaggagca agagagaaga ccgggctctt atggaatgct   420
cggaacctta actgaagagc atgacagtat tgaggaggat gaagaagagg aagaagatgg   480
agataaacct aaaagaagag gtcccaagaa aaagaagatg actaaagctc gccttgaaag   540
attcagggct cgaagagtca aggccaatgc tagagaacgg acccggatgc atggcctgaa   600
tgatgccttg gataatctta ggagagtcat gccatgttac tctaaaactc aaaagctttc   660
caagatagag actcttcgac tggcaaggaa ctacatctgg gccttgtctg aagtcctgga   720
gactggtcag acacttgaag ggaagggatt tgtagagatg ctatgtaaag gtctctctca   780
acccacaagc aacctggttg ctggatgcct ccaactgggg cctcaatcta ccctcctgga   840
gaagcatgag gaaaaatctt caatttgtga ctctactatc tctgtccaca gcttcaacta   900
tcagtctcca gggctcccca gccctcctta tggccatatg gaaacacatt ctctccatct   960
caagcctcaa ccatttaaga gtttgggtga ctcttttggg agccatccac ctgactgcag  1020
tacccccccct tatgagggtc cactcacacc accctgagc attagtggca acttctcctt  1080
aaagcaagac ggctccctg atttggaaaa atcctacaat ttcatgccac attatacctc   1140
tgcaagtcta agttcagggc atgtgcattc aactcccttt cagactggca ctcccgcta   1200
tgatgttcct gtagacctga gctatgatc ctactccac catagcattg gaactcagct    1260
caatacgatc ttctctgatt agagcaataa gataagcacc aatatttcag agaatgaagt   1320
ggagatttt ttcacatttc tagtggctga gctaaactct cagaaaattt aaaagaacct    1380
ttggatatgc atcaaacata atagtcctag tttgttcaga acttcctgta cctgctaact   1440
ttcttcccat taacttctca cattggacca gtcctacatt tggtaaactt aagtgaatat   1500
atttgatggt ttgaggccac atggtaatag aacagaaaga aagcccaggc cctgttccaa   1560
tggtgccaaa gattaattga atgctctgcc aattaacttt ccatttccag tgttttatt    1620
gctttctgat aaacatgaag caactgttcc aaatcaacat atacctttca cctcccacac   1680
attttaaat ttaaaagcaa tcaaagcaaa tagcaaaaat ggaatgatta tacagaactg    1740
gaaggagcat caagtacatg tctgttggct tatagaatac aaaatttgtg tgaatttgac   1800
aaatcatctt tgtgtctatt taaatataac ttccagagcc taaaataata acttggatgt   1860
taccataaat aaccagtatg ttctttaaga gatcagctct acttattact gtgctgaaag   1920
gtatacacac cttttttagt gattggagaa ccatgataga agcctcacac aaactttatt   1980
ctttatacta tttaaaaaac aactgtctta gtactaggag acaagcaaga aagacattga   2040
aatttctctt ctggcacaca gaaatatcac ctagctcatt tcttagctcc cgtgactata   2100
gggctgtaga atttgcagg tattcagtg cttcagttag aatcagaact cagccaggtt    2160
catactgtag agcaataaaa tggtggttgg ctgctatccc aactaacaca gttaaagaac   2220
tctgcctcac acatagccac tggaaaaatg tggatattct ccagcaagat gaatttcact   2280
gtttaaagca atgcaattaa agccatagag tttcgtccac tccagtatca tatattccag   2340
aactgttgta atcaatcttg aattcttaca acataaatgc aactcctac ttcccaccta    2400
acactgattg ttatattgtc ttcaattcca agatattatg caattatatg caaaattttg   2460
```

```
attagaatca aaattaagag tcaatgaatc tgtctgtatc ttcaggacgg gttttgatca    2520
gttttaagaa agtttatttt cctttatgtg gcatctcttt tctttgtaac cacactggtt    2580
cagccaagtt tctcttctcc agagaaatta gctctgagaa attttactat catgatccat    2640
cttccacagc aattatttag gttcaactca agagtataca tagtttattt atagtgggtg    2700
aggatacacc tccaagaata aattttaaca acattaatga catatgaata tgccatttta    2760
tctaccaaac tatatatgta tctcttttct ttattgccct tatttatttc ttcacactga    2820
gagttatttt gtgtccatct tattgcagca cttactctgc tctactttgc acctttggat    2880
tataaatatg tttaaaagtc tgtaaagacg tcttaaacaa ctcgtgacag taattcacca    2940
cccctaagac cttgaatcac cctagtggaa ataggcaagg agaattattt atagaatcat    3000
cctatgtaat ttttttttgag aatttgctct acctagcatt tatgtttata gataattgct    3060
atctgcatta tttattaggt tctatttatt taatttatct ttctttcttt ttatgtaaac    3120
atttgtgccc catagatata gcctcaaagc ttcactggga aactagctta tatgtttgga    3180
gtgagagaaa aggagaaaat cagttcttga ttgcttgcaa tggttttata aaacagagca    3240
ataatttgaa tagatatgca acttaatggt tttagaattt ttcctttaag gtgcaacaga    3300
gttacattat tatttatgac tttggagaat gtagtacatg tgaaccagga ctgtaggctt    3360
gtgaagagag attttataat taaatacaaa tttagtactg tactatgctt ggaaagaact    3420
tgttctttaa ataatgttta gtcttctggg agtgttttca gataaaatga agcaattgtt    3480
taaaagaaat ggctgttttc cctcccttt ccagtagcaa taaagctttg agtgttatta    3540
c                                                                  3541
```

<210> SEQ ID NO 33
<211> LENGTH: 330
<212> TYPE: PRT
<213> ORGANISM: MOUSE

<400> SEQUENCE: 33

```
Met Ala Lys Met Tyr Met Lys Ser Lys Asp Met Val Glu Leu Val Asn
1               5                   10                  15

Thr Gln Ser Trp Met Asp Lys Gly Leu Ser Ser Gln Asn Glu Met Lys
            20                  25                  30

Glu Gln Glu Arg Arg Pro Gly Ser Tyr Gly Met Leu Gly Thr Leu Thr
        35                  40                  45

Glu Glu His Asp Ser Ile Glu Glu Asp Glu Glu Glu Glu Glu Asp Gly
    50                  55                  60

Asp Lys Pro Lys Arg Arg Gly Pro Lys Lys Lys Met Thr Lys Ala
65                  70                  75                  80

Arg Leu Glu Arg Phe Arg Ala Arg Val Lys Ala Asn Ala Arg Glu
                85                  90                  95

Arg Thr Arg Met His Gly Leu Asn Asp Ala Leu Asp Asn Leu Arg Arg
            100                 105                 110

Val Met Pro Cys Tyr Ser Lys Thr Gln Lys Leu Ser Lys Ile Glu Thr
        115                 120                 125

Leu Arg Leu Ala Arg Asn Tyr Ile Trp Ala Leu Ser Glu Val Leu Glu
    130                 135                 140

Thr Gly Gln Thr Leu Glu Gly Lys Gly Phe Val Glu Met Leu Cys Lys
145                 150                 155                 160

Gly Leu Ser Gln Pro Thr Ser Asn Leu Val Ala Gly Cys Leu Gln Leu
                165                 170                 175
```

```
Gly Pro Gln Ser Thr Leu Leu Glu Lys His Glu Lys Ser Ser Ile
            180                 185                 190

Cys Asp Ser Thr Ile Ser Val His Ser Phe Asn Tyr Gln Ser Pro Gly
        195                 200                 205

Leu Pro Ser Pro Pro Tyr Gly His Met Glu Thr His Ser Leu His Leu
    210                 215                 220

Lys Pro Gln Pro Phe Lys Ser Leu Gly Asp Ser Phe Gly Ser His Pro
225                 230                 235                 240

Pro Asp Cys Ser Thr Pro Pro Tyr Glu Gly Pro Leu Thr Pro Pro Leu
                245                 250                 255

Ser Ile Ser Gly Asn Phe Ser Leu Lys Gln Asp Gly Ser Pro Asp Leu
            260                 265                 270

Glu Lys Ser Tyr Asn Phe Met Pro His Tyr Thr Ser Ala Ser Leu Ser
        275                 280                 285

Ser Gly His Val His Ser Thr Pro Phe Gln Thr Gly Thr Pro Arg Tyr
    290                 295                 300

Asp Val Pro Val Asp Leu Ser Tyr Asp Ser Tyr Ser His His Ser Ile
305                 310                 315                 320

Gly Thr Gln Leu Asn Thr Ile Phe Ser Asp
                325                 330

<210> SEQ ID NO 34
<211> LENGTH: 800
<212> TYPE: DNA
<213> ORGANISM: MOUSE

<400> SEQUENCE: 34
agggtagtag agtcactaat actacgtcct tgctgtgtag ttttctcagg ttttgattca      60
ttttaagcat gggccaccaa tctcatgtac cttttttagct ttctttccaa gtgtgtctcc   120
agttttctga ccccctcct gttttgcctg ctctaccctg ccttgtacct ttctaatcac    180
aagtcttttc agttcccta gttttcaccc atcaacttca gcagcccaca ccctctagtt    240 cctttcctggt ttaaacaaaa acaaacacgc agtggcaaag ctggacctgg tcagagaagc   300
cttgtgaagg aggtgtgtct ttaggctagg aaggggaggg gctaccctgt gggcaacatc   360
tcccgccctg gtcagcagcc aaaaccagca aacggcggc aagtcagaag ctccagtcag    420
atcacaggag ctgcccagag actgtggtac tgaaagaact actcgcggga gctgaccccg    480
ggaaagaggt actgaaaaga catagaaaac cagctgtggt ggaggcactg acatgaaggc    540
atcctggtag tgcatcagaa ctccaggaaa agtagaata agtaacagcc aaggtactca     600
gaccaggaac agtcactaga aggtagctac cagtttaaca tggacgactg aaagggtctt    660
ctgtttccca cgatctgcct ggtcaggtca gggtagaact gactgctctg atagttcttc    720
aggacacaga ttagagtttta atcttggaac tggacttcca gaggtgagcc tgtgaacggg    780
gtgtgggtac taaagtttct                                                  800

<210> SEQ ID NO 35
<211> LENGTH: 515
<212> TYPE: DNA
<213> ORGANISM: CHICKEN

<400> SEQUENCE: 35
tttttctgta tgcgtgtgaa gctgcatctg caatagatat gaaaacctgt caatccagtc      60
atttggattc aggagtagaa tcagacatcc agtgcagaag tggatcaggc tgtgttgtga    120
```

| | | |
|---|---|---|
| agtgcagcac agaaagaatg gagagcgctg ccaagagaag actggctgcc aacgccaggg | 180 | |
| agagaagacg gatgcaagga ctgaacacag cctttgatcg tttgaggaag gtggttccac | 240 | |
| agtggggtca agataagaag ctctccaaat atgagaccct tcagatggct ttgagttata | 300 | |
| tcatggctct aacacgaata cttgctgaag cagagagata cagtactgaa agagaatgga | 360 | |
| ttaaccttca ctgtgaacac tttcatccag agagctacca ccattatacg ggacaaaaag | 420 | |
| tggcaacaga cagtgatcct tatgcacagc gaatattcag ctatcaccct gaacactttc | 480 | |
| aaatagctaa ttagaactta ttacgagcta aaaaa | 515 | |

<210> SEQ ID NO 36
<211> LENGTH: 151
<212> TYPE: PRT
<213> ORGANISM: CHICKEN

<400> SEQUENCE: 36

```
Met Lys Thr Cys Gln Ser Ser His Leu Asp Ser Gly Val Glu Ser Asp
1               5                   10                  15

Ile Gln Cys Arg Ser Gly Ser Gly Cys Val Val Lys Cys Ser Thr Glu
            20                  25                  30

Arg Met Glu Ser Ala Ala Lys Arg Arg Leu Ala Ala Asn Ala Arg Glu
        35                  40                  45

Arg Arg Arg Met Gln Gly Leu Asn Thr Ala Phe Asp Arg Leu Arg Lys
    50                  55                  60

Val Val Pro Gln Trp Gly Gln Asp Lys Lys Leu Ser Lys Tyr Glu Thr
65                  70                  75                  80

Leu Gln Met Ala Leu Ser Tyr Ile Met Ala Leu Thr Arg Ile Leu Ala
                85                  90                  95

Glu Ala Glu Arg Tyr Ser Thr Glu Arg Glu Trp Ile Asn Leu His Cys
            100                 105                 110

Glu His Phe His Pro Glu Ser Tyr His His Tyr Thr Gly Gln Lys Val
        115                 120                 125

Ala Thr Asp Ser Asp Pro Tyr Ala Gln Arg Ile Phe Ser Tyr His Pro
    130                 135                 140

Glu His Phe Gln Ile Ala Asn
145                 150
```

<210> SEQ ID NO 37
<211> LENGTH: 1412
<212> TYPE: DNA
<213> ORGANISM: MOUSE

<400> SEQUENCE: 37

| | | |
|---|---|---|
| cgtgctcggt tccgggctgc ggggacattc ccggacacac accggagcag cagctgcgcc | 60 | |
| gcgacacatc tggagccgcg taggatgttc gtcaaatctg agactctgga gttgaaggag | 120 | |
| gaagaggagg tactgatgct gctgggctcg gcttccccgg cctcggcgac cctgaccccg | 180 | |
| atgtcctcca gcgcggacga ggaggaggac gaggagctgc gccggccggg ctccgcgcgt | 240 | |
| gggcagcgtg gagcggaagc cgggcagggg gtgcagggca gtccggcgtc gggtgccggg | 300 | |
| ggttgccggc cagggcggct gctgggcctg atgcacgagt gcaagcgtcg cccgtcgcgc | 360 | |
| tcacgggccg tctcccgagg tgccaagacg cggagacgtg cagcgcat caagaagacc | 420 | |
| cgcaggctca aggccaacaa ccgcgagcgc aaccgcatgc acaacctaaa cgccgcgctg | 480 | |
| gacgcgctgc gcgaggtgct gcccaccttc cccgaggatg ccaagctcac gaagatcgag | 540 | |
| acgctgcgct tcgcccacaa ttacatctgg gcgctcaccg agactctgcg cctggcggac | 600 | |

-continued

```
cactgcgccg cgccggtgg cctccagggg gcgctcttca cggaggcggt gctcctgagc      660
ccgggagctg cgctcggcgc cagcggggac agcccttctc caccttcctc ctggagctgc      720
accaacagcc cggcgtcatc ctccaactcc acgtccccat acagctgcac tttatcgccc      780
gctagccccg ggtcagacgt ggactactgg cagcccccac ctccggagaa gcatcgttat      840
gcgcctcacc tgccctcgc cagggactgt atctagagct gcgggtctcc ctctctcgtc       900
ctctacccgg ccctcttccc atccttctcc cgcccctcac cctccacgcc ccggactcca      960
cttcacagag cagaggtggc ccttgcaatc ccctcggcgg ctggtgcatt cgggggtgga     1020
gaccagctct ggtttattga agatgtgagg atttatggtc aaagaggact atggcgtgtg     1080
ggagtggggg ctggcgtggg gaacctcgta agactgtaaa agacactgag aaaaagtacc     1140
ataactaacg agtgtgcaga gcagactgac gctcctcccc tctctcagag ctgctggagg     1200
agaactccgg gcaggcagtt cgtgtgaatc tctcagaggg aatgcaactg gtccctgtga     1260
tcttttcacc ttcgtttcta catagagatg ttaatgtcag tcgaaagaaa tgtattttag     1320
catctgaatg aatttactgg taataatatt atccacacat ttgcaatggc tggcatctgc     1380
tctattccca ttgctgtctg caggctgtgg ga                                   1412
```

<210> SEQ ID NO 38
<211> LENGTH: 263
<212> TYPE: PRT
<213> ORGANISM: MOUSE

<400> SEQUENCE: 38

```
Met Phe Val Lys Ser Glu Thr Leu Glu Leu Lys Glu Glu Glu Glu Val
1               5                   10                  15

Leu Met Leu Leu Gly Ser Ala Ser Pro Ala Ser Ala Thr Leu Thr Pro
                20                  25                  30

Met Ser Ser Ser Ala Asp Glu Glu Asp Glu Glu Leu Arg Arg Pro
            35                  40                  45

Gly Ser Ala Arg Gly Gln Arg Gly Ala Glu Ala Gly Gln Gly Val Gln
        50                  55                  60

Gly Ser Pro Ala Ser Gly Ala Gly Cys Arg Pro Gly Arg Leu Leu
65                  70                  75                  80

Gly Leu Met His Glu Cys Lys Arg Arg Pro Ser Arg Ser Arg Ala Val
                85                  90                  95

Ser Arg Gly Ala Lys Thr Ala Glu Thr Val Gln Arg Ile Lys Lys Thr
            100                 105                 110

Arg Arg Leu Lys Ala Asn Asn Arg Glu Arg Asn Arg Met His Asn Leu
        115                 120                 125

Asn Ala Ala Leu Asp Ala Leu Arg Glu Val Leu Pro Thr Phe Pro Glu
    130                 135                 140

Asp Ala Lys Leu Thr Lys Ile Glu Thr Leu Arg Phe Ala His Asn Tyr
145                 150                 155                 160

Ile Trp Ala Leu Thr Glu Thr Leu Arg Leu Ala Asp His Cys Ala Gly
                165                 170                 175

Ala Gly Gly Leu Gln Gly Ala Leu Phe Thr Glu Ala Val Leu Leu Ser
            180                 185                 190

Pro Gly Ala Ala Leu Gly Ala Ser Gly Asp Ser Pro Ser Pro Pro Ser
        195                 200                 205

Ser Trp Ser Cys Thr Asn Ser Pro Ala Ser Ser Asn Ser Thr Ser
    210                 215                 220
```

```
Pro Tyr Ser Cys Thr Leu Ser Pro Ala Ser Pro Gly Ser Asp Val Asp
225                 230                 235                 240

Tyr Trp Gln Pro Pro Pro Glu Lys His Arg Tyr Ala Pro His Leu
            245                 250                 255

Pro Leu Ala Arg Asp Cys Ile
            260
```

<210> SEQ ID NO 39  
<211> LENGTH: 938  
<212> TYPE: DNA  
<213> ORGANISM: ZEBRA FISH

<400> SEQUENCE: 39

```
cttatagggc tcgagcggcc gcccgggcag gtcaggtgta agaagagaaa tcttcccagg     60
caaaatatcc gtccctgtat ccatagccac aaactttcct cccaaaagca caaaccaaca   120
gaatggatgg aatgagcacg gatcaagag aggtggttga actcgacgtc cagcattcga    180
gcttggggcg gggggagcag agcaagtacc caccagcctt ggcactcatg ccagcagtg    240
acccacgcgc ctggctggct cccgtgcagg ctggcacctg cgcggcacac gccgaatacc   300
tgctgcactc gcccggctcg agcgcggaag gcgtgtcctc tgcctccaac ttcaggaaga   360
gcagcaagag tcctgtcaaa gtacgcgagc tctgccggct taaggagct gtggggcag    420
atgagggcag acagcgggcc ccatccagca aatccaccaa cgtcgtgcag aaacagaggc   480
gaatggctgc caatgcccgg gagaggcgaa gaatgcacgg attgaaccac gcgttcgacg   540
agctgcgcag tgtcatccca gcctttgaca cgacaagaa actctccaag tacgaaaccc    600
tgcagatggc ccagatctac atcaacgccc tgtccgactt actacagggc cccggtgcta   660
aagccgaccc gccaaactgc gacctgctgc atgccaacgt gttagaaacg gaccgatctc   720
ccagaggatc accgggcgtc tgtcggagag gcacgggcgt gggttacccg taccagtacg   780
aggacggaac attcaactct ttcatggagc aagacctcca gtcgccctct ggaacgagca   840
agtctggttc ggaggccagt aaagactcgc tcggtcgaa ccggagtgat ggagaagttc    900
tcgcctcact gaagtgcgag tgagacctgc ccgggcgg                           938
```

<210> SEQ ID NO 40  
<211> LENGTH: 266  
<212> TYPE: PRT  
<213> ORGANISM: ZEBRA FISH

<400> SEQUENCE: 40

```
Met Asp Gly Met Ser Thr Asp Thr Arg Glu Val Val Glu Leu Asp Val
1               5                   10                  15

Gln His Ser Ser Leu Gly Arg Gly Glu Gln Ser Lys Tyr Pro Pro Ala
            20                  25                  30

Leu Ala Leu Met Ala Ser Ser Asp Pro Arg Ala Trp Leu Ala Pro Val
        35                  40                  45

Gln Ala Gly Thr Cys Ala Ala His Ala Glu Tyr Leu Leu His Ser Pro
    50                  55                  60

Gly Ser Ser Ala Glu Gly Val Ser Ser Ala Ser Asn Phe Arg Lys Ser
65                  70                  75                  80

Ser Lys Ser Pro Val Lys Val Arg Glu Leu Cys Arg Leu Lys Gly Ala
                85                  90                  95

Val Gly Ala Asp Glu Gly Arg Gln Arg Ala Pro Ser Ser Lys Ser Thr
            100                 105                 110

Asn Val Val Gln Lys Gln Arg Arg Met Ala Ala Asn Ala Arg Glu Arg
```

```
                    115                 120                 125
Arg Arg Met His Gly Leu Asn His Ala Phe Asp Glu Leu Arg Ser Val
    130                 135                 140

Ile Pro Ala Phe Asp Asn Asp Lys Lys Leu Ser Lys Tyr Glu Thr Leu
145                 150                 155                 160

Gln Met Ala Gln Ile Tyr Ile Asn Ala Leu Ser Asp Leu Leu Gln Gly
                165                 170                 175

Pro Gly Ala Lys Ala Asp Pro Pro Asn Cys Asp Leu Leu His Ala Asn
            180                 185                 190

Val Leu Glu Thr Asp Arg Ser Pro Arg Gly Ser Pro Gly Val Cys Arg
        195                 200                 205

Arg Gly Thr Gly Val Gly Tyr Pro Tyr Gln Tyr Glu Asp Gly Thr Phe
    210                 215                 220

Asn Ser Phe Met Glu Gln Asp Leu Gln Ser Pro Ser Gly Thr Ser Lys
225                 230                 235                 240

Ser Gly Ser Glu Ala Ser Lys Asp Ser Pro Arg Ser Asn Arg Ser Asp
                245                 250                 255

Gly Glu Val Leu Ala Ser Leu Lys Cys Glu
            260                 265

<210> SEQ ID NO 41
<211> LENGTH: 948
<212> TYPE: DNA
<213> ORGANISM: FROG

<400> SEQUENCE: 41
atgtcagaga tggtcaatgt gcatgggtgg atggaggaag cccttagttc ccaggatgag      60
atgaaggaga ggaatcagtc tgcctatgat atcatttcag gtctatgcca tgaggaaagg     120
ggcagcattg atggagaaga ggatgatgaa gaagaagagg atggagagaa accaaaaaag     180
agggaccca aaaaaaagaa gatgaccaag gctagagtgg agaggttccg tgtccgtaga      240
gtaaaagcca atgccaggga gcgttcaaga atgcatggac ttaatgatgc cctggaaaat     300
ttgagaaggg ttatgccttg ctattccaaa acacaaaagt tgtctaaaat tgagactctt     360
agactggcca gaaactatat atgggcatta tctgatattc tagaacaagg tcaaaatgca     420
gagggaaagg gctttctgga aatactctgc aaaggtcttt ctcagccaac aagcaactta     480
gtagctggct gcttgcaact tggacctcag gccatgttct tggataaaca cgaagaaaag     540
tctcatatat gtgattcctc tcttactggt catacttata attaccagtc ccaggacta     600
cccagtcctc cttatggtaa cattgatgtt caccacttgc acttgaaacc ctcttctttc     660
aaaccagtaa tggatccttc tgtggtaacc catacactta actgtaccac tccaccatat     720
gaaggagctc taacacctcc actcagcatc ggtggtaatt tttctttgaa gcaagatagt     780
tcacccgata tggataaatc atatgcattc aggtccccct atccagctct tgggcttggt     840
ggatctcatg gacatgcgtc acactttcat accagtgttc caaggtatga actacccata     900
gacatggctt acgagcctta cccacaccat gctatattca ctgaataa                  948

<210> SEQ ID NO 42
<211> LENGTH: 315
<212> TYPE: PRT
<213> ORGANISM: FROG

<400> SEQUENCE: 42

Met Ser Glu Met Val Asn Val His Gly Trp Met Glu Glu Ala Leu Ser
1               5                   10                  15
```

```
Ser Gln Asp Glu Met Lys Glu Arg Asn Gln Ser Ala Tyr Asp Ile Ile
         20                  25                  30

Ser Gly Leu Cys His Glu Arg Gly Ser Ile Asp Gly Glu Glu Asp
         35                  40                  45

Asp Glu Glu Glu Asp Gly Glu Lys Pro Lys Arg Gly Pro Lys
    50                  55                  60

Lys Lys Lys Met Thr Lys Ala Arg Val Glu Arg Phe Arg Val Arg Arg
65                  70                  75                  80

Val Lys Ala Asn Ala Arg Glu Arg Ser Arg Met His Gly Leu Asn Asp
                85                  90                  95

Ala Leu Glu Asn Leu Arg Arg Val Met Pro Cys Tyr Ser Lys Thr Gln
            100                 105                 110

Lys Leu Ser Lys Ile Glu Thr Leu Arg Leu Ala Arg Asn Tyr Ile Trp
            115                 120                 125

Ala Leu Ser Asp Ile Leu Glu Gln Gly Gln Asn Ala Glu Gly Lys Gly
        130                 135                 140

Phe Leu Glu Ile Leu Cys Lys Gly Leu Ser Gln Pro Thr Ser Asn Leu
145                 150                 155                 160

Val Ala Gly Cys Leu Gln Leu Gly Pro Gln Ala Met Phe Leu Asp Lys
                165                 170                 175

His Glu Glu Lys Ser His Ile Cys Asp Ser Ser Leu Thr Gly His Thr
            180                 185                 190

Tyr Asn Tyr Gln Ser Pro Gly Leu Pro Ser Pro Tyr Gly Asn Ile
            195                 200                 205

Asp Val His His Leu His Leu Lys Pro Ser Ser Phe Lys Pro Val Met
    210                 215                 220

Asp Pro Ser Val Val Thr His Thr Leu Asn Cys Thr Thr Pro Pro Tyr
225                 230                 235                 240

Glu Gly Ala Leu Thr Pro Pro Leu Ser Ile Gly Gly Asn Phe Ser Leu
                245                 250                 255

Lys Gln Asp Ser Ser Pro Asp Met Asp Lys Ser Tyr Ala Phe Arg Ser
            260                 265                 270

Pro Tyr Pro Ala Leu Gly Leu Gly Gly Ser His Gly His Ala Ser His
        275                 280                 285

Phe His Thr Ser Val Pro Arg Tyr Glu Leu Pro Ile Asp Met Ala Tyr
    290                 295                 300

Glu Pro Tyr Pro His His Ala Ile Phe Thr Glu
305                 310                 315

<210> SEQ ID NO 43
<211> LENGTH: 1550
<212> TYPE: DNA
<213> ORGANISM: MOUSE

<400> SEQUENCE: 43
tttaaatact gtgctggcat ttttttcag gtaaattaag gttaaagaac catgttaaca      60
ctaccgtttg acgagtctgt cgtaatgccc gaatcccaga tgtgcagaaa gtttgctaga     120
caatgtgagg accagaaaca aattaagaaa ccagagagct tccaaaaca agttgtcctt      180 cgaggaaaga gcattaaaag ggcccctgga agaaaccg agaaagaaga ggaggaagaa       240
gacagagagg aagaagatga gaatggcttg tccagaagga gggggctcag gaaaaaaaag   300
accaccaaac tacgactgga aagggtcaag ttcaggagac aggaagctaa tgcgcgcgag   360
aggaaccgga tgcacggcct caatgatgct ctggacaatt tgcgaaaagt ggtcccctgt   420
```

```
tactctaaaa cccaaaaact gtccaaaata gaaactttac gactggccaa aaattacatc    480
tgggcacttt ctgaaattct gaggattggc aagagaccgg atctgctcac gttcgtccaa    540
aacttatgca aaggtctttc ccagccaact acaaacttgg tggcaggctg cttacagctc    600
aacgccagaa gtttcctgat gggtcagggt ggggaggctg cccaccacac aaggtcaccc    660
tactccacat tctacccacc ctaccacagc cctgagctgg ccactccccc agggcatggg    720
actcttgata attccaagtc catgaaaccc tacaattact gcagtgcata tgaatccttc    780
tatgaaagta cctcccctga gtgtgccagc cctcagtttg aaggtccctt aagtcctccc    840
ccaattaact ataatgggat attttccctg aagcaagaag aaaccttgga ctatggcaaa    900
aattacaatt atggcatgca ttactgtgca gtgccaccca gggtcccct tgggcagggt    960 gccatgttca ggttgcccac cgacagccac ttcccttacg acttacatct gcgcagccaa   1020
tctctcacta tgcaagatga attaaatgca gtttttcata ttaatgagg aaaattaaaa   1080 taaacagtgg tcattcacct cccactctaa ttaaggcaaa gcagatgctt gtgggctgag   1140
taattggcac aactctatct aaggtgttta ctagtttctg aagtgtgttt caaagattgt   1200
gaccattttc tatgtcataa taaatccctt ttcgtatgag aacttccttt ccttccctct   1260
tgtctgtatc acactgtgat tctctctctc tctctctctc tctctctctc tctctctctc   1320
tcttactggc agaatatttc tttcttgttt tagtttcttt caaattcact taatttgttt   1380
gaacaaggtg tctaagatgt tgctgaataa agacatgcac acagcatact tcaatgtcta   1440
tttcagttgt acagttatga tgaaaatgca tgttataaaa atcagatgag taaaatgtgt   1500
ttataattac taggattcat atatgtatct ctgaaatttt agttttttaaa              1550
```

<210> SEQ ID NO 44
<211> LENGTH: 337
<212> TYPE: PRT
<213> ORGANISM: MOUSE

<400> SEQUENCE: 44

```
Met Leu Thr Leu Pro Phe Asp Glu Ser Val Val Met Pro Glu Ser Gln
1               5                  10                  15

Met Cys Arg Lys Phe Ala Arg Gln Cys Glu Asp Gln Lys Gln Ile Lys
            20                  25                  30

Lys Pro Glu Ser Phe Pro Lys Gln Val Val Leu Arg Gly Lys Ser Ile
        35                  40                  45

Lys Arg Ala Pro Gly Glu Glu Thr Glu Lys Glu Glu Glu Glu Glu Asp
    50                  55                  60

Arg Glu Glu Glu Asp Glu Asn Gly Leu Ser Arg Arg Gly Leu Arg
65                  70                  75                  80

Lys Lys Lys Thr Thr Lys Leu Arg Leu Glu Arg Val Lys Phe Arg Arg
                85                  90                  95

Gln Glu Ala Asn Ala Arg Glu Arg Asn Arg Met His Gly Leu Asn Asp
            100                 105                 110

Ala Leu Asp Asn Leu Arg Lys Val Val Pro Cys Tyr Ser Lys Thr Gln
        115                 120                 125

Lys Leu Ser Lys Ile Glu Thr Leu Arg Leu Ala Lys Asn Tyr Ile Trp
    130                 135                 140

Ala Leu Ser Glu Ile Leu Arg Ile Gly Lys Arg Pro Asp Leu Leu Thr
145                 150                 155                 160

Phe Val Gln Asn Leu Cys Lys Gly Leu Ser Gln Pro Thr Thr Asn Leu
                165                 170                 175
```

```
Val Ala Gly Cys Leu Gln Leu Asn Ala Arg Ser Phe Leu Met Gly Gln
            180                 185                 190

Gly Gly Glu Ala Ala His His Thr Arg Ser Pro Tyr Ser Thr Phe Tyr
        195                 200                 205

Pro Pro Tyr His Ser Pro Glu Leu Ala Thr Pro Pro Gly His Gly Thr
    210                 215                 220

Leu Asp Asn Ser Lys Ser Met Lys Pro Tyr Asn Tyr Cys Ser Ala Tyr
225                 230                 235                 240

Glu Ser Phe Tyr Glu Ser Thr Ser Pro Glu Cys Ala Ser Pro Gln Phe
                245                 250                 255

Glu Gly Pro Leu Ser Pro Pro Ile Asn Tyr Asn Gly Ile Phe Ser
            260                 265                 270

Leu Lys Gln Glu Glu Thr Leu Asp Tyr Gly Lys Asn Tyr Asn Tyr Gly
            275                 280                 285

Met His Tyr Cys Ala Val Pro Pro Arg Gly Pro Leu Gly Gln Gly Ala
        290                 295                 300

Met Phe Arg Leu Pro Thr Asp Ser His Phe Pro Tyr Asp Leu His Leu
305                 310                 315                 320

Arg Ser Gln Ser Leu Thr Met Gln Asp Glu Leu Asn Ala Val Phe His
                325                 330                 335

Asn

<210> SEQ ID NO 45
<211> LENGTH: 1393
<212> TYPE: DNA
<213> ORGANISM: MOUSE

<400> SEQUENCE: 45
```

| | | | | | |
|---|---|---|---|---|---|
| aagcttcgtt | gcacgcgacc | tggtgtgcga | tctccgagtg | agaggggag | ggtcagagga | 60 |
| ggaaggaaaa | aaaatcagac | cttgcagaag | agactaggaa | ggttttttgtt | gttgttgttc | 120 |
| ggggcttatc | cccttcgttg | aactgggttg | ccagcacctc | ctctaacacg | gcacctccga | 180 |
| gccattgcag | tgcgatgtcc | cgcctgctgc | atgcagaaga | gtgggctgag | gtaaaagagt | 240 |
| tgggggacca | ccatcgccat | cccagccgc | accacgtccc | gccgctgacg | ccacagccac | 300 |
| ctgctaccct | gcaggcgaga | gaccttcccg | tctaccggc | agaactgtcc | ctcctggata | 360 |
| gcaccgaccc | acgcgcctgg | ctgactccca | cttttgcaggg | cctctgcacg | gcacgcgccg | 420 |
| cccagtatct | gctgcattct | cccgagctgg | gtgcctccga | ggccgcggcg | cccgggacg | 480 |
| aggctgacag | ccagggtgag | ctggtaagga | gaagcggctg | tggcggcctc | agcaagagcc | 540 |
| ccgggcccgt | caaagtacgg | aacagctgt | gcaagctgaa | gggtgggtt | gtagtggacg | 600 |
| agcttggctg | cagccgccag | cgagcccctt | ccagcaaaca | ggtgaatggg | gtacagaagc | 660 |
| aaaggaggct | ggcagcaaac | gcaagggaac | ggcgcaggat | gcacgggctg | aaccacgcct | 720 |
| tcgaccagct | gcgcaacgtt | atcccgtcct | tcaacaacga | caagaagctg | tccaaatatg | 780 |
| agaccctaca | gatggcccag | atctacatca | acgtctgtc | ggagttgctg | cagactccca | 840 |
| atgtcggaga | gcaaccgccg | ccgcccacag | cttcctgcaa | aaatgaccac | catcaccttc | 900 |
| gcaccgcctc | ctcctatgaa | ggaggtgcgg | gcgcctctgc | ggtagctggg | gctcagccag | 960 |
| ccccgggagg | gggcccgaga | cctacccgc | ccgggccttg | ccggactcgc | ttctcaggcc | 1020 |
| cagcttcctc | tgggggttac | tcggtgcagc | tggacgcttt | gcacttccca | gccttcgagg | 1080 |
| acagggccct | aacagcgatg | atggcacaga | aggacctgtc | gccttcgctg | cccgggggca | 1140 |

```
tcctgcagcc tgtacaggag gacaacagca aaacatctcc cagatcccac agaagtgacg    1200
gagagttttc ccccactct cattacagtg actctgatga ggccagttag gaaggcaaca    1260
gctccctgaa aactgagaca accaaatgcc cttcctagcg cgcgggaagc cccgtgacaa    1320
atatccctgc accctttaat ttttggtctg tggtgatcgt tgttagcaac gacttgactt    1380
cggacggctg cag                                                       1393
```

<210> SEQ ID NO 46
<211> LENGTH: 351
<212> TYPE: PRT
<213> ORGANISM: MOUSE

<400> SEQUENCE: 46

```
Met Ser Arg Leu Leu His Ala Glu Glu Trp Ala Glu Val Lys Glu Leu
1               5                   10                  15

Gly Asp His His Arg His Pro Gln Pro His Val Pro Pro Leu Thr
            20                  25                  30

Pro Gln Pro Pro Ala Thr Leu Gln Ala Arg Asp Leu Pro Val Tyr Pro
        35                  40                  45

Ala Glu Leu Ser Leu Leu Asp Ser Thr Asp Pro Arg Ala Trp Leu Thr
    50                  55                  60

Pro Thr Leu Gln Gly Leu Cys Thr Ala Arg Ala Gln Tyr Leu Leu
65                  70                  75                  80

His Ser Pro Glu Leu Gly Ala Ser Glu Ala Ala Pro Arg Asp Glu
                85                  90                  95

Ala Asp Ser Gln Gly Glu Leu Val Arg Arg Ser Gly Cys Gly Gly Leu
            100                 105                 110

Ser Lys Ser Pro Gly Pro Val Lys Val Arg Glu Gln Leu Cys Lys Leu
        115                 120                 125

Lys Gly Gly Val Val Val Asp Glu Leu Gly Cys Ser Arg Gln Arg Ala
    130                 135                 140

Pro Ser Ser Lys Gln Val Asn Gly Val Gln Lys Gln Arg Arg Leu Ala
145                 150                 155                 160

Ala Asn Ala Arg Glu Arg Arg Met His Gly Leu Asn His Ala Phe
                165                 170                 175

Asp Gln Leu Arg Asn Val Ile Pro Ser Phe Asn Asn Asp Lys Lys Leu
            180                 185                 190

Ser Lys Tyr Glu Thr Leu Gln Met Ala Gln Ile Tyr Ile Asn Ala Leu
        195                 200                 205

Ser Glu Leu Leu Gln Thr Pro Asn Val Gly Glu Gln Pro Pro Pro
    210                 215                 220

Thr Ala Ser Cys Lys Asn Asp His His His Leu Arg Thr Ala Ser Ser
225                 230                 235                 240

Tyr Glu Gly Gly Ala Gly Ala Ser Ala Val Ala Gly Ala Gln Pro Ala
                245                 250                 255

Pro Gly Gly Gly Pro Arg Pro Thr Pro Gly Pro Cys Arg Thr Arg
            260                 265                 270

Phe Ser Gly Pro Ala Ser Ser Gly Gly Tyr Ser Val Gln Leu Asp Ala
        275                 280                 285

Leu His Phe Pro Ala Phe Glu Asp Arg Ala Leu Thr Ala Met Met Ala
    290                 295                 300

Gln Lys Asp Leu Ser Pro Ser Leu Pro Gly Gly Ile Leu Gln Pro Val
305                 310                 315                 320

Gln Glu Asp Asn Ser Lys Thr Ser Pro Arg Ser His Arg Ser Asp Gly
```

325                 330                 335
Glu Phe Ser Pro His Ser His Tyr Ser Asp Ser Asp Glu Ala Ser
                340                 345                 350

<210> SEQ ID NO 47
<211> LENGTH: 993
<212> TYPE: DNA
<213> ORGANISM: MOUSE

<400> SEQUENCE: 47

| | | | | | |
|---|---|---|---|---|---|
| atggcaaaaa | tgtatatgaa | atccaaggac | atggtggagc | tggtcaacac | acaatcctgg | 60 |
| atggacaaag | gtctgagctc | tcaaaatgag | atgaaggagc | aagagagaag | accgggctct | 120 |
| tatggaatgc | tcggaacctt | aactgaagag | catgacagta | ttgaggagga | tgaagaagag | 180 |
| gaagaagatg | gagataaacc | taaaagaaga | ggtcccaaga | aaaagaagat | gactaaagct | 240 |
| cgccttgaaa | gattcagggc | tcgaagagtc | aaggccaatg | ctagagaacg | acccggatg | 300 |
| catggcctga | atgatgcctt | ggataatctt | aggagagtca | tgccatgtta | ctctaaaact | 360 |
| caaaagcttt | ccaagataga | gactcttcga | ctggcaagga | actacatctg | gccttgtct | 420 |
| gaagtcctgg | agactggtca | gacacttgaa | gggaagggat | ttgtagagat | gctatgtaaa | 480 |
| ggtctctctc | aacccacaag | caacctggtt | gctggatgcc | tccaactggg | gcctcaatct | 540 |
| accctcctgg | agaagcatga | ggaaaaatct | tcaatttgtg | actctactat | ctctgtccac | 600 |
| agcttcaact | atcagtctcc | agggctcccc | agccctcctt | atggccatat | ggaaacacat | 660 |
| tctctccatc | tcaagcctca | accatttaag | agtttgggtg | actcttttgg | gagccatcca | 720 |
| cctgactgca | gtaccccccc | ttatgagggt | ccactcacac | caccccctgag | cattagtggc | 780 |
| aacttctcct | aaagcaagaa | cggctcccct | gatttggaaa | aatcctacaa | tttcatgcca | 840 |
| cattatacct | ctgcaagtct | aagttcaggg | catgtgcatt | caactcccctt | tcagactggc | 900 |
| actccccgct | atgatgttcc | tgtagacctg | agctatgatt | cctactccca | ccatagcatt | 960 |
| ggaactcagc | tcaatacgat | cttctctgat | tag | | | 993 |

<210> SEQ ID NO 48
<211> LENGTH: 330
<212> TYPE: PRT
<213> ORGANISM: Mus musculus

<400> SEQUENCE: 48

Met Ala Lys Met Tyr Met Lys Ser Lys Asp Met Val Glu Leu Val Asn
1               5                   10                  15

Thr Gln Ser Trp Met Asp Lys Gly Leu Ser Ser Gln Asn Glu Met Lys
            20                  25                  30

Glu Gln Glu Arg Arg Pro Gly Ser Tyr Gly Met Leu Gly Thr Leu Thr
        35                  40                  45

Glu Glu His Asp Ser Ile Glu Glu Asp Glu Glu Glu Glu Asp Gly
    50                  55                  60

Asp Lys Pro Lys Arg Arg Gly Pro Lys Lys Lys Met Thr Lys Ala
65                  70                  75                  80

Arg Leu Glu Arg Phe Arg Ala Arg Val Lys Ala Asn Ala Arg Glu
                85                  90                  95

Arg Thr Arg Met His Gly Leu Asn Asp Ala Leu Asp Asn Leu Arg Arg
            100                 105                 110

Val Met Pro Cys Tyr Ser Lys Thr Gln Lys Leu Ser Lys Ile Glu Thr
        115                 120                 125

| | | | | | | | | | | | |
|---|---|---|---|---|---|---|---|---|---|---|---|
|Leu|Arg|Leu|Ala|Arg|Asn|Tyr|Ile|Trp|Ala|Leu|Ser|Glu|Val|Leu|Glu|
| |130| | | |135| | | |140| | | | | | |

Thr Gly Gln Thr Leu Glu Gly Lys Gly Phe Val Glu Met Leu Cys Lys
145                 150                 155                 160

Gly Leu Ser Gln Pro Thr Ser Asn Leu Val Ala Gly Cys Leu Gln Leu
                165                 170                 175

Gly Pro Gln Ser Thr Leu Leu Glu Lys His Glu Glu Lys Ser Ser Ile
            180                 185                 190

Cys Asp Ser Thr Ile Ser Val His Ser Phe Asn Tyr Gln Ser Pro Gly
        195                 200                 205

Leu Pro Ser Pro Pro Tyr Gly His Met Glu Thr His Ser Leu His Leu
    210                 215                 220

Lys Pro Gln Pro Phe Lys Ser Leu Gly Asp Ser Phe Gly Ser His Pro
225                 230                 235                 240

Pro Asp Cys Ser Thr Pro Pro Tyr Glu Gly Pro Leu Thr Pro Pro Leu
                245                 250                 255

Ser Ile Ser Gly Asn Phe Ser Leu Lys Gln Asp Gly Ser Pro Asp Leu
                260                 265                 270

Glu Lys Ser Tyr Asn Phe Met Pro His Tyr Thr Ser Ala Ser Leu Ser
            275                 280                 285

Ser Gly His Val His Ser Thr Pro Phe Gln Thr Gly Thr Pro Arg Tyr
    290                 295                 300

Asp Val Pro Val Asp Leu Ser Tyr Asp Ser Tyr Ser His His Ser Ile
305                 310                 315                 320

Gly Thr Gln Leu Asn Thr Ile Phe Ser Asp
                325                 330

<210> SEQ ID NO 49
<211> LENGTH: 2264
<212> TYPE: DNA
<213> ORGANISM: FROG

<400> SEQUENCE: 49

```
gacagtcagt agatgctcct ttcccaaagt gtatcttgca gtagccttac actaatactg      60
cctgtcttgt agctggagag ctttgtatcg atgctaagag cactgggtat ctacaaagag     120
gatcactgca tatgaatgga ataaggagtg ctgctgctac ccaggctggg gtttgttccg     180
agcccttcaa aaccttttgg ccatagaatc actgtgttga catgaagtca gattcaccag     240
tgcatgggga gtcccatact gaatgccagt caccatgccc actaagttgc atgccagcca     300
ggctggaagg ctctaccaag agacgtctgg ctgccaatgc agggaaagaa aggagaatgc     360
aaggactgaa taccgccttc gatagtctga ggaaagttgt accgcaatgg ggtgaggaca     420
aaaaacttc caagtatgag actctacaga tggcactgag ctacatcatg gcactaagca     480
ggatcctcac ggaagcagaa agatacagca gaactgatcc aggggaatgg actaaaatgc     540
actttgatca cattcaggaa gaacagtgcc tcagttatat gggagtgaga tgcccaagag     600
actgtgatcg ctacctgccc cagactttt ctcactagga taggagatgt gagcaacagt     660
cagcaggcaa ggtactatag acctgaagat agcagtgtat tcctacacac agcagccaat     720
aatacaggga catttgcatc atgggttatt tgtcatgtca ttctgcccaa tgcactgctt     780
atttcattaa gcacccaaag tcccaggact gggaatatat gtagggcacc ccacgtgatg     840
cagcccaaag tatgtgctgc tgcaactgat agtgagctgt gggacactgg aaaagcaaag     900
tgcgctggta ttttgtaaat gaaaatgtca ttatgggtgg catataataa ttacttacac     960
```

```
acagcacagt tatataattt cattgctgtt agaaagcccc tttgtctctt accccccatc    1020
ctgctttcca tgttactaat gcactggtat cagtgaacat gtagaaggta gtatttatac    1080
attagaaaaa cactgaatgt gcataaacat cattttctc aatatacatt tactatatag     1140
ttcagttggt aagtgctggt aaacagcagc tgcccacaag ttctgtgcac tgctcatagg    1200
ggaaaggaaa cattttgcc acttgctaga gaatgctaat tgcattgtac tctgtaatat     1260
tgtcttgtgt ccagggtaag aaaggtctaa attaaaatca ataggaggca taatttacac    1320 atttcctta agctgtaatt ttctggcttt tgtctgcatt ttaatagtgg aaaattacaa     1380
cgtgtataaa attcctactg gtctcattct acttgtttct gtaagacaaa ccctggtgtg    1440
tttttaagga aaccttaagt aattcttttg aatagtatac atttcttgaa tgttttttttt   1500 tttttttttca atgggcatga gttgtttatt tgtaaacaca gctccaaagt taacagattg   1560
cttgtatctt tcaggtatgc aaatggtatt ttagtctatt ctgggacttt gaaatagaaa    1620
gcaatatgca acccttttaga attagaaaat gtagtacaac ggaacaaatg gtgaatggct   1680
tggcagagta ctgtacatac tgacctatgg agcatagttg gctaaatcag tctgcagttc    1740
acttttactg gtgtgttgca gttagaataa taaaatcgga tgttgctaag gttgttacag    1800
tatttctttg ccccagttaa tgcatgacct cccatcttac agagtttcta acacgttgcc    1860
aatgtattgt tatctttcga aaaatgtgga tggaacgtga tcaggtgcaa attcatgcga    1920
tttacctgtg cataattcct ataaaacaga acaatgtgt agttatagga ggattcacta    1980
cacggatgaa agatcttatt tacaacaggt taggcacaaa aagtgcagga ccatgaaaaa    2040
ttgtggccct ttagatttac taaattctgg cacccagcca ttgtgatgct gcacctgcac    2100
tcagcaccat attataatcc agcacaaggc agtaagtata aggctcccat actcttctca    2160
ctgataagct tgctagagat gttcccaagg aagcccatgt gctgcccatc ttctgcccctt   2220 cctctaggca gcactgcctc acatgcggaa tgaaggccca agcg                    2264
```

<210> SEQ ID NO 50
<211> LENGTH: 138
<212> TYPE: PRT
<213> ORGANISM: FROG

<400> SEQUENCE: 50

```
Met Lys Ser Asp Ser Pro Val His Gly Glu Ser His Thr Glu Cys Gln
1               5                   10                  15

Ser Pro Cys Pro Leu Ser Cys Met Pro Ala Arg Leu Glu Gly Ser Thr
            20                  25                  30

Lys Arg Arg Leu Ala Ala Asn Ala Arg Glu Arg Arg Met Gln Gly
        35                  40                  45

Leu Asn Thr Ala Phe Asp Ser Leu Arg Lys Val Val Pro Gln Trp Gly
    50                  55                  60

Glu Asp Lys Lys Leu Ser Lys Tyr Glu Thr Leu Gln Met Ala Leu Ser
65                  70                  75                  80

Tyr Ile Met Ala Leu Ser Arg Ile Leu Thr Glu Ala Glu Arg Tyr Ser
                85                  90                  95

Arg Thr Asp Pro Gly Glu Trp Thr Lys Met His Phe Asp His Ile Gln
            100                 105                 110

Glu Glu Gln Cys Leu Ser Tyr Met Gly Val Arg Cys Pro Arg Asp Cys
        115                 120                 125

Asp Arg Tyr Leu Pro Gln Thr Phe Ser His
    130                 135
```

<210> SEQ ID NO 51
<211> LENGTH: 2123
<212> TYPE: DNA
<213> ORGANISM: FROG

<400> SEQUENCE: 51

| | | | | | |
|---|---|---|---|---|---|
| gacagtcagt | agatgctcct | tgcctgaagt | gtatcttgca | gtagccttac | actgccttgt | 60 |
| agctggagag | ccttgtatca | ctgctaacaa | cactgggtat | caacaaagaa | gacaactgca | 120 |
| taaaaatgaa | ataaggagat | actacccagg | ctggggttta | ttttgagtct | ttcagaactt | 180 |
| tctagggata | gaatatctct | gctgacatga | agtcagattc | accagtgcac | agggagtccc | 240 |
| atactggatg | ccagtcacca | tgcccactaa | ggtgcttgcc | agccaggctg | gaaggctcta | 300 |
| ccaagagacg | tctggctgcc | aatgccagag | aaaggaggag | aatgcaagga | ctaaataccg | 360 |
| ccttcgatag | tctgaggaaa | gttgtaccac | aatggggtga | agacaaacaa | ctttccaaat | 420 |
| atgagactct | gcagatggcg | ctgagctaca | tcatggcact | gagcaggatc | ctctcggaag | 480 |
| cagagaggta | cagcaggact | gatccagagg | aatggactaa | tattcaatat | gatcacattg | 540 |
| aggaggagca | gtgcctcagt | tatatggagg | tgagatgccc | aagagactgt | gatcgttacc | 600 |
| tgccccagac | tttttctcac | taggataaga | gcaggcaagg | tactactgac | ctgaagacag | 660 |
| cactgtttta | atataatggg | tcggttatac | agcacccaat | gatacaggga | catttgcatc | 720 |
| atgggctatt | tgtcatgttg | ttttttccaa | tgcaatgctt | atttccttaa | gcaccctacg | 780 |
| ttcaggactg | ggtacatatg | tagggaaccc | caagtgatgc | agcccagagg | atgcggtgct | 840 |
| gcaacggatg | gcagttagtg | agctgtggaa | cactggaaaa | gccaagtgca | ctggtatttt | 900 |
| gtgaaaggac | atgcaagtta | ttatgggtgg | catataaatt | ttacctccat | acagcacagt | 960 |
| gatataactt | cattgcctcc | atcatacctg | tgtgattata | tataaaatgg | tagttcctga | 1020 |
| gtcactactt | tccatgttac | ttatgcactg | ttatcagata | acatagagaa | agtagtattt | 1080 |
| atacattaga | aaaagtacta | tatgtgcata | taaattggcg | tttaaagcag | tctggataaa | 1140 |
| tcattttctg | tggactcttt | tcttacccca | aggagccatt | tatagtttaa | gtgctgctat | 1200 |
| aggcactgct | cataagggaa | aggaaacatt | tttgtcactt | gctgataata | caaattgcat | 1260 |
| tctacaccag | aattcttaat | taactatact | gtcagtgaa | cagaaaggtc | taaattaaaa | 1320 |
| tcaacaagag | gtataattta | catatttttac | cattttctgg | cttctgtctg | ccttttgaga | 1380 |
| gtggcaaatt | acaacgtata | taaaattcct | acaggtctca | atctacttgt | tgctgtaaag | 1440 |
| acaaaccttg | gtgtattttt | aaggaaacct | taagtaattc | ttttggttag | tatacatttc | 1500 |
| ttaaatattt | ttatttgtaa | tgggcgtcaa | ttgtttatttt | gtaaacgcag | ctccaaaaat | 1560 |
| agcagatatg | cttgtatttt | tcaggtatgc | aaatggtatt | tcagcctata | ttgggaaagc | 1620 |
| agtaagcaaa | tctttgtaat | tgaaattgta | gtaaaactga | acatatggtg | aattgcttgg | 1680 |
| caatgtactg | tatacatgct | gacctataag | ggctatgtag | caaagttggg | aaaaagtttt | 1740 |
| ccctatcaaa | atcactgcag | gtttattggt | ttgttgcaga | tagaataata | aaatctgaca | 1800 |
| ttgctgatgt | gggtaaggta | ttttattccc | catttaatat | cttaatcttt | cttcttacac | 1860 |
| tgaaaacatt | actagcccct | tgccaatgta | ttcttatctg | tcaaattcag | gagttcatga | 1920 |
| gacttacctg | tacataatcc | ctatgaaacc | aagacaatgt | gtggggaata | agaggatttg | 1980 |
| ctgcacaaat | tagggcagag | atacatggtc | tgactgtgac | aaatctcctc | ttcttcggag | 2040 |
| cgtttaatct | ccccaaactg | cctttccagg | cactttgttc | tccgaagtcg | cccgaagttg | 2100 |
| cctaacgagg | caacttcagc | acg | | | | 2123 |

<210> SEQ ID NO 52
<211> LENGTH: 138
<212> TYPE: PRT
<213> ORGANISM: FROG

<400> SEQUENCE: 52

Met Lys Ser Asp Ser Pro Val His Arg Glu Ser His Thr Gly Cys Gln
1               5                   10                  15

Ser Pro Cys Pro Leu Arg Cys Leu Pro Ala Arg Leu Glu Gly Ser Thr
            20                  25                  30

Lys Arg Arg Leu Ala Ala Asn Ala Arg Glu Arg Arg Met Gln Gly
        35                  40                  45

Leu Asn Thr Ala Phe Asp Ser Leu Arg Lys Val Val Pro Gln Trp Gly
    50                  55                  60

Glu Asp Lys Gln Leu Ser Lys Tyr Glu Thr Leu Gln Met Ala Leu Ser
65                  70                  75                  80

Tyr Ile Met Ala Leu Ser Arg Ile Leu Ser Glu Ala Glu Arg Tyr Ser
                85                  90                  95

Arg Thr Asp Pro Glu Glu Trp Thr Asn Ile Gln Tyr Asp His Ile Glu
            100                 105                 110

Glu Glu Gln Cys Leu Ser Tyr Met Glu Val Arg Cys Pro Arg Asp Cys
        115                 120                 125

Asp Arg Tyr Leu Pro Gln Thr Phe Ser His
    130                 135

<210> SEQ ID NO 53
<211> LENGTH: 136
<212> TYPE: DNA
<213> ORGANISM: BEETLE

<400> SEQUENCE: 53
gcggcgaatg cgcgcgagcg gcggcggatg aacggcctga atgaagcttt cgatcggcta      60
agacaagtta taccaagctt ggacgctgac cacaaattga gcaagtttga gactctgcag     120
atggcccaga cctaca                                                     136

<210> SEQ ID NO 54
<211> LENGTH: 45
<212> TYPE: PRT
<213> ORGANISM: BEETLE

<400> SEQUENCE: 54

Ala Ala Asn Ala Arg Glu Arg Arg Met Asn Gly Leu Asn Glu Ala
1               5                   10                  15

Phe Asp Arg Leu Arg Gln Val Ile Pro Ser Leu Asp Ala Asp His Lys
            20                  25                  30

Leu Ser Lys Phe Glu Thr Leu Gln Met Ala Gln Thr Tyr
        35                  40                  45

<210> SEQ ID NO 55
<211> LENGTH: 137
<212> TYPE: DNA
<213> ORGANISM: BEETLE

<400> SEQUENCE: 55
gcggcgaatg cgagggagag gcggaggatg aacagtttga atgacgcctt cgacaggctg      60
cgggacgtgg tgccgtccct tgggaacgat cggaagctgt ccaagtttga gacacttcag     120

```
atggcccaga cctacat                                              137
```

<210> SEQ ID NO 56
<211> LENGTH: 45
<212> TYPE: PRT
<213> ORGANISM: BEETLE

<400> SEQUENCE: 56

Ala Ala Asn Ala Arg Glu Arg Arg Met Asn Ser Leu Asn Asp Ala
1               5                   10                  15

Phe Asp Arg Leu Arg Asp Val Val Pro Ser Leu Gly Asn Asp Arg Lys
                20                  25                  30

Leu Ser Lys Phe Glu Thr Leu Gln Met Ala Gln Thr Tyr
                35                  40                  45

<210> SEQ ID NO 57
<211> LENGTH: 1572
<212> TYPE: DNA
<213> ORGANISM: HUMAN
<220> FEATURE:
<221> NAME/KEY: misc_feature
<222> LOCATION: (1497)..(1564)
<223> OTHER INFORMATION: n can be any nucleotide

<400> SEQUENCE: 57

```
gtcctctgca cacaagaact tttctcgggg tgtaaaaact ctttgattgg ctgctcgcac      60
gcgcctgccc gcgccctcca ttggctgaga agacacgcga ccggcgcgag gaggggttg     120 ggagaggagc gggggagac tgagtggcgc gtgccgcttt ttaaagggc gcagcgcctt     180 cagcaaccgg agaagcatag ttgcacgcga cctggtgtgt gatctccgag tgggtggggg     240
agggtcgagg agggaaaaaa aaataagacg ttgcagaaga gacccggaaa gggccttttt     300
tttggttgag ctggtgtccc agtgctgcct ccgatcctga gcgtccgagc ctttgcagtg     360
caatgtcccg cctgctgcat gcagaagagt gggctgaagt gaaggagttg ggagaccacc     420
atcgccagcc ccagccgcat catctcccgc aaccgccgcc gccgcgcag ccacctgcaa      480 cttttgcagg c gagagagcat cccgtctacc cgcctgagct gtccctcctg gacagcaccg      540
acccacgcgc ctggctggct cccactttgc agggcatctg cacggcacgc gccgcccagt     600
atttgctaca ttccccggag ctgggtgcct cagaggccgc tgcgcccgg gacgaggtgg      660 acggccgggg ggagctggta aggaggagca gcggcggtgc cagcagcagc aagagccccg     720
ggccggtgaa agtgcgggaa cagctgtgca agctgaaagg cggggtggtg gtagacgagc     780
tgggctgcag ccgccaacgg gccccttcca gcaaacaggt gaatggggtg cagaagcaga     840
gacggctagc agccaacgcc agggagcggc gcaggatgca tggctgaac cacgccttcg      900 accagctgcg caatgttatc ccgtcgttca caacgacaa gaagctgtcc aaatatgaga      960
ccctgcagat ggcccaaatc tacatcaacg ccttgtccga gctgctacaa cgcccagcg     1020 gaggggaaca gccaccgccg cctccagcct cctgcaaaag cgaccaccac caccttcgca     1080
ccgcggcctc ctatgaaggg ggcgcgggca acgcgaccgc agctggggct cagcaggctt     1140
ccggagggag ccagcggccg acccgccg ggagttgccg gactcgcttc tcagcccag      1200 cttctgcggg agggtactcg gtgcagctgg acgtctgca cttctcgact ttcgaggaca     1260
gcgccctgac agcgatgatg gcgcaaaaga atttgtctcc ttctctcccc gggagcatct     1320
tgcagccagt gcaggaggaa aacagcaaaa cttcgcctcg gtcccacaga agcgacgggg     1380
aattttcccc ccattcccat tacagtgact cggatgaggc aagttaggaa ggtgacagaa     1440
```

```
gcctgaaaac tgagacagaa acaaaactgc cctttcccag tgcgcgggaa gccccgnggt    1500
taangatccc cgcacccttt aatttnggct ctgcgatggc cgttgtttag caacgacttg    1560
gctncagatg gt                                                        1572
```

<210> SEQ ID NO 58
<211> LENGTH: 354
<212> TYPE: PRT
<213> ORGANISM: HUMAN

<400> SEQUENCE: 58

```
Met Ser Arg Leu Leu His Ala Glu Glu Trp Ala Glu Val Lys Glu Leu
1               5                   10                  15

Gly Asp His His Arg Gln Pro Gln Pro His His Leu Pro Gln Pro Pro
                20                  25                  30

Pro Pro Pro Gln Pro Pro Ala Thr Leu Gln Ala Arg Glu His Pro Val
            35                  40                  45

Tyr Pro Pro Glu Leu Ser Leu Leu Asp Ser Thr Asp Pro Arg Ala Trp
    50                  55                  60

Leu Ala Pro Thr Leu Gln Gly Ile Cys Thr Ala Arg Ala Ala Gln Tyr
65                  70                  75                  80

Leu Leu His Ser Pro Glu Leu Gly Ala Ser Glu Ala Ala Ala Pro Arg
                85                  90                  95

Asp Glu Val Asp Gly Arg Gly Glu Leu Val Arg Arg Ser Ser Gly Gly
            100                 105                 110

Ala Ser Ser Ser Lys Ser Pro Gly Pro Val Lys Val Arg Glu Gln Leu
        115                 120                 125

Cys Lys Leu Lys Gly Gly Val Val Asp Glu Leu Gly Cys Ser Arg
130                 135                 140

Gln Arg Ala Pro Ser Ser Lys Gln Val Asn Gly Val Gln Lys Gln Arg
145                 150                 155                 160

Arg Leu Ala Ala Asn Ala Arg Glu Arg Arg Met His Gly Leu Asn
                165                 170                 175

His Ala Phe Asp Gln Leu Arg Asn Val Ile Pro Ser Phe Asn Asn Asp
            180                 185                 190

Lys Lys Leu Ser Lys Tyr Glu Thr Leu Gln Met Ala Gln Ile Tyr Ile
        195                 200                 205

Asn Ala Leu Ser Glu Leu Leu Gln Thr Pro Ser Gly Gly Glu Gln Pro
    210                 215                 220

Pro Pro Pro Ala Ser Cys Lys Ser Asp His His Leu Arg Thr
225                 230                 235                 240

Ala Ala Ser Tyr Glu Gly Gly Ala Gly Asn Ala Thr Ala Ala Gly Ala
                245                 250                 255

Gln Gln Ala Ser Gly Gly Ser Gln Arg Pro Thr Pro Gly Ser Cys
            260                 265                 270

Arg Thr Arg Phe Ser Ala Pro Ala Ser Ala Gly Gly Tyr Ser Val Gln
        275                 280                 285

Leu Asp Ala Leu His Phe Ser Thr Phe Glu Asp Ser Ala Leu Thr Ala
    290                 295                 300

Met Met Ala Gln Lys Asn Leu Ser Pro Ser Leu Pro Gly Ser Ile Leu
305                 310                 315                 320

Gln Pro Val Gln Glu Glu Asn Ser Lys Thr Ser Pro Arg Ser His Arg
                325                 330                 335

Ser Asp Gly Glu Phe Ser Pro His Ser His Tyr Ser Asp Ser Asp Glu
            340                 345                 350
```

Ala Ser

<210> SEQ ID NO 59
<211> LENGTH: 485
<212> TYPE: DNA
<213> ORGANISM: CHICKEN
<220> FEATURE:
<221> NAME/KEY: misc_feature
<222> LOCATION: (147)..(147)
<223> OTHER INFORMATION: n can be any nucleotide

<400> SEQUENCE: 59

```
ccgctgctgg ggccggacgg ggcggctgcg gcttcgcccc cggctggctg ggcgtgtgct      60
gcgccgcacg cgtgcccgcc gcgtcgccgc gctacctgct gcccgccgac gaggaggacg     120
aggcggcccg tggcgggggg cgcggcncgc gttccggcgg gagcagcccc ggggagcgc      180
ggggcggcgg cgggcgcgcg gggcggcggc ggcggggccg ggccgcgggc gcaggtgagc     240
ggcgtgcaga agcagcggcg gctggcggcc aacgcgcggg agcggcggcg gatgcacggg     300
ctgaaccacg ccttcgacca gctgcgtaat gtcatcccct ccttcaacaa cgacaagaag     360
ctctccaagt acgagacgct gcagatggcg caaatctaca tcagcgccct cgccgagctg     420
ctgcacgggc cgcccgcgcc ccccgagccg cccgccaagg ccgagctccg cggggccccc     480
ttcga                                                                 485
```

<210> SEQ ID NO 60
<211> LENGTH: 161
<212> TYPE: PRT
<213> ORGANISM: CHICKEN

<400> SEQUENCE: 60

```
Pro Leu Leu Gly Pro Asp Gly Ala Ala Ala Ser Pro Pro Ala Gly
1               5                   10                  15

Trp Ala Cys Ala Ala Pro His Ala Cys Pro Pro Arg Arg Arg Ala Thr
                20                  25                  30

Cys Cys Pro Pro Thr Arg Arg Thr Arg Arg Pro Val Ala Gly Gly Ala
    35                  40                  45

Ala Arg Val Pro Ala Gly Ala Ala Pro Gly Glu Arg Gly Ala Ala Ala
    50                  55                  60

Gly Ala Arg Gly Gly Gly Gly Ala Gly Pro Arg Ala Gln Val Ser
65                  70                  75                  80

Gly Val Gln Lys Gln Arg Arg Leu Ala Ala Asn Ala Arg Glu Arg Arg
                85                  90                  95

Arg Met His Gly Leu Asn His Ala Phe Asp Gln Leu Arg Asn Val Ile
                100                 105                 110

Pro Ser Phe Asn Asn Asp Lys Lys Leu Ser Lys Tyr Glu Thr Leu Gln
        115                 120                 125

Met Ala Gln Ile Tyr Ile Ser Ala Leu Ala Glu Leu Leu His Gly Pro
    130                 135                 140

Pro Ala Pro Pro Glu Pro Pro Lys Ala Glu Leu Arg Gly Ala Pro
145                 150                 155                 160

Phe
```

<210> SEQ ID NO 61
<211> LENGTH: 138
<212> TYPE: DNA
<213> ORGANISM: PUFFER FISH

<400> SEQUENCE: 61

| | | | | | |
|---|---|---|---|---|---|
| gcggcgaacg | cgagggagag | gaggagaatg | cacggcctga | ataaagcgtt | tgacgaactg | 60 |
| aggagcgtca | ttccttccct | ggaaaatgag | agaaagctct | ccaagtatga | cactctccag | 120 |
| atggcccaaa | cctacatc | | | | | 138 |

<210> SEQ ID NO 62
<211> LENGTH: 46
<212> TYPE: PRT
<213> ORGANISM: PUFFER FISH

<400> SEQUENCE: 62

Ala Ala Asn Ala Arg Glu Arg Arg Met His Gly Leu Asn Lys Ala
1               5                   10                  15

Phe Asp Glu Leu Arg Ser Val Ile Pro Ser Leu Glu Asn Glu Arg Lys
            20                  25                  30

Leu Ser Lys Tyr Asp Thr Leu Gln Met Ala Gln Thr Tyr Ile
        35                  40                  45

<210> SEQ ID NO 63
<211> LENGTH: 1477
<212> TYPE: DNA
<213> ORGANISM: DROSOPHILA

<400> SEQUENCE: 63

| | | | | | |
|---|---|---|---|---|---|
| atcatcttgt | tagcggcttt | agagccgaat | cgttttctag | cgccatttta | agctcgcaac | 60 |
| gaactgaggt | ataaccgggc | tctctgagac | cgctgcaact | caccaccaac | tgccattggt | 120 |
| cgtgccactc | gggcggcacg | tgctgccttc | tgtggcaact | cgtttacctg | cccccctacc | 180 |
| tgcctttcag | gcccttctga | ccgtcgtggt | ggatttgtga | gtataaatag | ggccgaaagg | 240 |
| acgagagacc | agtcagaaac | ccgccagcac | tcgcagcgtt | cgtatcgttt | catccagcaa | 300 |
| cataacacca | ccatacagca | gcagcaacat | gtcgtccagt | gagatctatc | gctactacta | 360 |
| caagacctcc | gaggacttgc | agggcttcaa | gacagccgcc | gccgagccgt | acttcaatcc | 420 |
| catggcagcc | tacaatcccg | gcgtgaccca | ctaccagttc | aatggcaaca | ccctggccag | 480 |
| cagcagcaac | tacttgtcgg | ccaatggctt | catcagcttc | gagcaggcca | gttccgatgg | 540 |
| ctggatctcc | tcctcgccgg | ctagccaccg | atctgagagt | cccagtatg | tggatctcaa | 600 |
| taccatgtac | aatggaggct | gcaacaacat | ggcccagaac | caacaatacg | gaatgattat | 660 |
| ggagcagtct | gttgtttcca | cagcgcctgc | aattccagtg | gcctctcctc | cggcagtgga | 720 |
| ggtcatgggc | tcctccaacg | tgggcacttg | caaaacgatt | ccagcctcag | cagctccgaa | 780 |
| accgaagcgt | agctatacca | agaagaacca | gccaagcacc | accgccacct | ccacaccgac | 840 |
| tgcagctgcg | gagtcatctg | cctcagtgaa | tctctacacg | gaggagttcc | agaactttga | 900 |
| ctttgacaac | tccgccttgt | tcgatgacag | cgtcgaggat | gacgaggacc | tcatgctctt | 960 |
| cagtggcggt | gaggacttcg | atggcaatga | tggatccttt | gacttggccg | atggtgagaa | 1020 |
| ccaagatgcc | gctgccggag | gctctggaaa | gaagaggcgt | ggcaagcaga | tcacacccgt | 1080 |
| cgtgaagagg | aagcgtcgcc | tggccgccaa | tgcacgtgag | cgtcgtcgga | tgcagaacct | 1140 |
| caaccaggcc | ttcgatcgtc | tccgccagta | ccttccctgt | ctgggaaacg | atcgccagct | 1200 |
| gtccaaacac | gagaccctcc | aaatgggccca | gacctacata | tccgctctcg | gggatctgct | 1260 |
| gcgctgaatt | cccggatccc | gatcccagtc | caagtactac | ttctcagtta | ttgttggagc | 1320 |
| ttgccaaatg | ttgtagctac | tttgtatata | ttgcctggag | cccagtagtg | aattaccgct | 1380 |

```
taagtattat gctgtttatt gtttagttaa ttagcctaaa tggaagacaa tgattaagac    1440
taaggaagac aaaataaaag caccattaat aatttaa                             1477
```

<210> SEQ ID NO 64
<211> LENGTH: 312
<212> TYPE: PRT
<213> ORGANISM: DROSOPHILA

<400> SEQUENCE: 64

```
Met Ser Ser Ser Glu Ile Tyr Arg Tyr Tyr Tyr Lys Thr Ser Glu Asp
1               5                   10                  15

Leu Gln Gly Phe Lys Thr Ala Ala Glu Pro Tyr Phe Asn Pro Met
            20                  25                  30

Ala Ala Tyr Asn Pro Gly Val Thr His Tyr Gln Phe Asn Gly Asn Thr
            35                  40                  45

Leu Ala Ser Ser Asn Tyr Leu Ser Ala Asn Gly Phe Ile Ser Phe
    50                  55                  60

Glu Gln Ala Ser Ser Asp Gly Trp Ile Ser Ser Pro Ala Ser His
65                  70                  75                  80

Arg Ser Glu Ser Pro Glu Tyr Val Asp Leu Asn Thr Met Tyr Asn Gly
                85                  90                  95

Gly Cys Asn Asn Met Ala Gln Asn Gln Gln Tyr Gly Met Ile Met Glu
            100                 105                 110

Gln Ser Val Val Ser Thr Ala Pro Ala Ile Pro Val Ala Ser Pro Pro
        115                 120                 125

Ala Val Glu Val Met Gly Ser Ser Asn Val Gly Thr Cys Lys Thr Ile
    130                 135                 140

Pro Ala Ser Ala Ala Pro Lys Pro Lys Arg Ser Tyr Thr Lys Lys Asn
145                 150                 155                 160

Gln Pro Ser Thr Thr Ala Thr Ser Thr Pro Thr Ala Ala Glu Ser
                165                 170                 175

Ser Ala Ser Val Asn Leu Tyr Thr Glu Glu Phe Gln Asn Phe Asp Phe
            180                 185                 190

Asp Asn Ser Ala Leu Phe Asp Asp Ser Val Glu Asp Asp Glu Asp Leu
        195                 200                 205

Met Leu Phe Ser Gly Gly Glu Asp Phe Asp Gly Asn Asp Gly Ser Phe
    210                 215                 220

Asp Leu Ala Asp Gly Glu Asn Gln Asp Ala Ala Gly Gly Ser Gly
225                 230                 235                 240

Lys Lys Arg Arg Gly Lys Gln Ile Thr Pro Val Val Lys Arg Lys Arg
                245                 250                 255

Arg Leu Ala Ala Asn Ala Arg Glu Arg Arg Met Gly Asn Leu Asn
            260                 265                 270

Gln Ala Phe Asp Arg Leu Arg Gln Tyr Leu Pro Cys Leu Gly Asn Asp
        275                 280                 285

Arg Gln Leu Ser Lys His Glu Thr Leu Gln Met Ala Gln Thr Tyr Ile
    290                 295                 300

Ser Ala Leu Gly Asp Leu Leu Arg
305                 310
```

<210> SEQ ID NO 65
<211> LENGTH: 907
<212> TYPE: DNA
<213> ORGANISM: FROG

<400> SEQUENCE: 65

```
gccccggggc cactctgcgc acttgtcggg acttattcgc acttacctgt catggcccgt      60
ctgctacacg gcgctgctac tgccgctgac tggtgcgagc tgaaggagct tccatccgag     120
gccgggctct tggccagaga ttacctacta gacagcagcg accccgcgc ctggctctcc      180 gccacttccc tgcaaagtcg ccctgagtac gtgctgcacc cccgggccg ggccgggcgc      240 acaaggtgcg ggaactgtgc aaactgaagg ggctgcggga tgatgatgat gatgaggagg     300
atgatgagga ggaggaagag agatccgagg ggctgtgcag acacaggggt ccccctggca     360
agggccctgg tggggttcag aagcagagga gactggcagc caatgccagg agaggaggag     420
ggatgcacgg gctcaatcat gccttcgatc agctccgtaa tgtcatccct ccttcaata     480 acgacaagaa actctccaaa tacgagaccc tgcagatggc tcagatctac atcaacgccc    540
tgtccgacct gctgcaggcg ccccccgact ccagagatcc ccctgcccg cccacctacc     600 aactgcattc ggggccagag cccaggttag tccagtctgg cagcatgaga ttctcggaga    660
cttccccccg acagtccccc ctcagccaat tccaggaggg agctgctccc agaagggaat    720
aggatctggg cccatcttca tcttctcggg aagacatcgc ccatcttcat cttcggggag    780
aagacagcaa gacatcgcaa gatctcatcg gagtgacggc gaattccggt ctccctatag    840
tgagtcgtat aatttcgat aagccagctg cattaatgaa tcggccaaac gcgcgggag     900 aggcggt                                                             907

<210> SEQ ID NO 66
<211> LENGTH: 259
<212> TYPE: PRT
<213> ORGANISM: FROG

<400> SEQUENCE: 66

Met Ala Arg Leu Leu His Gly Ala Ala Thr Ala Ala Asp Trp Cys Glu
1               5                   10                  15

Leu Lys Glu Leu Pro Ser Glu Ala Gly Leu Leu Ala Arg Asp Tyr Leu
                20                  25                  30

Leu Asp Ser Ser Asp Pro Arg Ala Trp Leu Ser Ala Thr Ser Leu Gln
            35                  40                  45

Ser Arg Pro Glu Tyr Val Leu His Pro Pro Gly Arg Ala His Lys Val
        50                  55                  60

Arg Glu Leu Cys Lys Leu Lys Gly Leu Arg Asp Asp Asp Asp Glu
65                  70                  75                  80

Glu Glu Asp Asp Glu Glu Glu Glu Arg Ser Glu Gly Leu Cys Arg
                85                  90                  95

His Arg Gly Pro Pro Gly Lys Gly Pro Gly Gly Val Gln Lys Gln Arg
            100                 105                 110

Arg Leu Ala Ala Asn Ala Arg Glu Arg Arg Met His Gly Leu Asn
        115                 120                 125

His Ala Phe Asp Gln Leu Arg Asn Val Ile Pro Ser Phe Asn Asn Asp
    130                 135                 140

Lys Lys Leu Ser Lys Tyr Glu Thr Leu Gln Met Ala Gln Ile Tyr Ile
145                 150                 155                 160

Asn Ala Leu Ser Asp Leu Leu Gln Ala Pro Pro Asp Ser Arg Asp Pro
                165                 170                 175

Pro Cys Pro Pro Thr Tyr Gln Leu His Ser Gly Pro Glu Pro Arg Leu
            180                 185                 190

Val Gln Ser Gly Ser Cys Met Arg Phe Ser Gly Asp Phe Pro Gly Gln
        195                 200                 205
```

```
Ser Pro Leu Ser Phe Gln Phe Gln Glu Gly Ala Ala Leu Ser Gly Lys
    210             215                 220

Gly Ile Gly Ser Ala Pro Ser Ser Ser Gly Glu Asp Ser Lys Thr
225             230                 235                 240

Ser Pro Arg Ser His Arg Ser Asp Gly Glu Phe Arg Ser Pro Tyr Ser
                245                 250                 255

Glu Ser Tyr

<210> SEQ ID NO 67
<211> LENGTH: 19
<212> TYPE: DNA
<213> ORGANISM: SYNTHETIC CONSTRUCT

<400> SEQUENCE: 67
tgaagctttt ggctttgag                                           19

<210> SEQ ID NO 68
<211> LENGTH: 19
<212> TYPE: DNA
<213> ORGANISM: SYNTHETIC CONSTRUCT

<400> SEQUENCE: 68
ccgctgccaa attctttgg                                           19

<210> SEQ ID NO 69
<211> LENGTH: 37
<212> TYPE: DNA
<213> ORGANISM: HUMAN

<400> SEQUENCE: 69
gggggcactg acagtaatgc atgccgtatt cgaagtt                       37

<210> SEQ ID NO 70
<211> LENGTH: 21
<212> TYPE: PRT
<213> ORGANISM: HUMAN

<400> SEQUENCE: 70

Ala Ala Asn Ala Arg Glu Arg Arg Arg Met His Gly Leu Asn His Ala
1               5                   10                  15

Phe Asp Gln Leu Arg
            20
```